(12) United States Patent
Beam et al.

(10) Patent No.: US 7,122,057 B2
(45) Date of Patent: Oct. 17, 2006

(54) METHOD AND APPARATUS FOR ENGINEERED REGENERATIVE BIOSTRUCTURES SUCH AS HYDROXYAPATITE SUBSTRATES FOR BONE HEALING APPLICATIONS

(75) Inventors: Heather Ann Beam, North Brunswick, NJ (US); Thomas J. Bradbury, Yardley, PA (US); Kathleen D. Chesmel, Cream Ridge, NJ (US); Christopher M. Gaylo, Princeton Junction, NJ (US); Alfred Anthony Litwak, Manasquan, NJ (US); Qing Liu, Lawrenceville, NJ (US); Peter Albert Materna, Metuchen, NJ (US); Donald Monkhouse, Radnor, PA (US); Jennifer Patterson, Seattle, WA (US); Timothy J. Pryor, Yardley, PA (US); Sunil Saini, Plainsboro, NJ (US); Henry Leon Surprenant, Phoenixville, PA (US); Chen-Chao Wang, West Windsor, NJ (US); Thomas George West, Lawrenceville, NJ (US); Jaedeok Yoo, West Orange, NJ (US)

(73) Assignee: Therics, LLC, Akron, OH (US)

( * ) Notice: Subject to any disclaimer, the term of this patent is extended or adjusted under 35 U.S.C. 154(b) by 341 days.

(21) Appl. No.: 10/122,129

(22) Filed: Apr. 12, 2002

(65) Prior Publication Data
US 2003/0065400 A1 Apr. 3, 2003

Related U.S. Application Data

(60) Provisional application No. 60/283,564, filed on Apr. 12, 2001.

(51) Int. Cl.
*A61F 2/28* (2006.01)

(52) U.S. Cl. .................. 623/23.51; 623/23.56
(58) Field of Classification Search ............ 623/16.11, 623/23.51, 23.61; 419/2, 5; 264/43, 44; 424/423
See application file for complete search history.

(56) References Cited

U.S. PATENT DOCUMENTS

| | | | |
|---|---|---|---|
| 3,662,405 A * | 5/1972 | Bortz et al. .............. | 623/23.51 |
| 3,713,860 A | 1/1973 | Auskern ...................... | 117/8.5 |
| 4,000,525 A | 1/1977 | Klawitter et al. | |
| 4,158,684 A | 6/1979 | Klawitter et al. ............. | 264/43 |
| 4,192,021 A * | 3/1980 | Deibig et al. ............ | 623/23.61 |

(Continued)

FOREIGN PATENT DOCUMENTS

EP          0395187 A2    10/1990

(Continued)

OTHER PUBLICATIONS

Portions of TheriRidge 510(k) FDA Submission.

*Primary Examiner*—Eduardo C. Robert
*Assistant Examiner*—David Cornstock
(74) *Attorney, Agent, or Firm*—Robert H. Eichenberger; Middleton Reutlinger

(57) ABSTRACT

An engineered regenerative biostructure (erb) for implantation into a human body as a bone substitute, which includes an internal microstructure, mesostructure and/or macrostructure to provide improved bone in-growth, and methods for making the erb. Under one aspect of the invention, the biostructure has resorbable and nonresorbable regions. Under another aspect of the invention, the biostructure is constructed of hydroxyapatite, tricalcium phosphate and/or demineralized bone. Under yet another aspect of the invention, the porous biostructure is partially or fully infused with a resorbable, nonresorbable or dissolvable material.

60 Claims, 26 Drawing Sheets
(3 of 26 Drawing Sheet(s) Filed in Color)

U.S. PATENT DOCUMENTS

| | | | |
|---|---|---|---|
| 4,218,255 A | 8/1980 | Bajpai et al. | |
| 4,222,128 A | 9/1980 | Tomonaga et al. | 3/1.9 |
| 4,253,877 A | 3/1981 | Miale et al. | 106/18.35 |
| 4,308,064 A | 12/1981 | Takami et al. | |
| 4,330,891 A * | 5/1982 | Branemark et al. | 623/23.61 |
| 4,431,428 A | 2/1984 | Schmer | 604/897 |
| 4,492,577 A | 1/1985 | Farris et al. | 433/201 |
| 4,629,464 A * | 12/1986 | Takata et al. | 623/23.61 |
| 4,637,931 A * | 1/1987 | Schmitz | 424/426 |
| 4,695,455 A | 9/1987 | Barnes et al. | 424/93 |
| 4,722,870 A | 2/1988 | White | 428/621 |
| 4,737,411 A | 4/1988 | Graves, Jr. et al. | 428/403 |
| 4,780,450 A | 10/1988 | Sauk et al. | |
| 4,843,112 A | 6/1989 | Gerhart et al. | |
| 4,870,055 A | 9/1989 | Urry et al. | 514/12 |
| 4,880,610 A | 11/1989 | Costantz | |
| RE33,161 E | 2/1990 | Brown et al. | |
| RE33,221 E | 5/1990 | Brown et al. | |
| 4,976,736 A | 12/1990 | White et al. | |
| 5,011,495 A * | 4/1991 | Hollinger | 424/423 |
| 5,034,352 A | 7/1991 | Vit et al. | |
| 5,035,896 A | 7/1991 | Apfel et al. | 424/456 |
| 5,051,304 A | 9/1991 | David et al. | 428/402.2 |
| 5,053,212 A | 10/1991 | Costantz et al. | |
| 5,079,018 A | 1/1992 | Ecanow | 426/385 |
| 5,132,117 A | 7/1992 | Speaker et al. | 424/490 |
| 5,167,502 A | 12/1992 | Kawahara et al. | 433/173 |
| 5,204,055 A | 4/1993 | Sachs et al. | 419/2 |
| 5,250,516 A | 10/1993 | Urry | 514/17 |
| 5,336,256 A | 8/1994 | Urry | 623/1 |
| 5,356,629 A * | 10/1994 | Sander et al. | 424/422 |
| 5,370,692 A | 12/1994 | Fink et al. | |
| 5,455,100 A | 10/1995 | White | |
| 5,489,306 A | 2/1996 | Gorski | 623/16 |
| 5,490,962 A | 2/1996 | Cima et al. | |
| 5,518,680 A | 5/1996 | Cima et al. | |
| 5,531,794 A | 7/1996 | Takagi et al. | 623/16 |
| 5,626,861 A | 5/1997 | Laurencin et al. | |
| 5,639,402 A | 6/1997 | Barlow et al. | |
| 5,643,672 A | 7/1997 | Marchi et al. | 428/402 |
| 5,660,849 A * | 8/1997 | Polson et al. | 424/426 |
| 5,676,745 A | 10/1997 | Kelly et al. | |
| 5,686,113 A | 11/1997 | Speaker et al. | 424/490 |
| 5,759,582 A | 6/1998 | Leong et al. | 424/492 |
| 5,766,618 A | 6/1998 | Laurencin et al. | |
| 5,769,897 A * | 6/1998 | Harle | 424/423 |
| 5,837,752 A | 11/1998 | Shastri et al. | |
| 5,843,348 A | 12/1998 | Giordano | |
| 5,861,159 A | 1/1999 | Pardoll et al. | 424/184.1 |
| 5,869,170 A * | 2/1999 | Cima et al. | 428/304.4 |
| 5,876,446 A | 3/1999 | Agrawal et al. | |
| 5,876,452 A | 3/1999 | Athanasiou et al. | |
| 5,939,039 A | 8/1999 | Sapieszko et al. | |
| 5,947,893 A | 9/1999 | Agrawal et al. | |
| 6,010,336 A | 1/2000 | Shimotoso et al. | 433/201.1 |
| 6,018,095 A | 1/2000 | Lerch et al. | |
| 6,077,989 A | 6/2000 | Kandel et al. | |
| 6,136,029 A | 10/2000 | Johnson et al. | |
| 6,139,574 A | 10/2000 | Vacanti et al. | |
| 6,149,688 A | 11/2000 | Brosnahan et al. | |
| 6,150,459 A | 11/2000 | Mayes et al. | |
| 6,159,417 A | 12/2000 | Giordano | |
| 6,165,486 A | 12/2000 | Marra et al. | |
| 6,174,167 B1 | 1/2001 | Wöhrle | |
| 6,176,874 B1 * | 1/2001 | Vacanti et al. | 623/1.44 |
| 6,180,141 B1 | 1/2001 | Lemercier et al. | 424/489 |
| 6,187,046 B1 | 2/2001 | Yamamoto et al. | 623/16.11 |
| 6,187,329 B1 | 2/2001 | Agrawal et al. | |
| 6,193,970 B1 | 2/2001 | Pardoll et al. | 424/184.1 |
| 6,201,039 B1 | 3/2001 | Brown et al. | |
| 6,203,574 B1 | 3/2001 | Kawamura | 623/16.11 |
| 6,206,924 B1 | 3/2001 | Timm | |
| 6,207,749 B1 | 3/2001 | Mayes et al. | |
| 6,214,368 B1 | 4/2001 | Lee et al. | |
| 6,224,630 B1 | 5/2001 | Bao et al. | |
| 6,224,905 B1 | 5/2001 | Lawrence et al. | 424/464 |
| 6,228,339 B1 | 5/2001 | Ota et al. | |
| 6,235,225 B1 | 5/2001 | Okada et al. | 264/44 |
| 6,235,665 B1 | 5/2001 | Pickrell et al. | |
| 6,241,771 B1 | 6/2001 | Gresser et al. | |
| 6,242,247 B1 | 6/2001 | Rieser et al. | 435/297.1 |
| 6,255,359 B1 | 7/2001 | Agrawal et al. | |
| 6,261,322 B1 | 7/2001 | Despres, III et al. | |
| 6,264,701 B1 | 7/2001 | Brekke | |
| 6,277,394 B1 | 8/2001 | Sierra | |
| 6,283,997 B1 | 9/2001 | Garg et al. | |
| 6,287,341 B1 | 9/2001 | Lee et al. | |
| 6,294,187 B1 | 9/2001 | Boyce et al. | 424/422 |
| 6,296,667 B1 | 10/2001 | Johnson et al. | |
| 6,302,913 B1 | 10/2001 | Ripamonti et al. | |
| 6,309,669 B1 | 10/2001 | Setterstrom et al. | 424/486 |
| 6,325,992 B1 | 12/2001 | Chow et al. | |
| 6,331,312 B1 | 12/2001 | Lee et al. | |
| 6,332,728 B1 | 12/2001 | Ito et al. | |
| 6,364,909 B1 | 4/2002 | McGee | |
| 6,376,573 B1 | 4/2002 | White et al. | |
| 6,383,519 B1 | 5/2002 | Sapieszko et al. | |
| 6,399,700 B1 | 6/2002 | Mayes et al. | |
| 6,454,811 B1 | 9/2002 | Sherwood et al. | |
| 6,458,162 B1 | 10/2002 | Koblish et al. | |
| 6,471,993 B1 | 10/2002 | Shastri et al. | |
| 6,511,510 B1 | 1/2003 | de Bruijn et al. | |
| 6,521,246 B1 | 2/2003 | Sapieszko et al. | |
| 6,530,958 B1 | 3/2003 | Cima et al. | |
| 6,540,784 B1 | 4/2003 | Barlow et al. | |
| 6,548,002 B1 | 4/2003 | Gresser et al. | |
| 6,558,422 B1 * | 5/2003 | Baker et al. | 623/16.11 |
| 6,605,293 B1 | 8/2003 | Giordano et al. | |
| 6,767,550 B1 | 7/2004 | Gènin et al. | |

FOREIGN PATENT DOCUMENTS

| | | |
|---|---|---|
| EP | 0634149 A1 | 1/1995 |
| EP | 0701808 A2 | 3/1996 |
| EP | 0701808 A2 | 3/1996 |
| EP | 0803241 A2 | 10/1997 |
| EP | 0803241 A2 | 10/1997 |
| WO | WO 97/46178 | 12/1997 |
| WO | WO 99/16478 | 4/1999 |
| WO | WO 00/71083 | 11/2000 |
| WO | WO 01/12106 | 2/2001 |

* cited by examiner

2010

METHOD AND APPARATUS FOR ENGINEERED REGENERATIVE BIOSTRUCTURES SUCH AS HYDROXYAPATITE SUBSTRATES FOR BONE HEALING APPLICATIONS

CROSS-REFERENCE TO RELATED APPLICATIONS

This application claims the benefit of U.S. Provisional Patent Application No. 60/283,564 filed Apr. 12, 2001.

BACKGROUND OF THE INVENTION

1. Field of the Invention

This invention relates to engineered regenerative biostructures, and more particularly to porous bone augmentation articles with microporosity, mesoporosity and/or macrochannels and other osteoconductive features and other materials.

2. Description of the Related Art

It is currently of great interest to identify and exploit what features of implantable materials are conducive to in-growth of new bone. Bone response to grafting materials depends on a complex interaction between the chemical composition of the material, surface texture, pore size and porosity, implant geometry, and degradation products. Grafting alternatives have included: autogenous or autograft bone (bone harvested from another site within the patient); allografts (bone harvested from a cadaver); and a range of synthetic scaffolds materials. Synthetic scaffolds materials have included: coralline hydroxyapatite; mixtures of hydroxyapatite, tricalcium phosphate, and bovine collagen; human demineralized bone and glycerol; and calcium sulfate pellets. Such compounds are osteoconductive and in some cases resorbable.

Most of the literature on bone in-growth has taught that pore size should be at least 100 microns in order to promote bone in-growth. All of these products have limitations. Human-derived materials depend on availability of suitable donors. Within any given sample, naturally occurring materials and their derivatives have large variations in both porosity and permeability. Degradation products of some classes of material can activate inflammatory responses. Matching porosity and internal architecture to specific tissue response remains an unmet challenge.

PLA and PGA have been used in synthetic bone implants. PLA and PGA were less than ideal for tissue-engineered scaffolds for bone healing applications, especially in areas of low vasculature, where degradation products could not be quickly eliminated from the implant site. PLA and PGA released acidic degradation products, often causing newly formed bone in those areas to be resorbed. Further, microcrystalline particulate debris, created during the resorption/breakdown process, has been implicated in stimulating a significant inflammatory response, especially with long-term implants.

In other applications, hydroxyapatite (HA) has been used in either granular form or block form. Several challenges exist with using HA in this form. It has been difficult to shape blocks of HA. The particulate form of the material has been used to shape or conform to the geometry of a surgical site, thus eliminating the shaping problem, but. The particulates often migrate, resulting in voids and associated vulnerability to inflammation within the surgical site. Furthermore, fully dense HA has produced disappointing results in bone implants largely since it can only become fixed to the bone via surface attachment.

BRIEF SUMMARY OF THE INVENTION

The present invention overcomes the limitations of the prior art and provides additional benefits. Under one aspect of the invention, an engineered regenerative biostructure (ERB) includes an internal microstructure, mesostructure and/or macrostructure. Under another aspect of the invention, the biostructure comprises Hydroxyapatite. Under another aspect of the invention, the biostructure has resorbable and nonresorbable regions. Under yet another aspect of the invention, the biostructure comprises demineralized bone matrix. Under yet another aspect of the invention, the porous biostructure is partially or fully infused with one or more substances or categories of substances. The invention also includes associated manufacturing methods for all of these aspects.

BRIEF DESCRIPTION OF THE SEVERAL VIEWS OF THE DRAWINGS

The patent or application file contains at least one drawing executed in color. Copies of this patent or patent application publication with color drawings(s) will be provided by the Office upon request and payment of the necessary fee.

Figure 1:
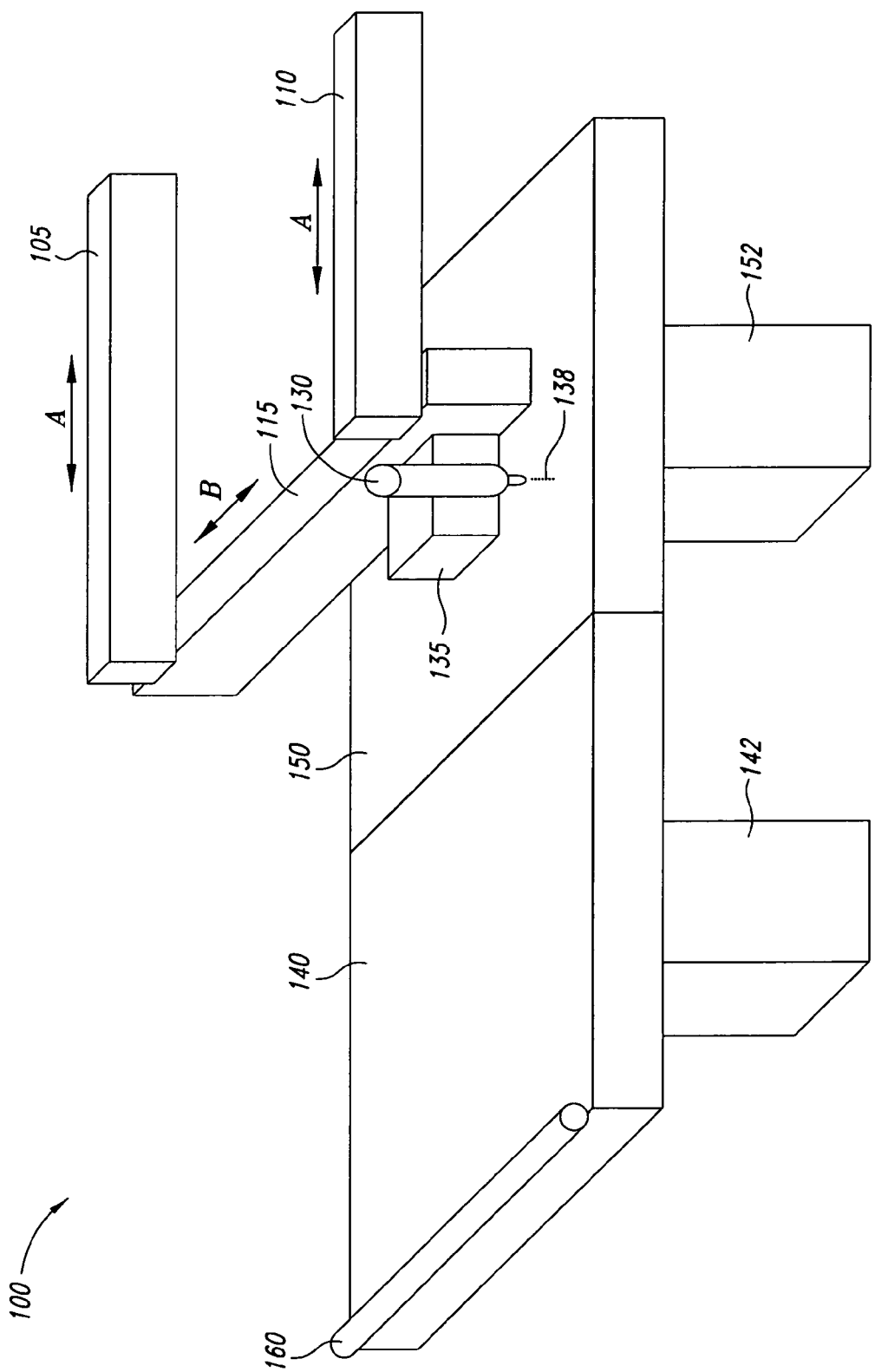
FIG. 1 illustrates an isometric view of a three-dimensional printing apparatus in accordance with the prior art.

In the drawings, like reference numbers identify similar elements or steps. For ease in identifying the discussion of any particular element, the most significant digit in a reference number refers to the FIG. number in which that element is first introduced (e.g., element 204 is first introduced and discussed with respect to FIG. 2).

DETAILED DESCRIPTION OF THE INVENTION

Article of Manufacture: Engineered Regenerative Biostructure (ERB)

The engineered regenerative biostructure (ERB) of the present invention, when made of a ceramic material, comprises powder particles that are partially joined directly to each other in a manner that leaves some porosity between the partially joined particles. The biostructure further includes engineered or designed internal microporosity, mesoporosity and/or macroporosity to improve osteoconductivity in the ERB. The biostructure may be partially resorbable, fully resorbable or nonresorbable. The biostructure may further include one or more of various substances infused into some or all of the porous region.

There are several advantages of the engineered regenerative biostructure over existing granular bone filler materials. Most particulate bone fillers, for example, allograft bone, ceramic hydroxyapatites, bioglasses, and coralline hydroxyapatites, are derived from naturally occurring biologic structures and, consequently, are comprised of a range of microporosities and microstructures that are inconsistent and random. Because both the micro- and meso-architecture or structure of the ERBs can be designed and consistently produced in accordance with principles of the present invention, namely, controlled particle packing with defined inter-particle pores, remarkably good bone in-growth is achievable once with optimal appropriate printing parameters. Under principles of the present invention, controlled, repeatable resorption characteristics and osteoconductivity are achieved.

The engineered regenerative biostructure of the present invention offers the same advantages of off-the shelf bone filler materials, but eliminates variability in tissue response due to the random distributions of pore size and internal structure. The present invention further provides improved durability during shipping and intraoperative handling. Additionally, the ERBs of the present invention provide the advantages of autograft bone without the need to conduct an additional surgery and the necessary healing of a second site where autograft bone is harvested.

The ERB may be a bone augmentation or tissue scaffold biostructure and may contain detailed internal architecture such as microporosity, mesoporosity and/or macroporosity. One method of manufacturing the ERB is by three-dimensional printing process. FIG. 1 illustrates a typical three-dimensional printing apparatus 100 in accordance with the prior art. The apparatus 100 includes a roller 160 for rolling powder from a feed bed 140 onto a build bed 150. Vertical positioners, 142 and 152 position the feed bed 140 and the build bed 150 respectively. Slow axis rails 105,110 provide support for a printhead 130 in the direction of slow axis motion A, and fast axis rail 115 provides support for the printhead 130 in the direction of fast axis motion B. The printhead 130 is mounted on support 135, and dispenses liquid binder 138 onto the build bed 150 to form the three-dimensional object.

In accordance with principles of the present invention, the microporosity includes the interstitial spaces between the sintered or unsintered or bound or unbound particles. Microporosity is the porosity between individual joined powder particles. Mesoporosity is porosity which is larger than microporosity but which does not involve removal of unbound particles. In a form that does not exhibit long-range order or connection, the mesoporosity may include a plurality of micropores. In a form which does include some long-range order or connection or shape, the mesoporosity may take the form of a plane, layer, crack, passageway, internal channel, and the like, which may be irregular and which may have branchings or changes of direction or changes of cross-section, that are conducive to in-growth of natural bone. The mesoporosity may be along a plane or layer that further includes anchor or connection points between the adjacent layers of material so that there is some structural connection between adjacent layers. Macrochannels or other macro features are of a size scale or a large enough number of powder particles such that the unbound powder particles can be removed. The macroporosity or macrostructure may have long, approximately one-dimensional channels or holes that are empty or have reduced packing fraction on a small-size scale to foster the in-growth of natural bone.

The pore size and other feature geometry is designed to be conducive to in-growth of natural bone. The ERB may be made of synthetic materials into which bone grows. The powder particles may be of aspect ratio reasonably close to spherical or equixial, or, alternatively, at least some fraction of the particles may be of somewhat more elongated geometry. The term "particles" is used herein to refer to all of these shapes. In the case of biostructures in which the particles are joined directly to each other, the particles may be made of one or more ceramic or other inorganic substances. Examples of ceramics or other inorganic substances resembling substances found in natural bone are hydroxyapatite, tricalcium phosphate, and other calcium phosphates and compounds containing calcium and phosphorus. The substance may be a sinterable or fusible substance having a sintering or softening or melting temperature. The particles may be polymer(s). Some applications are also described herein, in which the particles include demineralized bone matrix.

The ERB may have an overall exterior shape that includes geometric complexity. For example, the overall exterior shape may include undercuts, recesses, interior voids, and the like, provided that the undercuts, recesses, interior voids, and the like have access to the space outside the biostructure. The ERB may be shaped appropriately so as to replace a particular bone or bones or segments of bones or spaces between bones or voids within bones. Examples of such bones are given herein. The ERB may be dimensioned and shaped uniquely for a particular patient prior to the start of surgery. Alternatively, the ERB of the present invention could be simple overall shapes such as blocks, which are intended to be shaped by a surgeon during a surgical procedure. The ERB may be tightly fitting with respect to a defect in a bone. To aid fit, the ERB may be tapered or beveled or include some other interlocking feature.

The partially joined particles may form a three-dimensionally interconnected network. The space not occupied by the partially joined particles, may also form a three-dimensionally interconnected network that may interlock with the network formed by the partially joined particles. The space is referred to herein as the pores or porosity.

Porosity may be characterized by the porosity fraction or void fraction, which is the fraction of the overall volume that is not occupied by particles or other solid material. The porosity may have a value between 10% and 90%, more preferably between 30% and 70% for partially sintered articles made by three-dimensional printing, and as illustrated below, approximately 50% for the examples herein which were used for in vitro studies.

For an individual particle, an equivalent particle diameter can be defined as the diameter of a sphere having volume equal to that of a particle, and diameters of various particles may be averaged to give an average particle diameter of a collection of particles. The biostructure may be made of powder particles whose average particle diameter is in the range of 10 to 50 microns, and may typically be 20 or 40 microns in diameter. Within a given biostructure, the range of particle diameters may have a maximum. In examples using hydroxyapatite powder, the maximum particle size was 100 microns, but it could be larger than that such as 300 microns. If polymer particles are used, the particle size might be larger even as much as 2000 microns. When such powder particles join in the form of necks, at typical porosities, the average pore size is slightly less than the powder particle size.

Pore size may involve a distribution of pore size. Pore size may be characterized by a pore size distribution which may be measured by mercury porosimetry and which may be presented as a graph of what fraction of the total pore volume is present in pores of a given size or size range, as a function of pore size. There may be one or more peaks in the pore size distribution, and each pore size which is at a peak may be considered to be a statistical mode for pore size, in terms of the fraction of the total pore volume which is contained by a given pore size or pore size interval.

Typically, for a porous biostructure that is produced by simple techniques, there is one peak in this graph (at least when looking at the pore size range of interest such as 0.1 microns to 1000 microns), with a decreasing distribution on either side of the peak, and this may be called a unimodal pore size distribution. The peak may be called the mode pore size (with the word mode being used in the statistical sense). This peak may be at a pore size which is slightly smaller than the average particle diameter, which may be defined as being between one-tenth of the average particle diameter and the average particle diameter. A peak in this size range, whether or not it is the only peak in the pore size distribution, may be defined as referring to microporosity.

In terms of actual dimensions, in the present invention, the peak may be at a pore size such as 6 to 10 microns for powder having an average particle diameter of 20-microns powder, or in the range of 10 to 16 microns for 40-micron powder particles, or more generally anywhere in the range of 5 to 20 microns. This pore size for the peak in the pore size distribution is smaller than what has traditionally been taught in the literature of bone implants as being good for promoting the in-growth of natural bone. One embodiment of the present invention is a porous biostructure with a pore size distribution that is unimodal (at least within the pore size range 1 microns to 100 microns) and that has its peak between 10 and 25 microns. This embodiment of the present invention is referred to herein as isotropic. However, not all embodiments of the present invention are isotropic.

In some embodiments, the ERB may have a designed internal geometric architecture comprising microstructure, mesostructure and macrostructure in the form of interstitial porosity, open holes, passageways or channels of size scale such that the smallest dimension of the hole passageway or channel is approximately equal to or larger than the diameter of the particle used. The microstructure and mesostructure interconnect, and at least some part of the interconnected porosity, holes, passageways or channels has access to the space outside the biostructure.

Figure 2B:
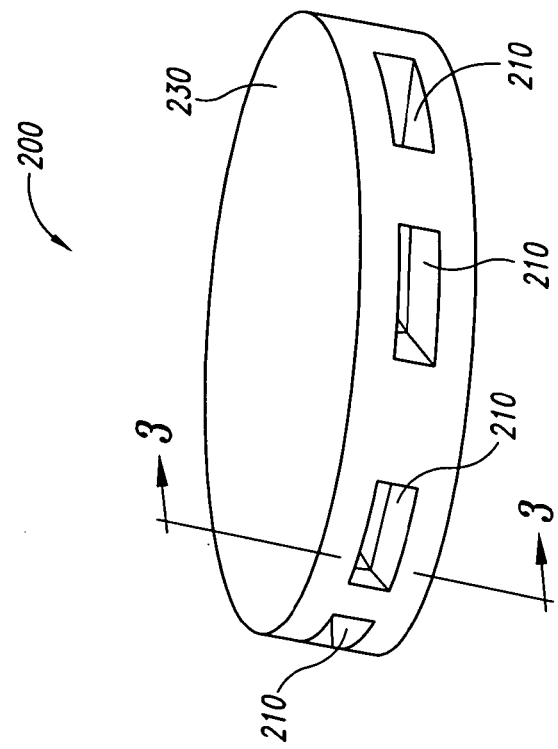
FIGS. 2A, 2B and 2C are one embodiment of an engineered regenerative biostructure in accordance with principles of the present invention.
Figure 2A:
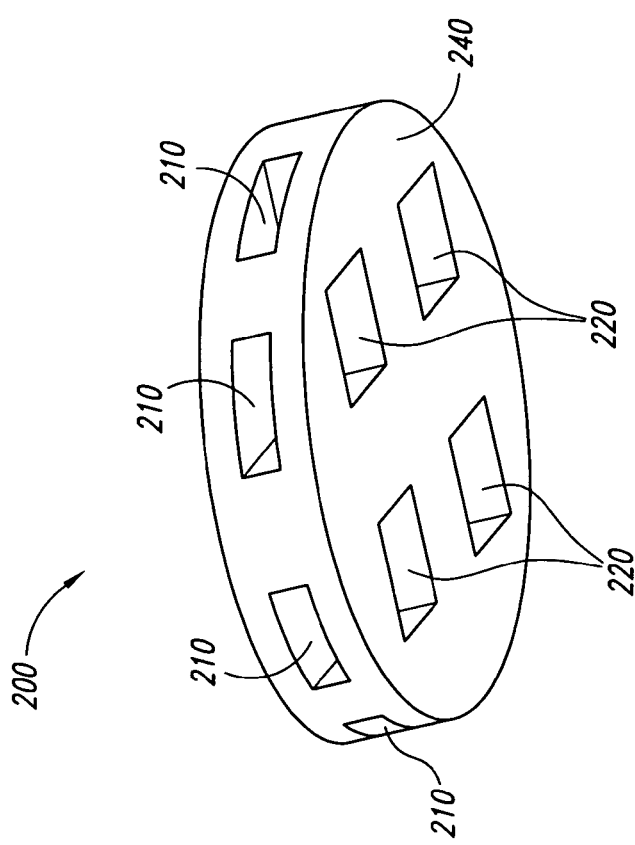

FIGS. 2A and 2B illustrate one embodiment of an engineered regenerative biostructure 200 with an arrangement of macrostructure suitable for use as an implant. It is a biostructure of cylindrical exterior geometry and comprises macrostructures 210 in two different coplanar directions shown here as being horizontal, intersecting each other, and also comprises vertical channels. The horizontal and vertical channels in the present embodiment may be approximately 1.35 mm in height and width. The vertical channels 220 are shown as also intersecting the horizontal channels 210 at places where the various horizontal channels intersect each other. A top region 230 of the illustrated ERB contains no macrostructure. A bottom region 240 includes vertical channels 220 that extend through the ERB and may terminate prior to intersecting with the horizontal channels 230, at the intersection of the horizontal channels 230, or at some point beyond the intersection of the horizontal channels. Furthermore, each of the vertical channels 220 may terminate at a point independent of an adjacent channel. In alternative embodiments, the vertical and horizontal channels may be angled, non-linear, or have varying cross-sectional dimension.

In one embodiment of the present invention, the macrostructure includes holes or passageways or channels that may each have a cross-section that is substantially constant. In an alternative embodiment of the present invention, the cross-section of the holes passageways channels or other macrostructural features may be variable. These holes passageways or channels may be relatively long in one dimension in comparison to their other two dimensions. As illustrated below, the macrostructure provides paths or branches for in-growth of natural bone, cartilage or other tissue. Such holes or passageways or channels need not be straight; they can be curved, have changes of direction, have varying cross-section, and the like, and can branch to form other passageways or channels or holes or can intersect other passageways or channels or holes. Macrostructure channels may range from 2 to 2000 microns and typically range from 200 to 700 microns in size. As a practical matter, if the ERB contains macrostructure channels as described herein, typically the channels are too large to be measured as pores by mercury porosimetry. The minimum cross-sectional dimension of a macro-channel is approximately the cross-sectional dimension of a primitive as explained later.

The dimensions of the macrostructure channels may for example be 1 mm to 1.6 mm in each of the two dimensions in a cross-section perpendicular to the longest direction of the macrostructure. The ERB may, as is shown, have one surface which is parallel to the plane of the horizontal channels and which is essentially continuous, containing no macroscopic holes or channels through it. This continuous surface may be referred to as the top surface, and the surface that has vertical holes or macrostructures through it may be referred to as the bottom surface.

Figure 2C:
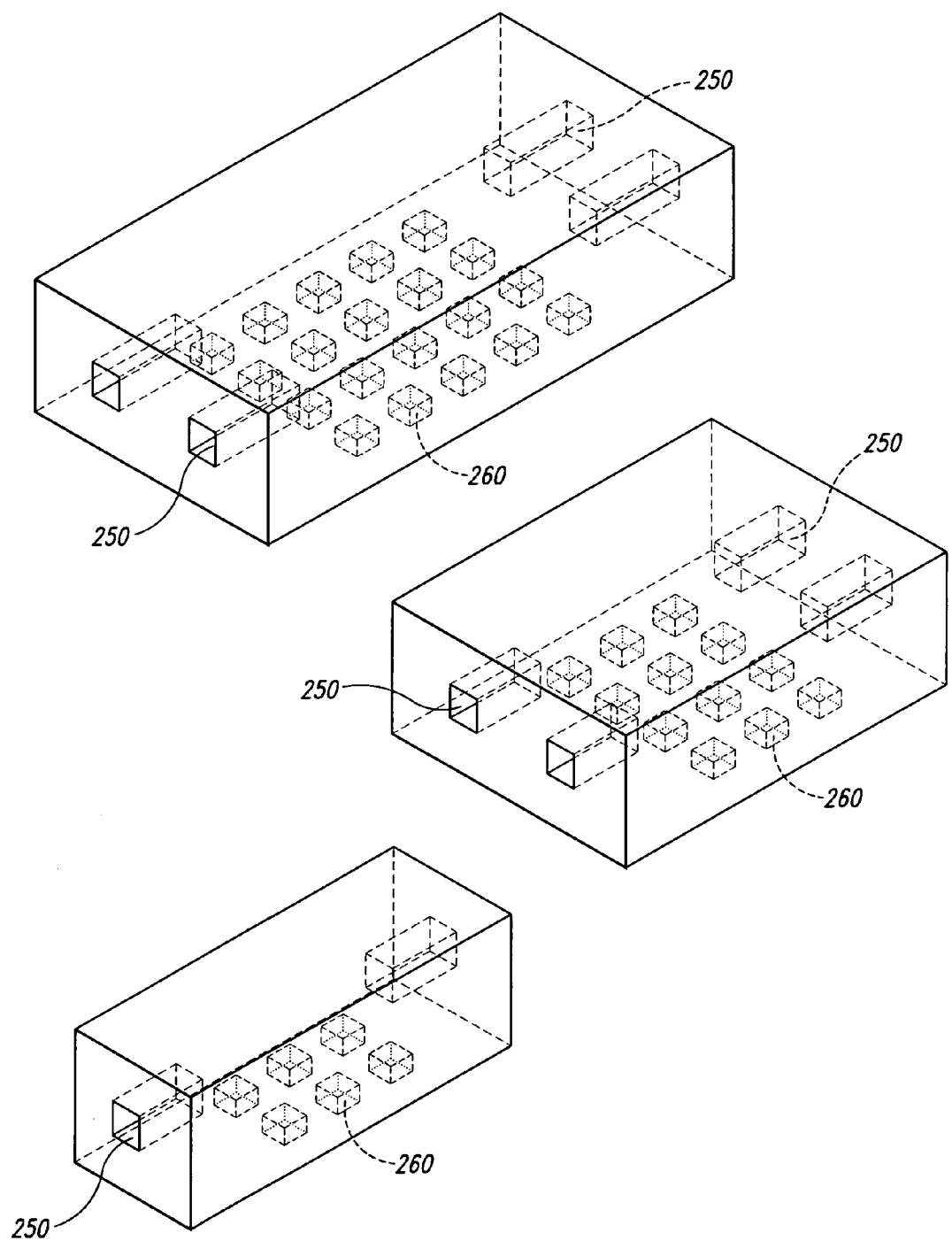

As shown in FIG. 2C, it is possible for the biostructure to have other macroscopic features (of size equal to or greater than the dimension of a primitive) which have a geometry other than that of a channel going all the way through the biostructure. It is, for example, possible to have dead-end channels 250 which do not intersect any other channel or feature. It is possible to have grooves which exist on exterior surfaces of the biostructure. It is possible for the external surface to have dimples 260 or similar features formed on the scale of primitives or larger. All of such geometries may be thought of as resembling, in their geometry and also in their possible variety, the treads of a tire.

When the biostructure is implanted such that at least one surface contacts soft tissue, it may be desirable to include a region, which in FIG. 2B is the top region, that inhibits in-growth of the soft tissue. FIG. 2B illustrates a biostructure 200 with a top region 230 that which, first of all, does not include macrochannels therethrough. In addition, further features may be incorporated to discourage the ingrowth of soft tissue. One embodiment of a surface region that inhibits the growth of soft tissue is a three-dimensionally printed layer wherein several printer layers are printed in a manner which discourages the formation of mesoporosity, as described later. This can include staggered configuration such that the micropores are less than 10 microns. Another s such feature can be a top surface region that includes a coating that is impermeable to the soft tissues. Yet another such feature can be a top surface region that is infused with PMMA or similar material to inhibit soft tissue in-growth. In this embodiment, only the specified region may be infused such that the remaining biostructure is porous to allow bone in-growth.

Figure 3:
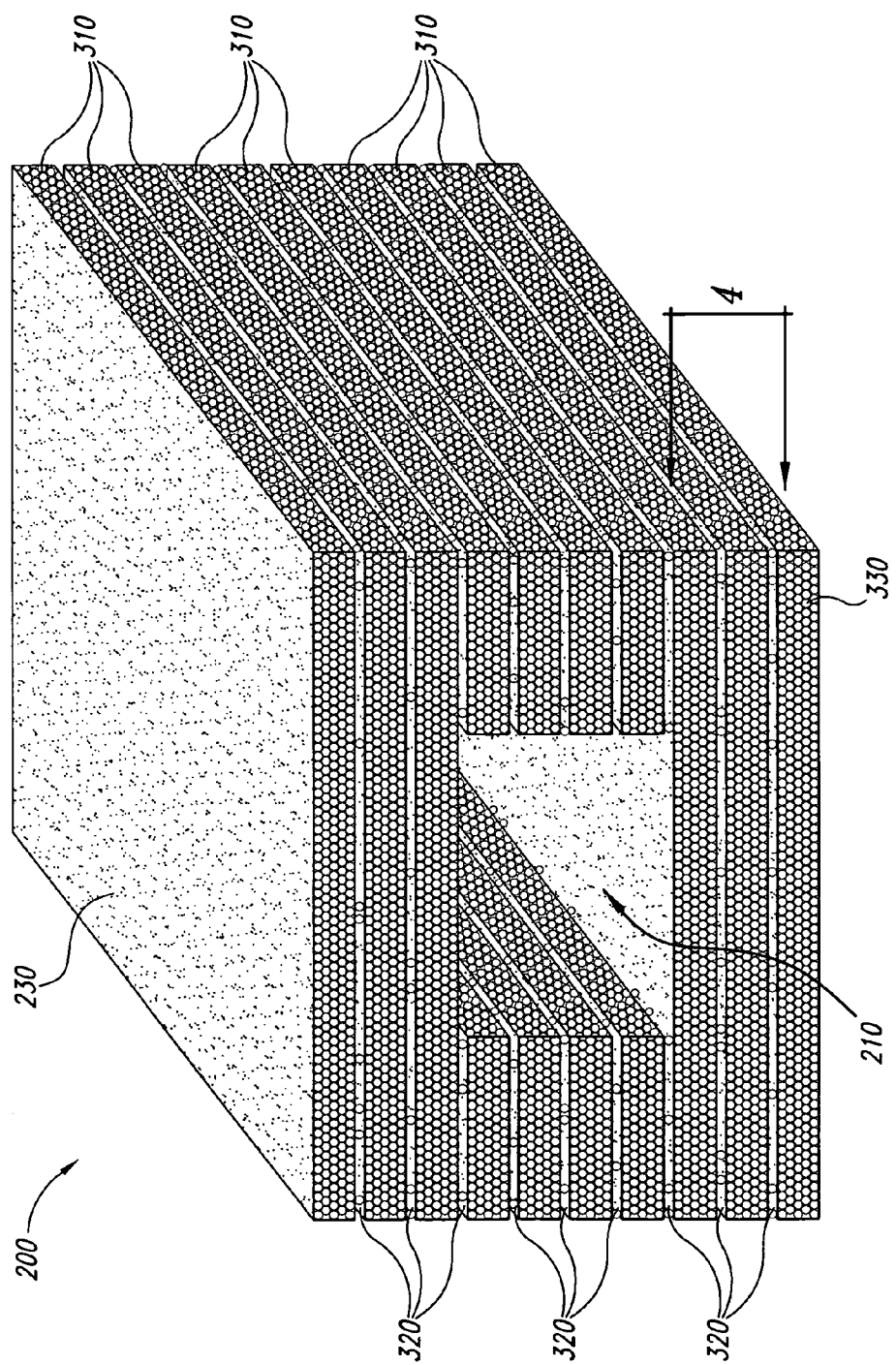
FIG. 3 is a partial cross sectional view of the macrostructure and mesostructure of the engineered regenerative biostructure of FIG. 2 taken along line 3—3 in accordance with principles of the present invention.

FIG. 3 is an enlarged partial cross sectional view of one macrostructure channel of FIG. 2 and further illustrates one embodiment of mesostructure and microstructure in the engineered regenerative biostructure. FIG. 3 illustrates macrostructure, mesostructure and microstructure all in one illustration. In FIG. 3, the biostructure 200 includes the top region 230 and one macrostructure channel 210 from FIG. 2 along line 3—3. The enlarged view further illustrates layers 310 of bound particles. A first layer 310 is anchored at point contact locations to a second layer in region 320. Controlling the connection between the layers 310 controls the configuration of the mesostructure as discussed further herein. Having some connection between layers helps to hold the overall article together and provide some structural strength. However, having incomplete connection between layers is what creates the mesoporosity. Particles 330 of bound powder material are shown in an ideally packed configuration as they might be spread. As shown in FIG. 3, each layer 310 is approximately five powder particles thick. Altering the packing of the particles 330 will change the microporosity or microstructure.

Figure 4:
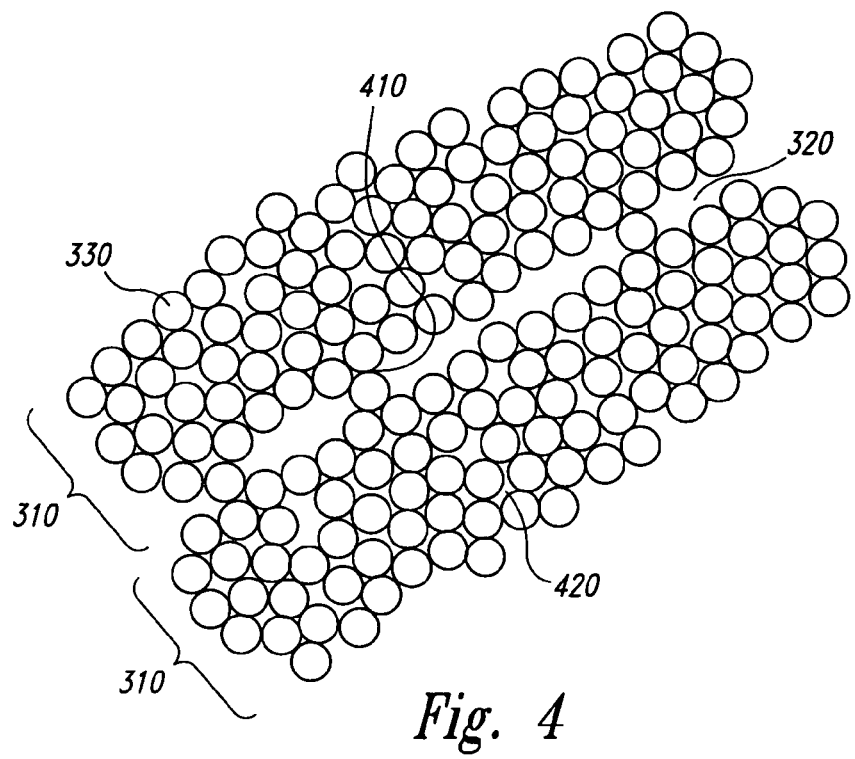
FIG. 4 is an enlarged cross sectional view of the mesostructure of FIG. 3 taken along line 4—4 in accordance with principles of the present invention.

FIG. 4 is an enlarged cross sectional view of the mesostructure of FIG. 3 taken along line 4—4. Layers 310 are made up of individual particles 330. The layers are interconnected or anchored to the adjacent layer at point contact locations 410. Microstructure 420 is illustrated as voids or interstitial spaces between particles. Mesostructure 320 is regions which are empty or of reduced packing density on a size scale somewhat larger than the size scale of micropores or microstructure. Mesostructure 320 is shown as an exemplary interconnected void layer between particle layers 310 which contains point contacts between a first particle layer and a second particle layer. In FIG. 3, in which the mesostructure is layer-like, the macro-channels are parallel to the plane of the mesostructure.

Thus, in embodiments which contain mesostructure, the biostructure contains internal architecture that is locally empty, and that is on a smaller size scale than the macrostructures but on a size scale larger than microporosity. Mesostructure provides additional regions for bone in-growth and is conducive to in-growth of natural bone. Mesostructure may be features in which powder particles are absent for a distance in one dimension that is smaller than the dimension of a macrostructure channel, in which case these features may be essentially open space (zero packing fraction). Mesostructure may be generally in a layer shape or may alternatively form a variety of shapes such as regions which are corners where primitives come near each other and which may have curves outlines such as a four-pointed star or similar crescent shape.

Mesostructure may have irregular boundaries, but despite irregularity of boundaries some dimensions of open regions can still be identified. For an individual particle, an equivalent particle diameter can be defined as the diameter of a sphere having volume equal to that of a particle, and diameters of various particles may be averaged to give an average particle diameter of a collection of particles. Any particle on the boundary of a mesostructure has an opposite wall or similar surface which can define a nearest facing particle which is not closely connected to the particle of interest, for example, may be defined as being at least 5 powder particles away from the particle of interest along a path through particles which are joined to one another.

In the mesostructure or mesoporosity, the separation distance from a particle of interest to that nearest facing particle may be considered to be at least one powder particle diameter, and a range for such separation distance may be considered to be between 1 and 20 particle diameters. This is considered to be the smallest dimension of the three dimensions of the mesostructure. An empty region which constitutes a mesostructure can also be defined as having a greatest dimension which is a length from end to end of the mesostructure. An end of a mesostructure can be either a dead-end, where the mesostructure ends by meeting completely joined powder particles, or can be a place where a mesostructure reaches the surface of the biostructure. An end can also be defined as where a mesostructure meets a branching.

The mesostructure may have two such ends and a path between the two ends, measured along a path that generally follows the overall shape of the mesostructure. The overall path of the mesostructure along its largest dimension may be either approximately straight (approximately, in view of the small-scale irregularity inherent in a mesostructure), or it may be curved or of other arbitrary shape.

Figure 5:
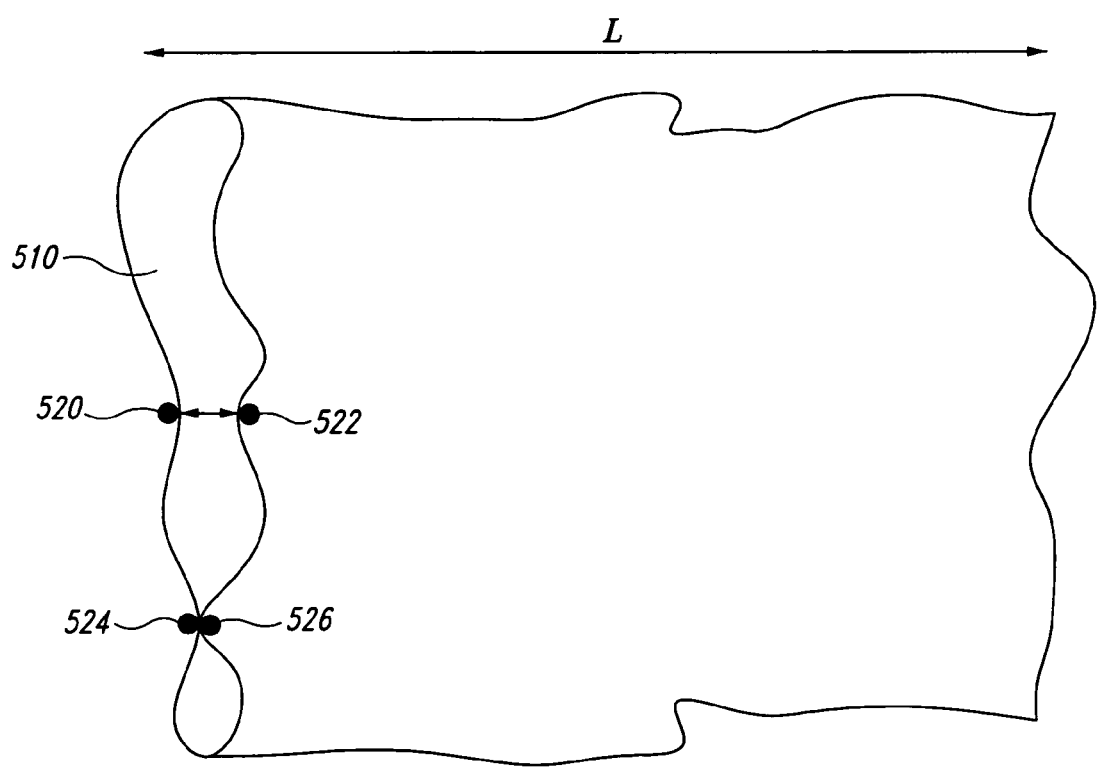
FIG. 5 is an isometric view of a mesostructure in accordance with principles of the present invention.

FIG. 5 is another illustration of mesostructure within the biostructure. The mesostructure 510 is shown as interconnected interstitial spaces between powder particles 520 and 522. Interconnected powder particles 524 and 526 are sintered or otherwise connected to one another such that the layers of particles surrounding the mesostructure are affixed to one another. The length of the biostructure L represents the largest length available for the mesostructure. In actual dimensions, typical ranges of dimension for a mesostructure may be a smallest dimension of 20 microns to 100 microns, and a largest dimension which can be as long as the length of the manufactured article. However, mesostructure is also described later herein which does not have to be long in any direction.

Articles that contain porosity including mesostructures can also be characterized by their pore size distribution. Structures containing mesostructures typically exhibit a bimodal pore size distribution, with one peak or mode pertaining to the pore size which exists between particles that are partially bonded to each other in a manner resembling that of the isotropic material previously described, and another peak or mode pertaining to the dimension of the cracks or mesostructures.

It is also possible to have features which are of the nature of mesostructures as already described, but have a packing fraction which is not strictly zero but is smaller than that of the more tightly packed regions which surround the mesostructure. These regions may contain powder particles that are bound to each other at a relatively smaller local packing density, compared to other parts of the biostructure. These regions of relatively smaller local packing density may be long in one direction and small in another direction as just described for mesostructures. The localized packing density used in describing these features may be defined as being for a region whose overall dimensions are all approximately several to five times the dimension of a powder particle. It is also possible to have mesostructures which exist at the surface of a manufactured article and contribute to the surface irregularity, which may help to promote the in-growth of bone.

Still another possibility is that the locally empty regions may contain some particles or small groups of particles that are not bound to any other particle but rather are trapped between particles that are bound together. All of these possibilities are included in the present invention. All of these can be described by a pore size distribution. The pore size distribution of these situations such as mesostructures which are not completely empty or which even contain occasional loose particles would typically also be bimodal but the details of the shape might be different from the pore size distribution for a mesostructure whose interior is truly empty.

In the present invention with a bimodal distribution, one mode or peak may correspond to the size of pores that exist between partially joined powder particles. The pore size for this mode may be in the range of 10 microns to 25 microns. More generally, the pore size for this mode may be in the range of one-third to 1.5 times the average powder particle diameter. Although this pore size is smaller than typically taught for bone in-growth, in accordance with principles of the present invention, this pore size actually helps to promote the in-growth of natural bone. The other mode or peak may correspond to the dimensions of mesostructures. Either peak may be the larger of the two peaks. For the articles tested herein, the smaller-pore-size peak is the larger of the two peaks.

It is possible that the biostructure of the present invention may contain only microstructures or mesostructures without containing macrostructures. It is possible that the biostructure of the present invention may contain only microstructures without either mesostructures or macrostructures. Further, mesostructures may branch off of other mesostructures. Macrostructures could branch off of other macrostructure channels.

It is possible that the biostructure may contain both macrostructure channels and mesostructures. In such a biostructure, mesostructures may branch off of other mesostructures, and macrostructure channels could branch off of other macrostructure channels, and mesostructures may be branches from macrostructures. It is possible that some portions of the biostructure may comprise mesostructures while other portions of the biostructure may have uniform packing density of powder particles and joining of particles to each other, i.e., not have mesostructures but have microstructures. Either one of such regions or both of such regions could still comprise macrostructure channels or they do not have to comprise macrostructure channels.

Three Dimensional Printing Aspects of Manufacturing the Engineered Regenerative Biostructure Three-dimensional printing (3DP), described in U.S. Pat. No. 5,204,055, is one method of creating complex geometries in medical devices. Three-dimensional printing is found also described in U.S. Pat. No. 5,370,692. A typical three-dimensional printing apparatus is illustrated in FIG. 1.

Three-dimensional printing has been proposed for creating a variety of three dimensional medical devices, pharmaceuticals and implants, however, the prior methods of creating a device did not teach or disclose engineered microstructures, mesostructures or macrostructure channels.

The biostructure of the present invention may be manufactured by three-dimensional printing followed, in certain embodiments, by appropriate post-processing steps. Three-dimensional printing allows the manufacture of biostructures of great geometric internal and external complexity including recesses, undercuts, internal voids and other geometric features, which are difficult or impossible to create with conventional manufacturing processes. Three-dimensional printing also allows the creation of compositional variation within the biostructure that may not be achieved by conventional manufacturing processes.

In three-dimensional printing, a layer of powder is deposited such as by roller spreading. Examples of the powder substance are described herein. After the powder layer has been deposited, a binder liquid is deposited onto the powder layer in selected places so as to bind powder particles to each other and to already-solidified regions. The binder liquid may be dispensed in the form of successive discrete drops, a continuous jet, or other form.

Binding may occur either due to deposition of an additional solid substance by the binder liquid, or due to dissolution of the powder particles or of a substance mixed in with the powder particles by the binder liquid, followed by resolidification. Following the printing of the binder liquid onto a particular layer, another layer of powder is deposited and the process is repeated for successive layers until the desired three-dimensional object is created. Unbound powder supports bound regions until the biostructure is sufficiently dry, and then the unbound powder is removed. Another suitable method that could be used to deposit layers of powder is slurry deposition.

The liquid thus deposited in a given pass binds powder particles together so as to form in the powder bed a line of bound material that has dimensions of bound material in a cross-section perpendicular to the dispenser's direction of motion. This structure of bound powder particles may be referred to as a primitive. The cross-sectional dimension or line width of the primitive is related in part to the diameter of the drops if the liquid is dispensed by the dispenser in the form of discrete drops, or to the diameter of the jet if the liquid is deposited as a jet, and also is related to other variables such as the speed of motion of the printhead. The cross-sectional dimension of the primitive is useful in setting other parameters for printing.

For printing of multiple adjacent lines, the line-to-line spacing may be selected in relation to the width of the primitive printed line. Also typically the thickness of the deposited powder layer may be selected in relation to the dimension of the primitive printed line. Typical drop diameters may be in the tens of microns, or, for less-demanding applications, hundreds of microns. Typical primitive dimensions may be somewhat larger than the drop diameter.

Printing is also described by a quantity called the saturation parameter. Parameters which influence printing may include flow rate of binder liquid, drop size, drop-to-drop spacing, line-to-line spacing, layer thickness, powder packing fraction, etc., and may be summarized as a quantity called the saturation parameter. If printing is performed with discrete drops, each drop is associated with a voxel (unit volume) of powder that may be considered to have the shape of a rectangular prism.

Figure 6:
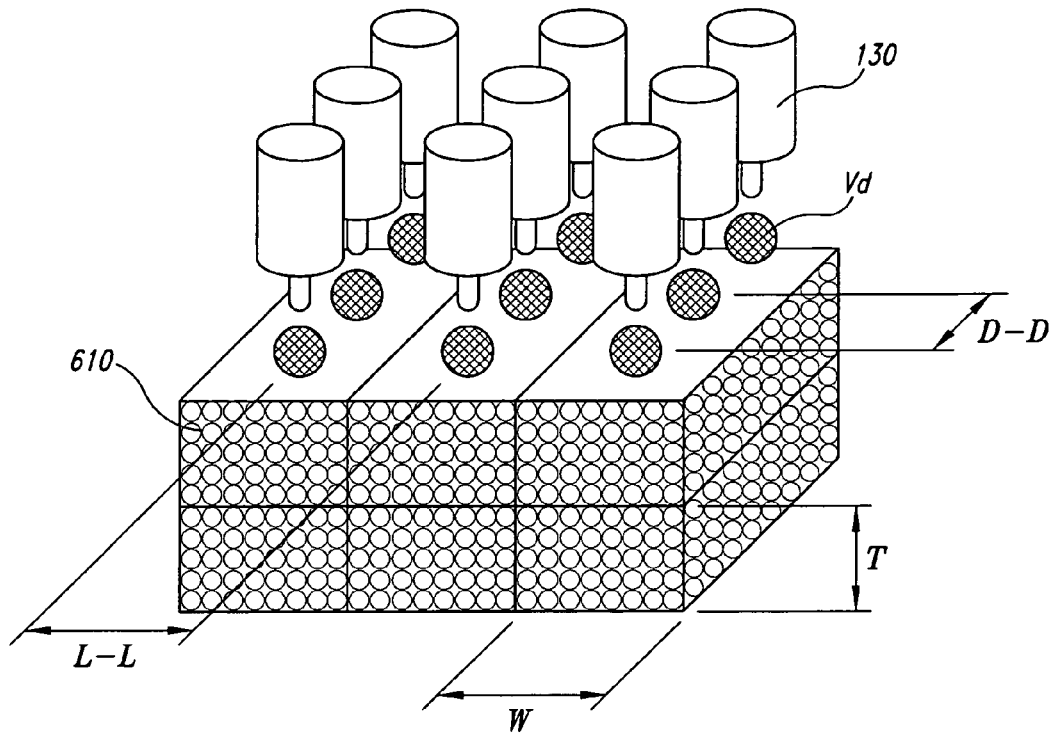
FIG. 6 is an isometric view of a printhead, binder droplet and powder layer in accordance with principles of the present invention.

As shown in FIG. 6, the dimensions of the voxel 610 are the drop-to-drop spacing D—D, the line-to-line spacing L—L, and the thickness T of the powder layer. The horizontal dimension of the voxel in cross-section is shown as W and is equal to L—L. The voxel contains within it a total volume given by (delta x)*(delta y)*(delta z). It also contains a certain amount of empty volume representing the space between powder particles, i.e., space not occupied by powder particles, given by (1−pf)*(delta x)*(delta y)*(delta z).

The ratio of the dispensed droplet volume to the empty volume in the voxel is the saturation parameter. The illustrated voxel has dimensions delta x, delta y and delta z, and has a powder packing fraction pf. The printhead fast axis speed and dispense interval may be given by V and delta T with the relation that (delta x)=V*(delta t). The drop volume may be represented by Vd. In this situation, the available empty volume in the voxel is given by (1−pf)*(delta x)*(delta y)*(delta z). The saturation parameter is given by $$Vd/((1-pf)*(\text{delta x})*(\text{delta y})*(\text{delta z})).$$

FIGS. 7A–7D are a schematic illustration of process steps for forming a macrostructure in an engineered regenerative biostructure in accordance with one embodiment of the present invention. Some of the steps pertain to making macrostructure in any 3DP process, and one step is particular to making macrostructure in materials which are sinterable.

Figure 7A:
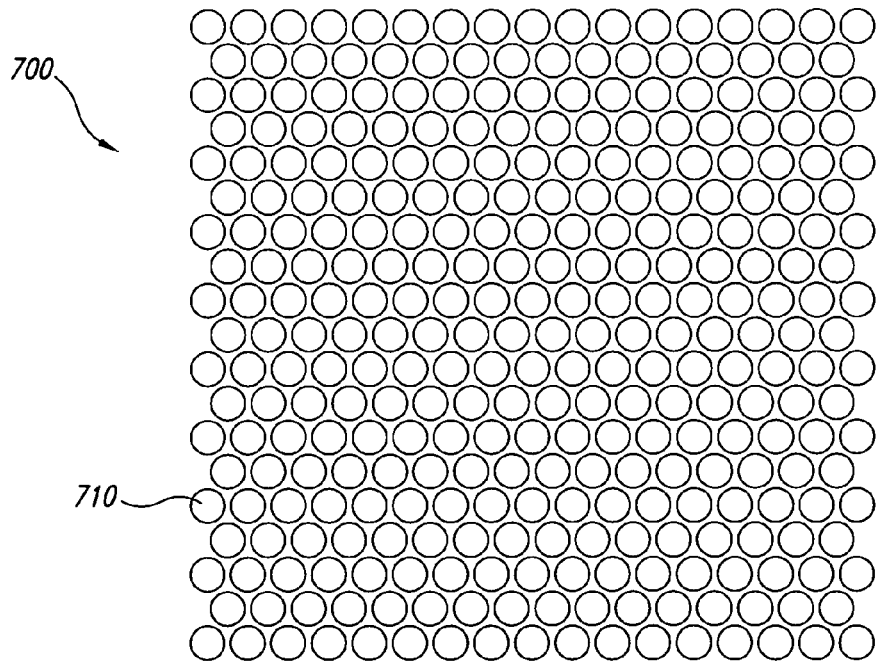
FIGS. 7A–7D are a schematic illustration of process steps for forming a macrostructure in an engineered regenerative biostructure in accordance with principles of the present invention.

A macrostructure such as a macro-channel may be made by printing bound regions so as to define a region of unbound powder by surrounding it with bound regions from all but at least one direction. A macrochannel may have a minimum dimension which is approximately the size of one primitive. FIG. 7A illustrates a cross-sectional representation of a bed 700 of particle powder 710 without binder deposition. For simplicity, the powder particles are shown as all being spherical of identical diameter. The powder bed is shown as having a packing density which is everywhere the same, having some degree of looseness in the way the particles rest upon each other.

Figure 7B:
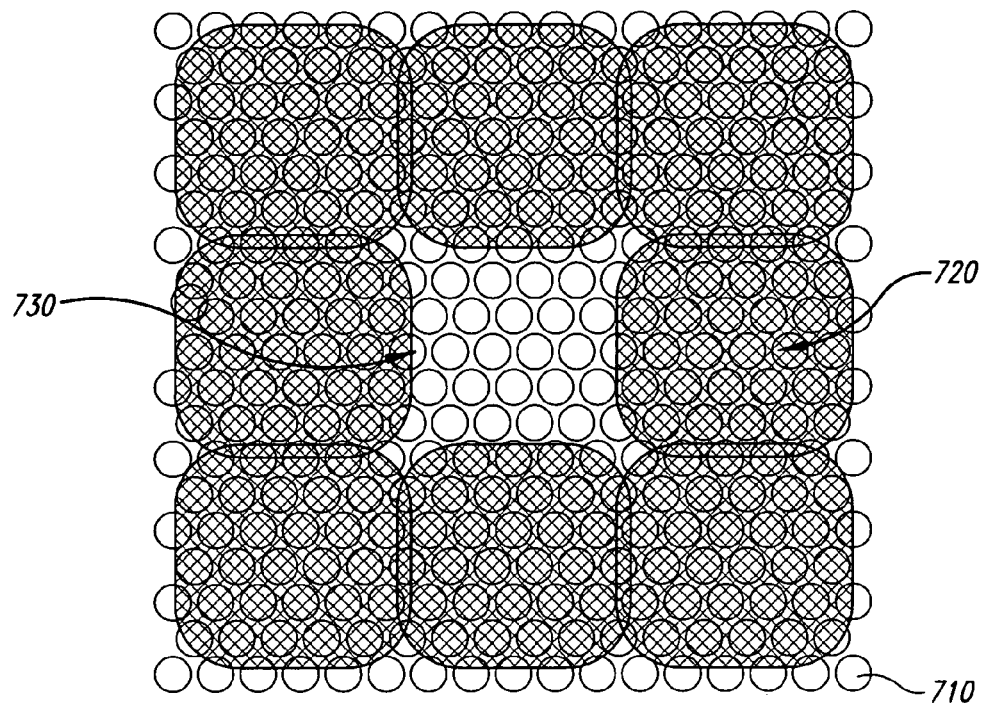
Figure 7C:
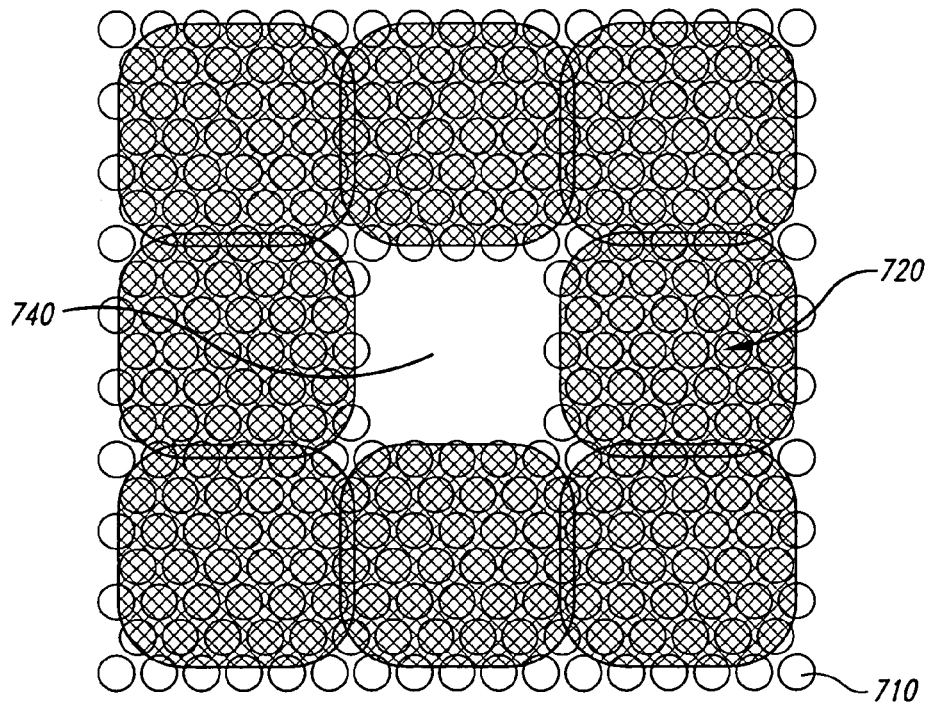
Figure 7D:
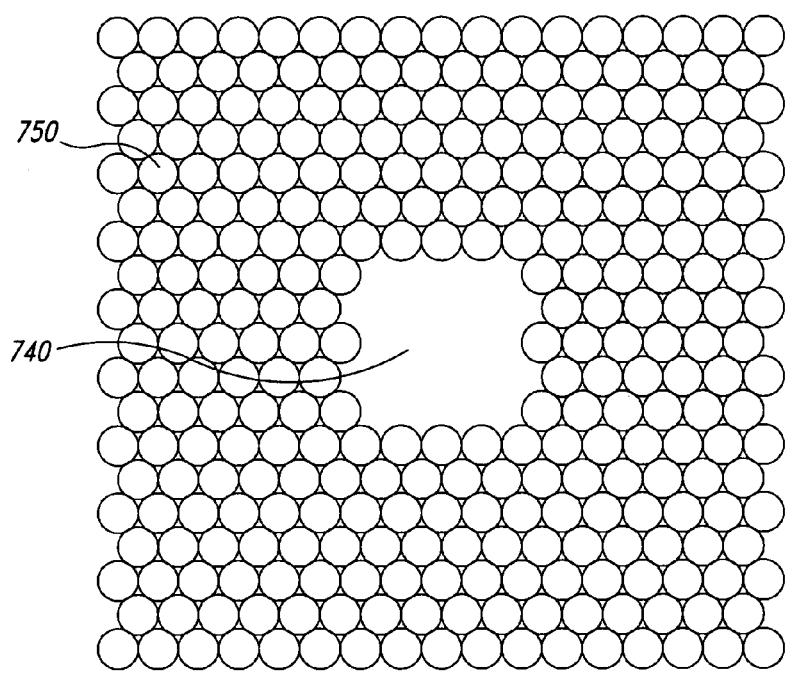

FIG. 7B illustrates a cross-sectional view of binder drops 720 printed on the layer 700 of particle powder 710. The binder is of sufficient saturation to achieve filling of each individual primitive with binder liquid. The binder drops 720 are printed in a pattern to allow some space 730 between primitivesto remain unprinted and therefore unbound. FIG. 7C illustrates the binder substance 720 remaining in the powder bed 700 after the volatile part of the binder liquid has evaporated, and further illustrates that. The unbound powder 730 has been removed such that a channel or void 740 remains. If the powder substance is not suitable for sintering, the configuration shown in FIG. 7C may be the finished product. If the powder substance is suitable for sintering, FIG. 7D illustrates a cross-sectional view of the same article with the binder substance removed such as through decomposition (burnout) and the particles joined directly to each other such as through partial sintering. The shape of the region where unbound particles were removed remains as a macro-channel. macrochannel or void 740. Although the illustration refers primarily to its views as a cross-section, similar view could be made in the vertical direction looking at the powder layer, for building a macro-channel in the vertical direction.

Typically, in three-dimensional printing, if complete or nearly complete line-to-line and layer-to-layer binding is desired without excessive spreading of liquid, a saturation parameter approximately or slightly less than unity is used, for printing performed at room temperature. A larger saturation parameter would be used if externally applied heat such as inter-layer drying is used. This saturation parameter would be used to provide macrostructures and to eliminate or minimize mesostructures.

In printing macrostructures, the at least one direction in which the unbound powder is not surrounded by bound powder provides access by which unbound powder can be removed after completion of three-dimensional printing. After drying of the three-dimensional printing biostructure, removal of unbound particles may first be done by simple methods such as gentle shaking or brushing, and further removal of powder from the interior of macrostructures may be aided by the use of sonication in liquid or other techniques such as are known in the art. Macrostructures made by three-dimensional printing may include changes of direction, changes of cross-section, branchings, and the like.

There are also other possible ways of making a macrostructure. One such method involves double-printing, i.e., printing on a layer of powder, allowing the volatile part of the binder liquid to evaporate essentially completely, and printing more binder liquid onto the same place such that the binder substance which remains after the last printing is built up above the actual powder particles in the bed. The next layer of powder which is spread or deposited cannot occupy the region which is occupied by the built-up binder substance from the "puddle" formed by the repeat printing(s) at the same location. Eventually, when the binder material in the puddle decomposes and exits as gaseous decomposition products, the absence of particles in the region formerly occupied by the puddle yields a macrostructure of empty space. Yet another possible method of making a macrostructure involves the chemical change of the composition of the powder particles which is described elsewhere herein. A second binder fluid (not shown) that is chemically reactive may be printed in the region of the macrochannel such that the macrostructure is formed after burnout of the binder substance and chemical reaction of the particles with the chemically reactive binder such that the reaction product is soluble such as in water, as described elsewhere herein. Then, material in the macrochannel region may be dissolved or leached out to leave an open macrochannel.

Another type of structure that may be part of the present invention is mesostructures. FIGS. 8A–8D are a schematic illustration of process steps for one method for forming a mesostructure in an engineered regenerative biostructure. Some of the steps described in FIG. 8 pertain to making mesostructure in any 3DP process, and one step is particular to making mesostructure in materials which are sinterable. Typically mesostructures are places where bound primitives that may be parallel to each other touch each other and join to some extent but also leave some unbound or partially bound regions such as at corner regions where several primitives are in close proximity, or between layers. The space between those primitives is smaller than the dimension of a primitive. Because the unbound powder region is so small and may be long in the direction through which unbound powder could possibly be removed, powder in that region which has not been wetted by binder liquid and hence has not been bound may remain in the final biostructure. However, such unwetted powder that is left in place may be locally rearranged by the existence and motion of the boundaries of the regions wetted by the binder liquid, and powder which is wetted by the binder liquid may be locally rearranged by the existence and motion of the boundaries of the regions wetted by the binder liquid.

Figure 8A:
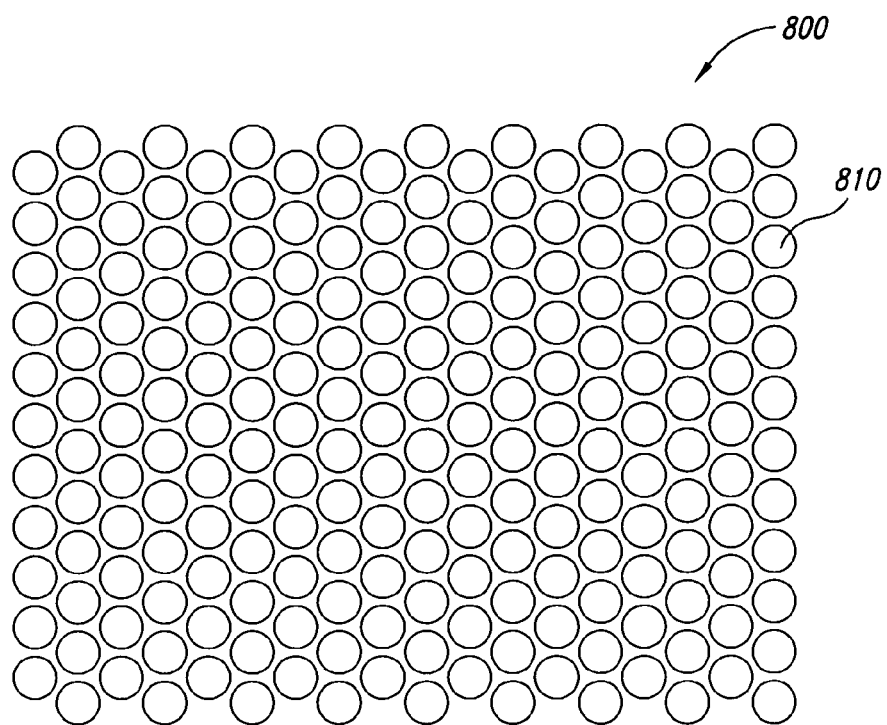
FIGS. 8A–8D are a schematic illustration of process steps for forming a mesostructure in an engineered regenerative biostructure in accordance with principles of the present invention.
Figure 8B:
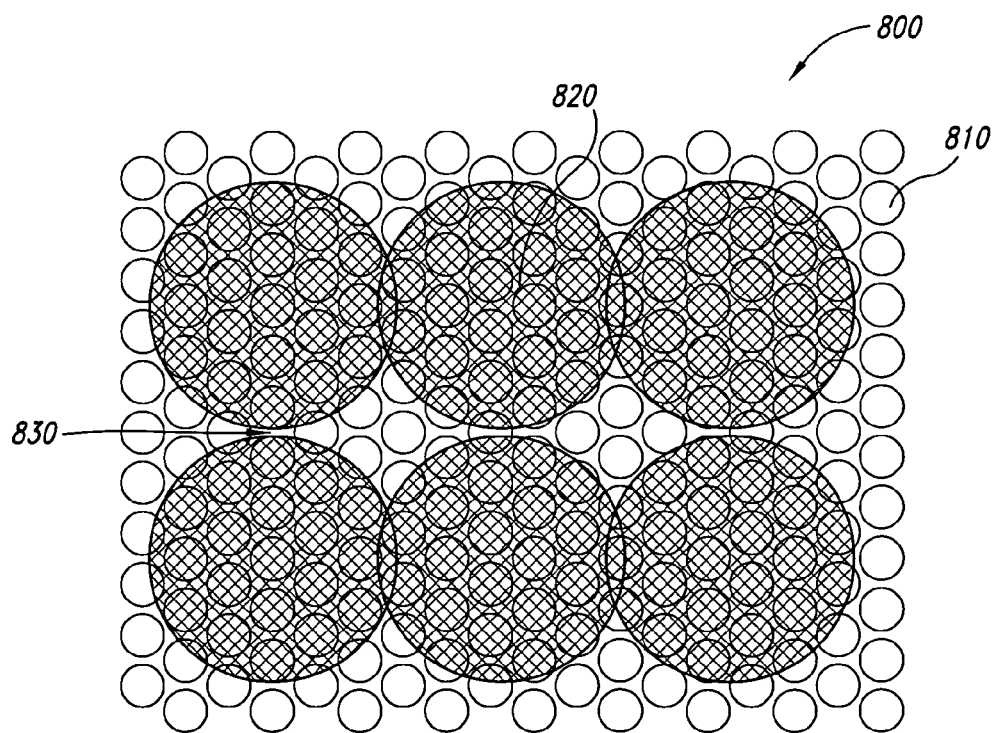

FIG. 8A illustrates a cross-sectional view of a representation of a powder bed 800 of powder particles 810 without any deposition of binder liquid. FIG. 8B illustrates a cross-sectional view of binder drops 820 printed on the bed 800 of powder particles 810. The binder drops 820 are not of sufficient saturation to completely saturate the powder bed to the extent that the primitives completely join each other. Alternatively, the binder drops 820 may be printed in a pattern to allow space 830 between the printed drops to remain partially or completely unprinted and therefore partially or completely unbound 830.

Figure 8C:
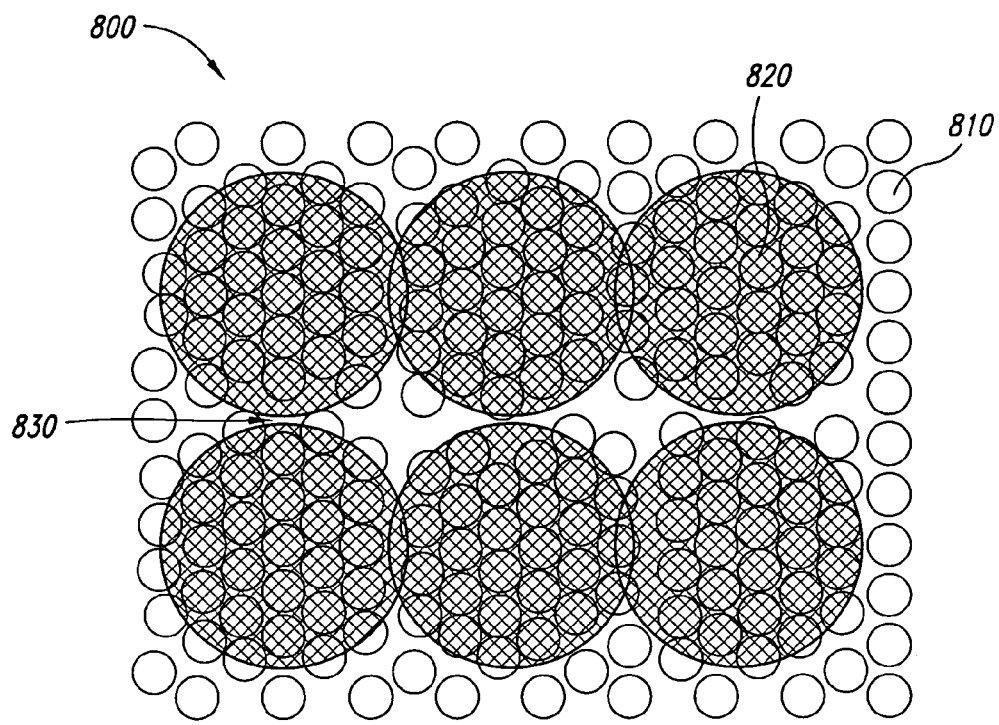
Figure 8D:
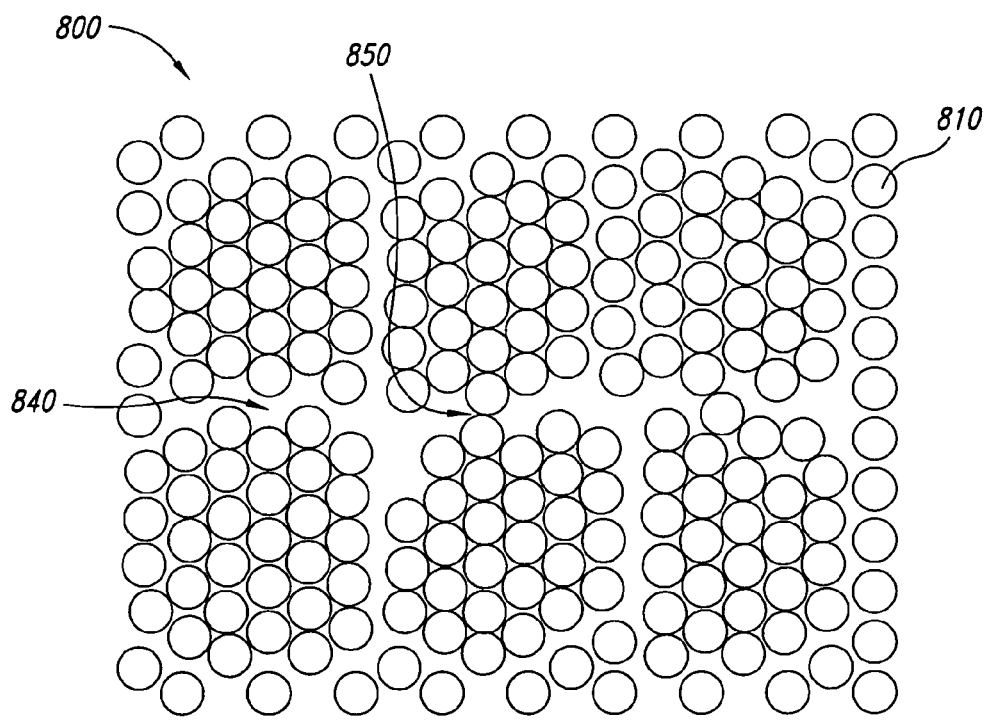

FIG. 8C illustrates the region where binder drops 820 had been deposited, after evaporation of the volatile part of the binder liquid. The drying of the binder drops 820 may cause the powder particles 810 to rearrange and cluster as shown. The deposited binder fluid may pull particles together somewhat within the primitive, resulting in a slightly increased local packing density within the primitives, and further resulting in either empty space or a decreased local packing density in the spaces between the primitives. This rearrangement of particles is accentuated as the liquid dries and the wetted region contracts, and the particles within the wetted region are pulled together, thereby creating a greater unbound region 830 and/or a region of less dense packing of particles. FIG. 8D illustrates that a mesostructure 840 remains. If the biostructure is subjected to a heat treatment so as to partially sinter the particles together, the rearranged configuration of particles still persists and is evident in the final partially sintered configuration. Additionally, affixation points or anchor points 850 remaining after or formed during sintering within the mesostructure provide greater structural integrity to the overall biostructure.

The creation of mesostructures can include appropriate selection of printing parameters. Values of saturation parameter that are significantly smaller than unity can result in incomplete line-to-line or layer-to-layer binding. In industrial three-dimensional printing applications, the existence of incompletely connected primitives (referred to herein as mesostructures) is generally considered undesirable because it may cause a reduction in mechanical strength. However, according to principles of the present invention, mesostructures are designed into the biostructure to provide a path for bone in-growth. One method of designing a mesostructure into a biostructure when manufacturing by three-dimensional printing, is through selection of the saturation parameter, such as less than approximately 60% for printing performed at room temperature, so as to result in incomplete merging of adjacent primitives and hence the production of mesostructures in the three-dimensional printing printed biostructure. When printing is performed with the use of interlayer drying, saturation parameters as large as 120% may be required to achieve the same thing.

During partial sintering, at places where particles initially touch such as with very small areas of contact, the extent of contact increases and the particles join to each other by connecting regions called necks that are smaller than the particles themselves. The size of the necks and the extent of joining may be controlled by the temperature and duration of sintering. Although it is not generally used in the present invention, the extent of sintering may also be influenced by the possible application of external pressure in cases where a large amount of particle joining is desired. In a partial sintering operation as described here, the configuration of powder particles, revealing the primitives and the mesostructures, still persists after the partial sintering operation, and is apparent in the finished product.

A binder substance is a substance that is capable of binding powder particles to each other and to other solid regions. It may be absent from the finished biostructure of the present invention but may be used during manufacture. An example of a binder substance is poly acrylic acid (PM), which can be contained in an aqueous solution. Other examples are other soluble polymers and in general any substance which is soluble in a liquid. The binder substance in the present invention, for inorganic solid materials, may be a substance that is capable of being decomposed by heat at a decomposition temperature so as to form gaseous decomposition products. The gaseous decomposition products, being gases, may easily leave the biostructure. It is also possible, in the case where powder particles are polymers, to use a binder liquid which is itself a solvent for the solid, which will effect partial fusion of particles to each other by partial dissolution of particles followed by resolidification, without leaving any additional substance in the article. Such an example is PLGA particles with chloroform as a binder liquid.

Following the completion of three-dimensional printing and allowing sufficient time for the liquid in the binder liquid to evaporate, the printed biostructure may be removed from the powder bed and unbound powder may be separated from it. This may be done by a simple process such as gentle shaking or brushing and may be further aided by techniques such as sonication such as are known in the art. At this point, the particles that are bound together may be held together by the binder substance, which may have solidified so as to surround or partially surround particles.

If it is intended that the particles in the finished biostructure be partially sintered or fully sintered together, so that the particles join directly to each other, a next step may be heating the biostructure to an appropriate binder decomposition temperature for an appropriate length of time suitable to convert the binder substance into gaseous decomposition products, followed by heating to a sintering temperature for an appropriate length of time. An appropriate decomposition treatment for polymeric binder substances is 400 C for 1 hour. An appropriate treatment for partial sintering of substances such as the mentioned ceramics in the present examples is at a temperature of 1350 C or 1400 C for one to two hours.

In general, organic substances and polymers have decomposition temperatures in the range of several hundred degrees C, while ceramics have sintering temperatures over 1000 C. Thus, the binder decomposition temperature may be well below the sintering temperature, in which case binder substance will not be present in the partially sintered biostructure. The temperature profiles for binder burnout and for sintering need not be step functions, and can involve gradual heat up and/or cool down, and they can be combined with each other to form a combined temperature profile if desired. The time and temperature for sintering may be selected so that the particles join to each other to the degree desired, joining sufficiently to provide the biostructure with mechanical integrity and desired strength, but still remaining incompletely joined so that there is also porosity remaining within the biostructure.

During partial sintering, both the particles that were bound together by binder and any particles that were not bound together by binder but may have been trapped such as within mesostructures, may partially sinter together. In so doing, they may preserve the rearrangement of particles that is believed to have taken place due to the fact of some regions being wetted and other regions not being wetted. Thus, the non-uniform spatial distribution of particles created due to the pattern of binder presence is preserved and made permanent by partial sintering. It is also possible that some powder particles, such as in the unbound region, may fail to sinter but may remain in the finished biostructure where they are, surrounded by and trapped by particles which have partially sintered to each other.

Figure 9A:
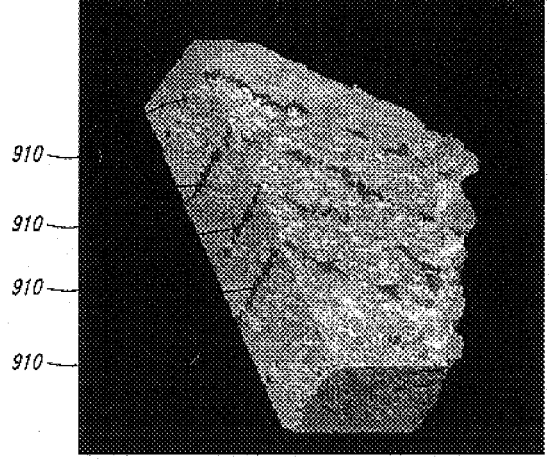
FIGS. 9A and 9B are isometric views of an engineered regenerative biostructure with mesostructure in accordance with principles of the present invention.
Figure 9B:
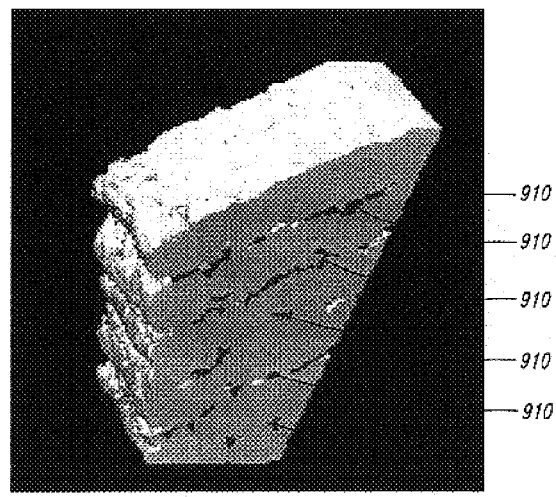

FIGS. 9A and 9B are isometric images of an actual ERB with mesostructure 910 in accordance with principles of the present invention using ceramic (hydroxyapatite) particles with partial sintering. These images were obtained by micro-CT. Micro-CT is obtained by X-raying from various angles and mathematically resolving internal features by solution of simultaneous equations as in a CAT-scan, but the size of the sample is considerably smaller as is the feature resolution. The images presented in FIGS. 9A and 9B are mathematical sections of a mathematical representation obtained by computerized tomography. The average particle size used in manufacturing the samples for these micro-CT images was 20 microns, which is different from the average particle size used in manufacturing the samples for the in-vivo study presented later herein.

There is a range of saturation parameters that is suitable to produce the mesostructures described herein. If the saturation parameter is larger than a certain value it will result in essentially complete binding of primitives to each other. This typically results in the best attainable mechanical strength and is typically a desired situation in the manufacture of industrial or commercial articles by three-dimensional printing. At room temperature, a value of saturation parameter appropriate for producing essentially fully bound primitives may be estimated as approximately 80% or larger when printing is performed at room temperature, without the use of interlayer drying. If mesostructures are desired, a value of saturation parameter smaller than this may be used. For example, at room temperature, a saturation parameter of approximately 60% is a saturation parameter that could be used in the manufacture of biostructures containing mesostructures. If the saturation parameter is too small, such as less than approximately 50%, then little or no joining of primitives to adjacent primitives occurs. There is little mechanical strength in the resulting biostructure and it is possible for primitives to detach from each other relatively easily, with the result that the entire biostructure may delaminate. Printing may be performed with the use of interlayer drying, resulting in an increase in the required value of saturation parameter for any desired result. Biostructures containing mesostructure have been printed using interlayer drying at a saturation parameter of 115% to 120%, but this gives the same result as a smaller value at room temperature.

Figure 10:
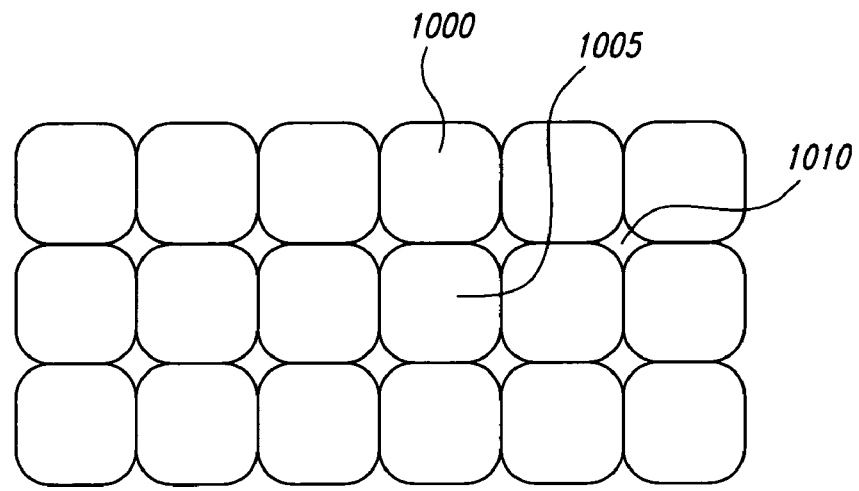
FIG. 10 is a schematic view of a stacked binder deposition configuration in accordance with principles of the present invention.
Figure 11:
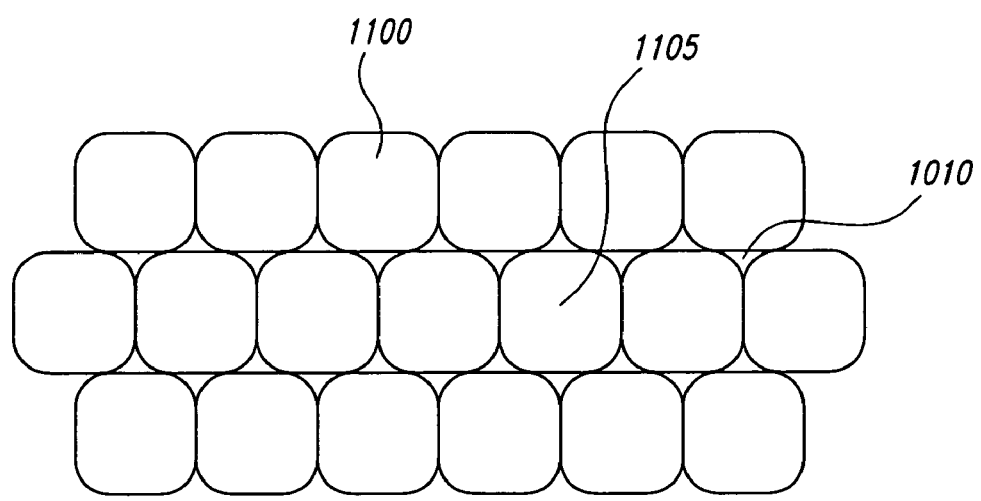
FIG. 11 is a schematic view of a staggered binder deposition configuration in accordance with principles of the present invention.
Figure 12:
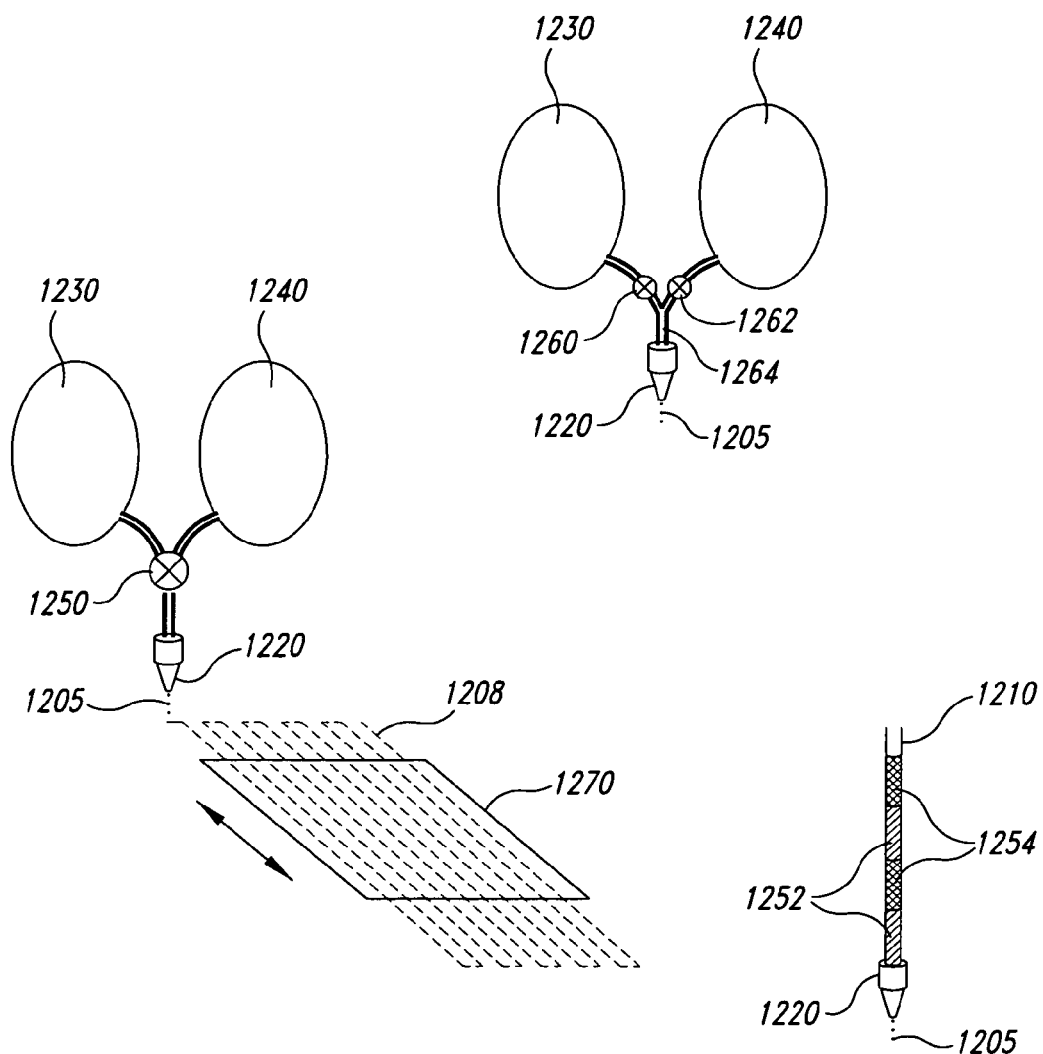
FIG. 12 is an exploded schematic view illustrating the relevant elements for slurry printing through single nozzle with switching in accordance with principles of the present invention.

In three-dimensional printing there are at least two possible arrangements of primitives relative to each other in adjacent layers. FIG. 10 illustrates one possible arrangement where primitives 1000 in any given layer are directly above primitives 1005 in the layer immediately below it. This may be referred to as a stacked arrangement. FIG. 11 illustrates another possible arrangement where primitives 1100 in any given layer are located halfway between primitives 1105 in the layer immediately adjacent to it. This may be referred to as a staggered arrangement. Mesostructure is interconnected microporosity or microstructure; therefore, a stacked arrangement may be more conducive to the formation of mesostructures than is a staggered arrangement.

It may be desired that some portions of the biostructure be made so as to contain mesostructures and also to contain other regions which may have a more uniform packing density of powder particles, i.e., a more thorough joining of primitives so as not to exhibit mesostructures. For example, regions of the biostructure may include designed regions that discourage or prohibit in-growth of soft tissue. For some non-load bearing biostructures uses where loading may be postponed until after in-growth of natural bone has occurred, it is acceptable for the implant to be of lower strength. For other applications, the biostructure may require more strength than what is available from a biostructure containing mesostructures everywhere. Accordingly, it is possible to make a biostructure wherein some portions have mesostructures and other portions have primitives bound to each other essentially completely. Either the portion with mesostructures or the portion without mesostructures, or both, could optionally contain macrostructures.

One method of producing and eliminating mesostructures is by adjusting the saturation parameter during printing in different regions. A sufficiently large saturation parameter may result in an essentially uniform distribution of powder particles in the final biostructure and primitives that are essentially fully bound to one another. A sufficiently small saturation parameter may result in the creation of mesostructures.

Adjustment of the saturation parameter from one region of a biostructure to another, using a given dispenser, may be achieved by adjusting any of the variables which together make up the saturation parameter. This may be achieved by adjusting the amount of dispensed liquid per unit distance traveled along the principal direction of motion. In raster printing this may be adjusted by adjusting either the speed of the printhead or the timing of commands for drop ejection. For example, without adjusting the printhead speed, drops may be ejected at longer intervals of space or time in some regions, and at shorter intervals of space or time in other regions. For example, a doubling of saturation parameter may be achieved by dispensing in some print regions a drop at every location of a scheduled pattern, and by dispensing in other print regions a drop only at every second location in that same pattern. Some dispensing technologies, such as piezoelectric, may permit continuous (within some range) variation of the local saturation parameter by providing drops whose volume may be continuously varied (within some range) according to the command given to the dispenser.

One possible motion pattern for three-dimensional printing is a raster pattern. In raster printing, the printhead moves in straight lines along what is referred to as the fast axis. After completion of each pass in the fast axis, the position of the fast axis may be incremented by a specified distance along the slow axis, and another pass is performed along the fast axis. In such printing, the overall shape of the mesostructures is usually long and generally straight corresponding to the motion of the printhead, although on a small-scale mesostructures may exhibit localized irregularities because of randomness of localized rearrangement of powder particles during drying.

There is also another, more general possible motion pattern that could be used in three-dimensional printing, which is vector printing. In vector printing, the printhead can move simultaneously in both of the principal (orthogonal) horizontal axes and so can trace curved paths. In such printing, the overall pattern or path of the printing in the part can be curved. Accordingly, the shape of the mesostructures can again be long in one direction and small in at least one other direction, but in the long direction the mesostructures can have a generalized shape such as a curving shape. Of course, again the mesostructures could exhibit some localized irregularities because of randomness of localized rearrangement of powder particles during drying. It would further be possible to use vector printing in some portion(s) of a biostructure and raster printing in other portion(s) of the same biostructure.

Article of Manufacture Using, For Example, Demineralized Bone Matrix

Description up until now has primarily described an article whose powder particles have been of a ceramic material which is sinterable. One feature of such a material system is that no binder substance is present in the finished product, and the particles are joined directly to each other. However, that is not the only material system of interest. One particular materials system of interest for the biostructure includes at least some of the particles comprising demineralized bone matrix (DBM). Demineralized Bone Matrix is osteoinductive because of its content of organic material, which is more favorable to the ingrowth of natural bone than is the case for ceramic materials, which are merely osteoconductive. DBM could include superficially demineralized, partially demineralized, or fully demineralized bone particles, all of which are included in the term demineralized bone matrix. The particles may all be demineralized bone matrix. Alternatively, some of the particles may be demineralized bone matrix and other particles may be other forms of bone such as nondemineralized (ordinary) bone. The demineralized bone particles and also the (if used) nondemineralized bone particles may be obtained from cortical, cancellous, or cortico-cancellous bone of autogenous, allogenic, or xenogenic origin, including porcine or bovine bone. DBM is different from materials such as ceramics in that it cannot be exposed to temperatures anywhere near as high as ceramics can, or it will decompose. It is further possible that in addition to particles of demineralized bone and possibly ordinary bone, still other substances could be included in the powder particles that are bound together to form the biostructure. Examples of such other substances include hydroxyapatite, tricalcium phosphate and other calcium phosphates and calcium-phosphorus compounds, hydroxyapatite calcium salts, inorganic bone, dental tooth enamel, aragonite, calcite, nacre, graphite, pyrolytic carbon, Bioglass.RTM., bioceramic, and mixtures thereof. Hydroxyapatite is generally considered to be nonresorbable by the human body, while tricalcium phosphate and other calcium-phosphorous compounds are resorbable. It is further possible for some of the powder particles to be a polymer such as PLGA, PLA, polycaprolactone, PMMA, etc., as described elsewhere. The powder particles may be particles of the described substances coated or coacervated with another substance as described below. DBM is not nearly as rigid as natural bone, while most of the other mentioned substances are fairly rigid.

The powder from which the biostructure of the present invention is made may comprise any number of the above substances in any combination. Various combinations may be selected to provide desired overall properties as far as stiffness, resorption rate, etc. As described in more detail below, different regions of the biostructure can have different powder composition. The powder particles may be of aspect ratio reasonably close to spherical or cubical, or, alternatively, at least some fraction of the particles may be of more elongated geometry such as fibrous. The term particle is used herein to refer to all of these shapes.

A binder substance is a substance that is capable of binding the powder particles to each other and to other solid regions. In the biostructure, bone augmentation or tissue scaffold biostructure of the present invention, the particles are bound to each other by at least one binding substance. The binding substance(s) may be collagen or collagen derivatives. Other suitable substances include polymers, which may be either resorbable or nonresorbable.

Suitable biocompatible binders include biological adhesives such as fibrin glue, fibrinogen, thrombin, mussel adhesive protein, silk, elastin, collagen, casein, gelatin, albumin, keratin, chitin or chitosan; cyanoacrylates; epoxy-based compounds; dental resin sealants; bioactive glass ceramics (such as apatite-wollastonite), dental resin cements; glass ionomer cements (such as Ionocap.RTM. and Inocem.RTM. available from Ionos Medizinische Produkte GmbH, Greisberg, Germany); gelatin-resorcinol-formaldehyde glues; collagen-based glues; cellulosics such as ethyl cellulose; bioabsorbable polymers such as starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, poly (propylene glycol-co-fumaric acid), tyrosine-based polycarbonates, pharmaceutical tablet binders (such as Eudragit.RTM. binders available from Huls America, Inc.), polyvinylpyrrolidone, cellulose, ethyl cellulose, micro-crystalline cellulose and blends thereof; starch ethylenevinyl alcohols, polycyanoacrylates; polyphosphazenes; nonbioabsorbable polymers such as polyacrylate, polymethyl methacrylate, polytetrafluoroethylene, polyurethane and polyamide; etc. Examples of resorbable polymers are starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, poly (propylene glycol-co-fumaric acid), tyrosine-based polycarbonates, pharmaceutical tablet binders, polyvinylpyrollidone, cellulose, ethyl cellulose, micro-crystalline cellulose, and blends thereof. Examples of nonresorbable polymers are polyacrylate, polymethyl methacrylate, polytetrafluoroethylene, polyurethane, and polyamide. Binder substances may vary in amount or composition from one place to another in the biostructure.

In an article made from DBM, the particles of DBM are not physically merged with each other as they are in a partially sintered article, but rather are attached to each other by binder substance. The binder substance remains in the finished article.

It is possible, at least with certain manufacturing methods, that the powder and the binder substance taken together do not occupy all of the space within the biostructure. Accordingly, the biostructure may further contain still other substances. One category of such substances is substances to increase the mechanical strength of the biostructure, for example, Fibrin. Also, the strengthening substance may be a polymer, examples of which are given herein. This substance may vary in amount or composition from one place to another in the biostructure. More than one such substance may be used.

Alternatively, another category of substance that may be included in the biostructure in addition to powder and binder substance is a bioactive substance. Bioactive substances that can be readily combined with the bone particles are described below in greater detail.

It is further possible that in a biostructure that contains powder particles and binding substance(s) and strengthening substance(s), there still may be room for other substances. Such substances could be bioactive substances, examples of which were just given. Such substances may vary in amount or composition from one place to another in the biostructure, and more than one such substance may be used.

As discussed below, it is also possible that a dissolvable material could occupy the portions of the biostructure, such as to provide a strengthening or handling-protection effect that goes away quickly upon installation of the biostructure in the body. This substance may vary in amount of composition from one place to another in the biostructure, and more than one such substance may be used.

In general, it is possible for any component of the biostructure to have different composition from one place to another within the biostructure, and for more than one composition of any category of substance to be used. The powder composition can vary. The binder substance can vary in composition or concentration from place to place within the biostructure. The composition or concentration of strengthening substance, bioactive substance, soluble substance or other substance to vary from place to place within the biostructure.

Resorbability means that materials will not persist indefinitely in the human body, but rather will be chemically changed and eliminated. It may be desirable for all or at least some of the material components of the biostructure to be resorbable. Of the various materials mentioned, hydroxyapatite and some polymers such as polymethylmethacrylate (PMMA) are non-resorbable. Most of the others are resorbable, including specifically DBM, various calcium phosphates, collagen, fibrin, and poly lactic co-glycolic acid (PLGA).

The biostructure may have an overall shape that includes geometric complexity. For example, it may include undercuts, recesses, interior voids, etc., as long as the undercuts, recesses, interior voids, etc., have access to the space outside the biostructure. The biostructure may be shaped appropriately so as to replace particular bones or segments of bones or spaces between bones or voids within bones. Examples of such bones are given in the Examples. The biostructure may be dimensioned and shaped uniquely for a particular patient. Also, although the invention is capable of being made as a biostructure having a specific overall shape, the techniques of the present invention could also be used to produce simple overall shapes, such as blocks, for the purpose of being shaped by a surgeon at the time of installation.

The biostructure also may have a specified internal geometric architecture, at a variety of dimensional scales. The biostructure may contain macrostructure, mesostructure, microstructure, open holes, passageways, or channels of size scale approximately equal to or larger than the size scale of a primitive shape as described later, as long as the holes, passageways, or channels have access to the space outside the biostructure. It is believed that such macrostructures, holes, passageways, or channels may become paths for in-growth of natural bone, cartilage or other tissue. Such passageways or channels need not be straight holes; they can be curved, have changes of direction, have varying cross-section, etc., and can even branch to form other passageways or channels. Such passageways or channels can have cross-sectional dimensions as small as 5 microns.

It is also possible for the biostructure to contain another type of internal geometric feature such that some regions may contain powder particles bound to each other and other regions may contain powder particles which are not bound to each other but which remain in the biostructure. This trapping of unbound particles within the biostructure can occur in internal configurations that are extremely long and narrow and/or are not connected to the space outside the biostructure, and are related to the inability to remove unbound powder from regions of certain dimensions and geometry. These features may be on a size scale approximately equal to or slightly smaller than the size scale of a primitive shape as described later. It is believed that these features are also conducive to in-growth of natural bone. These features may be referred to as mesostructure.

Porosity may be defined as empty space within bound regions of the biostructure. This may be defined exclusive of any large-scale holes or voids that may be designed into the biostructure. Porosity refers to incompletely filled space between individual powder particles and so the size scale of pores is similar to the size scale of the powder particles. Appropriate later steps such as compression of the overall article or infusing the article with other materials can reduce the porosity that occurs somewhat naturally with the basic manufacturing technique described later. This natural porosity is typically in the tens of percent, but larger porosities can also be achieved with special techniques. With the present invention it is possible to produce a biostructure having porosity that is significantly greater than the rather miniscule porosity achievable by compression molding of DBM. This ability to provide porosity may be useful for bone augmentation and especially may be useful for tissue scaffolds.

Further, the porosity of the biostructure may vary from region to region of the biostructure. For example, appropriate porosity might be used to imitate the structure of cortical bone (the dense hard outer portion of bone) or of cancellous bone (the softer inner portion of bone) or of both types of bone within a single biostructure. Some regions of the biostructure may resemble cortical bone while other regions resemble cancellous bone. A portion of the biostructure could be made suitable for bone augmentation while another portion of the biostructure could be made as a tissue scaffold.

The biostructure also may have an internal architecture or design in terms of its physical composition, which may vary from place to place within the biostructure. It is possible to have variation of the local concentration or composition of any one or more of the following substances: binder substance; powder; strengthening substance; bioactive material; soluble substance; or any other substance. The biostructure could include either internal geometric architecture as already described, or compositional variation as just described, or both.

For example, tissue scaffolds are porous matrices designed for cells and tissues to grow into. They are typically characterized by an empty space fraction that is larger than that for bone augmentation articles, and a specified pore size. Within a tissue scaffold, the porosity may vary from place to place. It is possible that some regions of a biostructure may be a bone augmentation biostructure and other regions may be a tissue scaffold.

Methods of Manufacturing with Demineralized Bone Matrix

Following the three-dimensional printing operation as described in detail above and with reference to various patents cited and incorporated herein, the biostructure as manufactured up until that point contains at least osteoinductive particles such as demineralized bone matrix and at least one binder substance connecting particles to each other. The biostructure will have sufficient strength to retain its manufactured shape without the support of the unbound powder. The biostructure may not be as strong as may be desired, however, especially for applications within the body that bear significant loads.

One method for increasing the strength of the biostructure is to perform a processing step or steps to either partially or completely fill open pores in the biostructure with another substance or substances. One purpose of such additional substance may be to increase mechanical strength. Such a strengthening substance may be fibrin or fibrinogen, or polymers or other substances, examples of which are given herein. Poly lactic co-glycolic acid and related substances may also be used.

The strengthening substance could be introduced into the biostructure in the form of a liquid and then allowed to solidify. For example, the liquid could contain the strengthening substance dissolved in a solvent and the solvent could be allowed to evaporate, or it could be melt-infused or infused as a monomer and then polymerized, all of which are described later. More than one strengthening substance may be used. The liquid that carries the strengthening substance may be a liquid in which the binder substance is not significantly soluble.

A similar infusion process could be performed to deposit one or more bioactive substances in the biostructure. Deposition of bioactive substances could be performed either after or instead of deposition of strengthening substances. Water-soluble filler substances could be deposited at any stage. The final biostructure could have essentially all of its empty spaces filled with any of the various described substances, or it could still have empty spaces. The various possible filler materials could be deposited so that the concentration or composition of any of the deposited materials varies from place to place within the biostructure, by infusing substances into pores in such a way that pores in some region(s) of the biostructure are filled to a different extent or with a different substance compared to pores in other region(s) of the biostructure. This infusing can be of a strengthening substance, a bioactive substance, or other type of substance.

Preparation of Coacervate for DBM

The invention may include the use of powder that is a coacervate such as of collagen or other substance onto particles of demineralized bone matrix. The preparation of a coacervate of collagen onto particles such as particles of demineralized bone matrix may include lyophilization (freeze drying).

Coacervates are prepared by suspending particles in a carrier liquid which is a solution which comprises a dissolved substance, and then causing the dissolved substance to come out of solution and deposit in the form of a thin layer on the surfaces of the suspended particles. One of the later steps in the coacervation process is to dry the coated particles, i.e., to evaporate whatever is left of the carrier liquid. In particular, the step would be to dry the particles in such a way that for the most part the coated particles, when dry, do not stick together or clump to each other. If this is achieved, then after the coated particles are dry, they can be handled and roller-spread as is commonly done in three-dimensional printing.

For many substances, it is possible to remove the carrier liquid through evaporation of the carrier liquid at either room temperature or elevated temperature and obtain a good yield of coated particles that are mostly physically separate from each other. However, collagen is a particularly sticky substance and it was found that such methods were not suitable to produce particles that were mostly physically separate from each other. Accordingly, a preparation of demineralized bone particles coated with collagen was prepared by processes including lyophilization (freeze-drying).

Bone particles were made from animal bones by cleaning the bones, cutting them into pieces, and grinding them. Then, the bones were demineralized by treating them with hydrochloric acid. Next, collagen was dissolved to form a solution, and bone particles were stirred into that solution. Next, ethanol was added to the solution, which removed water from the collagen and caused the collagen to come out of solution including depositing onto the surfaces of the particles. Next, the entire solution was frozen and then was placed in a vacuum chamber and was lyophilized. The result was bone particles which were coated or coacervated with collagen, and which were generally physically separate from each other. They were suitable for use as the powder in a 3DP process.

The biostrucuture and materials of the present invention are also suitable to be modified after completion of the manufacturing steps that give the biostructure its shape, such as by a surgeon during an operation. Such modification can be performed by filing, drilling, grinding, or in general any cutting operation or material removal technique.

The osteoinductivity of materials such as demineralized bone used in the present invention, and the rigidity of articles made according to the present invention, and the abilities for variation of external shape and variation of internal geometry and architecture and composition, all contribute to providing capabilities not currently available or not currently available at any reasonable cost. Demineralized bone is currently an underutilized substance that is available as leftover material from the manufacturing of custom-shaped solid bone augmentation or tissue scaffold articles from allograft sources.

Location-Specific Powder Composition

Three-dimensional printing can also achieve variation of local composition of the powder or solid material within a biostructure. Two general ways of achieving variation of the powder or matrix material composition are described herein, one being to physically deposit powder particles of specified composition in specified places, and the other being to deposit uniform-composition powder and later chemically change it in specified places by chemical reaction. In regard to the first method, variation of powder composition can be achieved by depositing different compositions of powders in different places in a layer. Varying the powder composition in a biostructure provides advantages in terms of biological considerations, such as having both resorbable regions and nonresorbable regions, together with other features. One aspect of the invention provides a method of depositing powder layers having fully detailed variation of composition within a layer using a continuous (always on) flow of suspension. Principles of the present invention include a method of achieving layer deposition quality nearly equal to that of a continuous (always on) flow jet, by co-aiming individual streams or discrete drops from different dispensers at a common impact location on the build bed. Another aspect of the invention provides ways of reducing waste or recycling of dispensed suspension, such as for use with powders that are expensive.

A materials family of interest for bone substitute products in accordance with the present invention includes the substances hydroxyapatite and tricalcium phosphate, both of which occur in natural bone, and other related calcium-phosphorus compounds. Hydroxyapatite is generally considered to be nonresorbable by the human body. Tricalcium phosphate is resorbable by the human body over a time period of months. Other calcium-phosphorus compounds are also resorbable. In the human body, resorption of resorbable materials frees up space that may gradually become occupied by newly grown natural bone. Hydroxyapatite may be prepared in powder form and may make up portions of the bone substitute biostructure. Tricalcium phosphate or other resorbable calcium phosphorus compounds may also be prepared in powder form and also may make up portions of the bone substitute biostructure.

In one embodiment of the present invention, layers of powder particles are deposited by dispensing suspension. The various suspensions used in the method of the present invention may comprise powder particles and a carrier liquid and additives to the carrier liquid. The individual substances of the powder particles in different suspensions may be, in one suspension, hydroxyapatite, and in another suspension, tricalcium phosphate or other resorbable calcium-phosphorus compounds. As is known in regard to suspensions, the powder particles in the suspension may be selected so as to be suitably small so as to have a high likelihood of remaining in suspension. Suitable additives to the carrier liquid, such as steric hindrants or suspending agents or surfactants, may be included to help keep the particles in suspension, such as by preventing them from agglomerating.

The suspension may be delivered to the dispenser or nozzle by a fluid supply system that may include agitation or continuous circulation to help maintain the particles in suspension. Two or more different suspensions each having respective powder compositions may be provided, with each suspension able to be dispensed in appropriate places on a layer. For similarity of dispensing of the respective suspensions, the various fluid parameters which characterize each suspension may be chosen or formulated to be approximately equal to each other, such as viscosity of carrier liquid, additive formulation, particle size, solids content, etc., although this is not absolutely necessary. Typical additives may be added to the carrier liquid to promote suspension. A typical powder particle size for creation of a stable suspension is 40 microns or smaller. or smaller, dependent on parameters such as density of the particle and composition of the liquid.

Percolation means such as a porous substrate underlying the build bed may be used to promote the drainage of the carrier liquid, as is known in the art. Application of external heat may be used to accelerate the evaporation of the suspension carrier liquid after deposition of a layer has been completed. When the powder in the most recently deposited layer is sufficiently dry, one or more binder liquids, each of which may comprise one or more binder substances, may be dispensed onto that layer in selected places, as is usually done in 3DP, to bind powder particles to each other and to other bound regions. The whole sequence may then be repeated as many times as needed. Possible subsequent processing steps are described later.

The carrier liquid of the suspension, and the binder substance or substances used for the 3DP process, may be chosen so that the binder substance or substances are not excessively soluble in the slurry carrier liquid. This assures that deposition of suspension for subsequent layers may be performed without appreciably affecting the binding of already-printed layers. For example, the binder substance may be polyacrylic acid and the suspension carrier liquid may be isopropanol or water. Polyacrylic acid is somewhat soluble in isopropanol and water, but not excessively soluble.

A deposited powder layer may be described in terms of its compositional uniformity (comparing the composition of the powder from one place to another) and its geometric uniformity (whether its thickness is essentially constant everywhere). For manufacturing simple articles for industrial products, slurry-deposited layers are typically compositionally uniform because all suspension is delivered from the same source, and effort is made to achieve geometric uniformity as much as possible.

In this embodiment of the present invention, it may be desirable to achieve geometric uniformity of the deposited layer even though the goal of the present invention is to achieve compositional non-uniformity of the deposited layer. In this regard, it may be desirable that every point on the build bed receives as closely as possible the same amount of deposited suspension as any other point. Further, it is helpful to realize that depositing a layer by dispensing suspension from a nozzle which is moving relative to the build bed involves typically creating, at the point of impact or deposition, a very slight mound or accumulation of slushy material adjacent to a region which has not yet received a deposit of new material. From at least some directions and for some period of time, the mound may be unsupported. It can be expected that at any impact point the newly-deposited slight mound may have a tendency to migrate or spread, especially in whatever direction and during whatever time period it is not supported by adjacent deposited material of similar height.

A consideration for minimizing migration or spreading of deposited suspension may be to minimize the number of directions from which a mound of deposited slurry is unsupported and the duration of time for which it is unsupported. In this respect, continuous or uninterrupted deposition with constant-velocity relative motion may in general do a better job of minimizing the opportunity for spreading than would a more interrupted type of deposition, and hence would promote the creation of a deposited layer which is as geometrically uniform as possible. Continuous deposition means that to the greatest extent possible there is no interruption in the sense of an impact point being followed in the direction of dispensing motion by a non-impact point.

There are several possible ways of creating a location-specific composition of the powder in a layer through appropriate deposition of slurry or suspension (the terms slurry and suspension being used interchangeably herein). In one of these ways, suspension of varying composition may be dispensed from a continuously flowing nozzle. Also, there are at least two ways in which suspension may be dispensed from multiple nozzles in an on-demand manner, with each nozzle being dedicated to a particular composition of suspension. The techniques are further described but are in no way limited examples by the following examples.

Dispensing Suspension from a Nozzle in a Continuous Flow with Variation of Composition of Suspension In conventional slurry deposition, in which a continuously flowing jet is moved in a motion pattern such as a back-and-forth raster pattern, the continuous nature of the rastering means that at least along the fast direction of travel the deposition occurs as continuously as possible. In the present invention, it is also possible that a jet be essentially continuously flowing, and yet the composition of the delivered suspension in the jet can vary with time and hence vary with place of deposition. It can be envisioned that the stream of liquid passing through the nozzle may comprise a bolus of suspension of one composition preceded and followed by suspension of another composition(s).

FIG. 12 is an exploded schematic view illustrating the relevant elements for slurry printing through since nozzle with switching. A tube 1210 delivers a fluid stream 1205 to a nozzle 1220. The fluid stream 1205 comprises discrete regions 1252 of one composition and regions 1254 of another composition when contained in the tube 1210. For example, the suspension dispensed in the jet may be drawn from any of two or more different sources 1230 and 1240, and the drawing of the suspension may be switched between or among the sources as needed.

When using two distinct suspensions, a three-way valve 1250 that switches between two sources 1230 and 1240 may be used. Alternatively, two discrete on/off (two-way) valves 1260 and 1262 may be used to perform the switching. Valves 1260, 1262 operate such that when flow is desired, one of the valves is open and the other is closed. The flow is individually switched by valves 1260 and 1262 may then join at a "Y" fitting 1264 and proceed through a tube 1210 to be dispensed by nozzle 1220.

The valve 1250 or valves 1260 and 1262 may be located on the printhead (the overall assembly which is moved with respect to build bed 1208 by the motion control system) and may be physically as close as possible to nozzle 1220, thereby minimizing the fluid travel time, i.e., the interval between the time when choice of fluid occurs at the switching-over point and the time when the composition of the dispensed suspension at the nozzle changes. The switchover point, where the fluid is chosen as being composed of one suspension or the other, may, in the case of a three-way valve 1250, be considered to be the three-way valve itself. In the case of two two-way valves 1260 and 1262, the switchover point may be considered to be the "Y" fitting 1264 where conduits bringing fluid from individual valves merge. The controls and programming of the switchover relative to the position of the dispenser over the build bed 1270 may take this into account.

For example, if it is known that switching over from one dispensed suspension composition to another is desired to occur when the nozzle 1220 is at a certain location over the build bed 1270, and if there is a known travel time for fluid between the switch-over point and the nozzle 1220, then the controls may be programmed so that the switching occurs earlier than when the nozzle is at the point of interest, shifted by an amount of time which is the travel time. Control of such actions may also use positional input such as may be obtained from encoders on the axes of the motion control system.

It may be desirable to formulate both suspensions so that they have similar physical properties so as to flow at similar rates under similar conditions, as already mentioned. If the respective flows are pressure driven, essentially similar pressure sources (not shown) may be provided for each of the respective suspension reservoirs 1230 and 1240. It would also be possible to dispense the suspensions by means of a pump such as a peristaltic pump or other form of positive displacement pump with appropriate switching between or among the respective sources of suspension.

The motion of the nozzle 1220 with respect to the build bed 1270 may be provided by a motion control system (not shown) as is known in the art, such as a servomotor system. It is possible that the suspension could be dispensed by a nozzle moving in a raster pattern 1208 of straight lines, in which case it may be desired that the nozzle be moving at a substantially uniform velocity any time it is dispensing suspension over the build bed 1270. Having the nozzle travel at a substantially uniform velocity within the region of the build bed 1270 helps promote the desired geometric uniformity of deposition. It is possible that the dimension of the raster pattern in the fast axis may be larger than the dimension of the build bed 1270 in that direction, because in the immediate vicinity of the turn-around, it may not be possible for the motion control system to achieve the desired magnitude or uniformity of velocity.

Switching between or among dispensed suspension compositions could be performed at any arbitrary time during actual dispensing of suspension over the build bed, which would provide complete opportunity for detailed variation of material composition. Adjustments may be made based at least in part on spatial information as to where the printhead is at a given time, such as from an encoder mounted on the fast axis of the motion control system. Because of the travel time between the switch-over point and the actual dispensing at the nozzle 220, such switching of the valves may have to occur before the jet starts its pass on a given line, e.g., the switching might have to occur during the turn-around time during the regions of non-uniform velocity of the dispenser or printhead even though the change of dispensed composition is desired to occur when the nozzle is at a particular location over the build bed. Such delays and adjustments can be programmed into software that controls the 3DP process.

If the configuration of two two-way valves is used, it is further possible to program the system so that during at least some of the motion in the turn-around regions, suspension is not dispensed, which can help to conserve possibly expensive powder. In the system containing two two-way valves 1260 and 1262, it is possible to operate the system such that during the turn-around times when the nozzle 1220 is outside the build bed 1270, both valves 1260 and 1262 are closed.

If a three-way valve 1250 were used, it would be possible to put an on-off valve (not shown) downstream of valve 1250, or to put a separate on-off valve (not shown) upstream of valve 1250 in each of the supply lines coming to it. Such arrangements would help to avoid unnecessary dispensing of suspension and hence avoid the waste of, or the need to recycle, potentially valuable materials. This would be useful in the case of dispensing hydroxyapatite or tricalcium phosphate powders.

Figure 15:
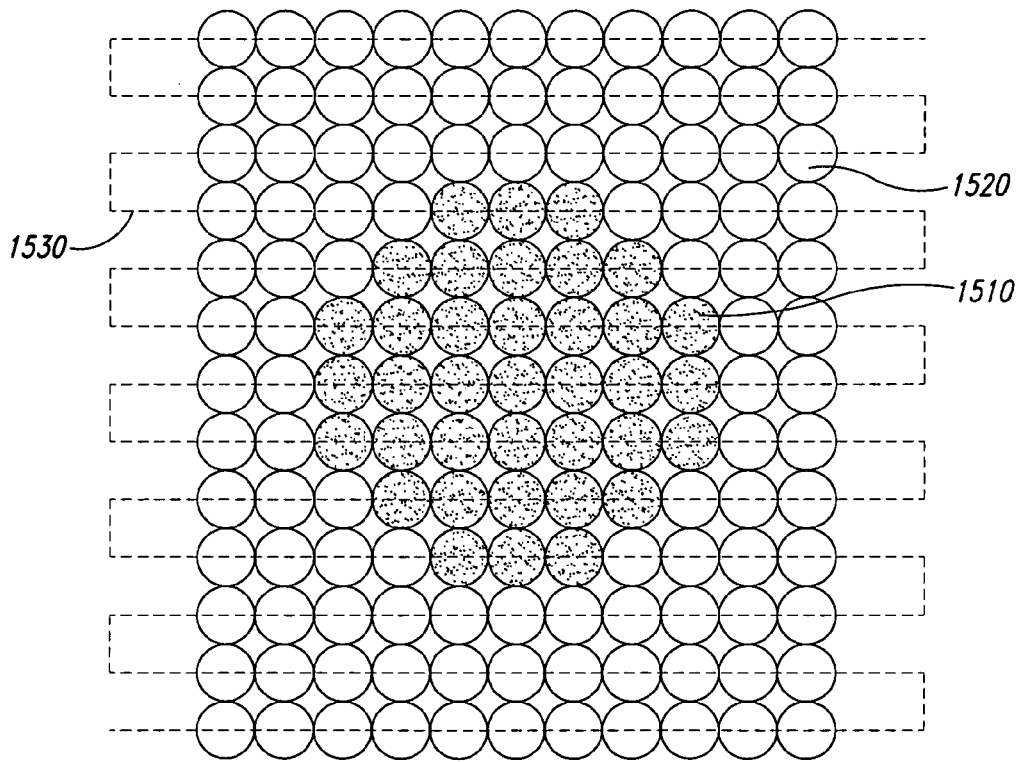
FIG. 15 is a top view of one pattern of deposition of two suspensions to create an engineered regenerative biostructure of given composition in accordance with principles of the present invention.

FIG. 15 illustrates that in the regions outside the build bed, which are turn-around regions, dispensing of suspension may be turned off. With the ability to turn off the flow of suspension easily and frequently, it is possible to dispense in a back-and-forth raster pattern as has been described, or alternatively it would be possible to dispense in an all-in-one-direction manner, i.e., the dispenser could move across the build bed in a first direction while dispensing, could move back while not dispensing, and could repeat that sequence. In any such system, it is possible that if the dispenser has been closed or idle for a while, the composition of the suspension carrier liquid at the tip of the dispenser may be different from what is intended, as a result of evaporation. Accordingly, it may be desirable to occasionally operate the dispenser at certain times when it is not over the build bed, so as to dispense small amounts of slurry from the dispensers sufficient to restore the intended composition of slurry to the dispenser tip, or to prevent clogging.

There could also be a binder liquid dispenser that may be mounted on part of the same printhead as the suspension dispenser.

Dispensing Multiple Suspensions from Multiple Nozzles Co-Aimed to a Common Impact Point in the Plane of the Build Bed Another method of location-dependent suspension deposition involves dispensing of suspension from more than one discrete nozzle or dispenser. This simplifies the fluid supply system in the sense that each individual dispenser or nozzle can be dedicated to a particular suspension composition, and the choice of which suspension composition is deposited at a particular location can be made by the choice of which dispenser is used to deposit the suspension at a particular location. It is possible that two different dispensers may both aim their dispensed suspension at a common impact location on the plane of the build bed.

Figure 13A:
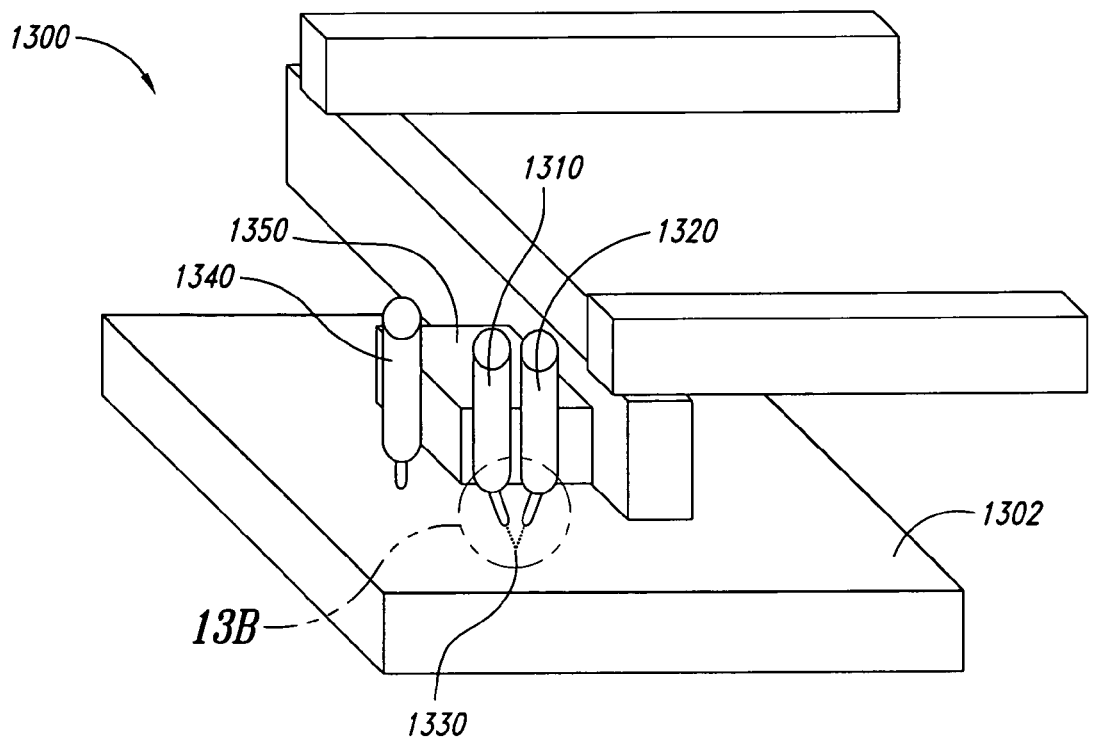
FIG. 13A is an isometric view of a three-dimensional printing apparatus configured for suspension deposition with two co-aimed dispensers in accordance with principles of the present invention.
Figure 13B:
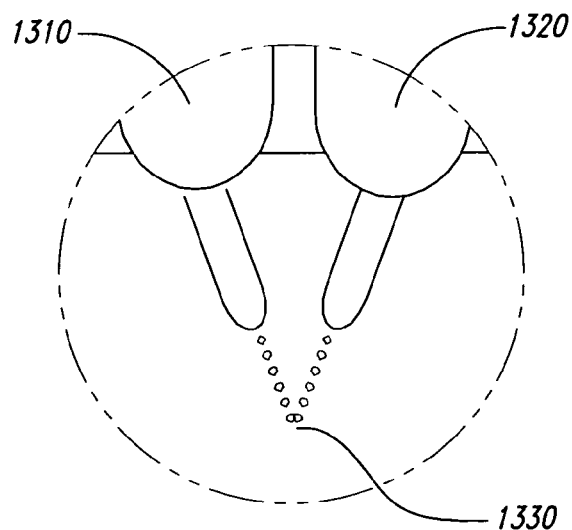
FIG. 13B is an enlarged view of the co-aimed dispensers of FIG. 13A.

FIG. 13A is an isometric view of a three-dimensional printing apparatus configured for suspension deposition with two co-aimed dispensers in accordance with principles of the present invention. FIG. 13B is an enlarged view of the co-aimed dispensers of FIG. 13A. Suspension dispensers 1310 and 1320 both aim dispensed suspension at a common impact point 1330 in the plane of the build bed 1302.

Appropriate tilting and positioning of the respective nozzles or entire dispensers or both may be used. Controls may be used to ensure that exactly one of the dispensers dispenses at any given point on the build bed, or perhaps more practically speaking, at any given spatial increment into which the build bed may be discretized by the motion control and 3DP system. In this case, the common impact point 1330 of the dispensed slurry would move along on the build bed in a motion pattern such as a raster pattern defined by the motion of the printhead, which would be essentially the same motion pattern as if a single nozzle as in the previous example performed dispensing.

When changeover of dispensing from one dispenser to the other dispenser is desired to occur, in order to achieve a compositional change, one dispenser stops dispensing and the other dispenser begins dispensing. However, there would be essentially no shift in the impact point of the dispensed suspension, because both dispensers would have the same impact point on the plane of the build bed, and so there would be no disruption in the apparent motion of the impact point on the build bed.

As described later, the dispensers may be drop-on-demand dispenser such as a piezoelectric drop-on-demand dispenser or may be a microvalve based dispenser operating in either drop-on-demand or line-segment mode. It is believed that co-aiming will provide continuousness of deposition approaching that of a continuous-flow jet in the same motion pattern, while providing fully detailed control of composition of the deposited layer.

FIG. 13 further illustrates a binder liquid dispenser 1340 for dispensing binder liquid onto the build bed during a subsequent step of the 3DP process. This binder liquid dispenser 1340 may be mounted onto the same printhead 1350 and motion control system as the suspension dispensers 1310 and 1320, although it does not have to be.

In connection with the use of such a system, at least one of the dispensers will be turned off at any given time, and sometimes both of them may be turned off. Having both dispensers turned off during at least some of the turn-around region can help to conserve potentially expensive powder material. "Off" periods are times when evaporation of carrier liquid of the suspension may occur at the tip of the dispenser. This may result in a localized slurry composition at the tip of the dispenser which is different from what is intended, and may even cause a clog. Accordingly, it may be desirable to occasionally operate the dispenser at certain times when it is not over the build bed so as to dispense small amounts of slurry from the dispensers sufficient to restore as-mixed composition of slurry to their tips, or to prevent clogging.

Dispensing Multiple Suspensions from Multiple Separately-Aimed Nozzles

Figure 14:
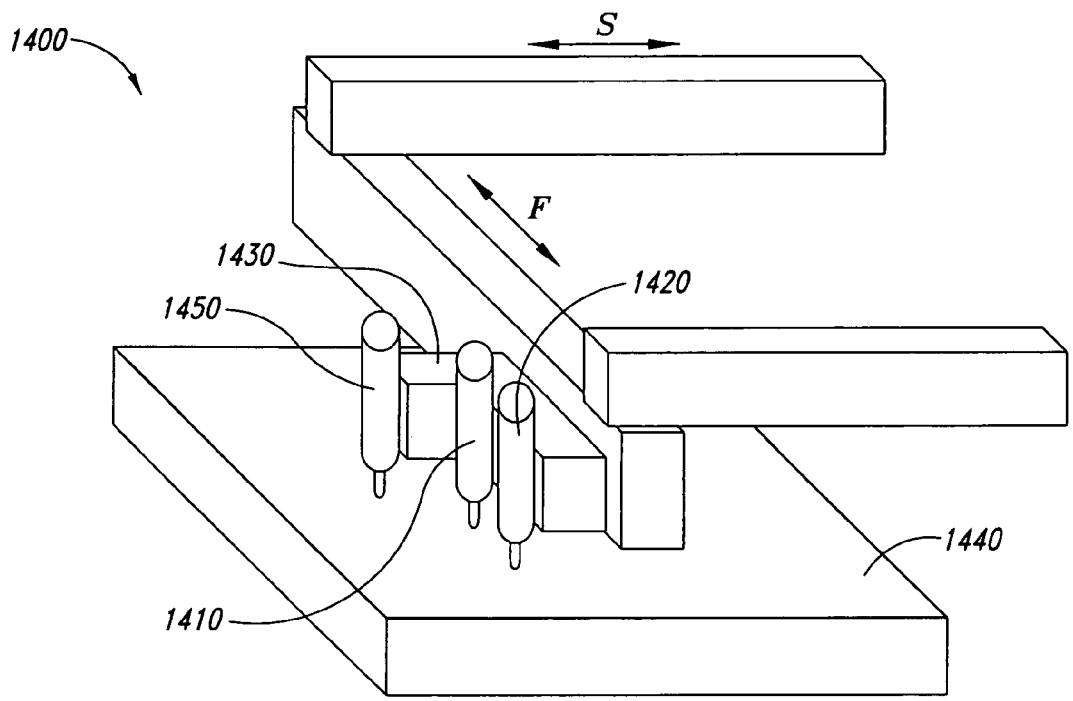
FIG. 14 is an isometric view of a three-dimensional printing apparatus configured for suspension deposition with two separately aimed dispensers in accordance with principles of the present invention.

It may not always be possible or desirable to aim two different dispensers at a common location on the plane of the build bed. Accordingly, FIG. 14 illustrates an alternative three-dimensional printing apparatus configured for suspension deposition with two separately aimed dispensers. Two suspension dispensers 1410 and 1420 mounted on a printhead 1430. First suspension dispenser 1410 may dispense first suspension, and second suspension dispenser 1420 may dispense second suspension.

In this configuration, wherever there is a change of composition of dispensed suspension, there may also be a change in the impact point on the build bed and hence there may be an interruption in the deposition onto the build bed in the sense that where a changeover occurs, the physically next deposition along the direction of motion of the printhead in the fast axis may not follow immediately in time, or may even have already occurred.

If it is necessary to have separate impact points for each individual dispenser, it may be advantageous to have the impact points all be along a single line of deposition along the fast axis direction of motion of the printhead as is shown in FIG. 14. In this way, all points on a given line will at least receive their deposition of slurry during one pass of the printhead, so that the time interval between receipt of slurry will not be as long as it would be if different passes of the printhead were involved on the same line. This may somewhat minimize any opportunity for unsupported mounds of slurry to spread before becoming more fully supported and should provide the best results achievable within this example.

In FIG. 14, the two dispensers 1410 and 1420 are mounted in such a way that they are in line with each other along the direction of the fast axis F of motion. The respective impact points of each individual dispenser may be known and taken into account, along with the printhead velocity, in determining the timing and aiming of dispensing of respective dispensed liquids as defined in the 3DP control systems and programming. Such dispensing may be performed with drop-on-demand printheads such as piezoelectric drop-on-demand printheads or with microvalve printheads in either drop-on-demand mode or line-segment mode. Such dispensing allows the suspension to be turned off when the dispenser is not above the build bed 1440, thereby economizing on the use of possibly expensive powder such as hydroxyapatite.

If migration or spreading of dispensed suspension is not a problem in a particular application, it may be possible to dispense the respective suspensions in a manner in which the dispensings are more independent of each other in time. In this case the various dispensers might not have to be co-located along a line parallel to the fast axis. This may allow more design flexibility regarding the printhead or programming of motion and dispensing commands.

FIG. 14 further illustrates a binder liquid dispenser 1450 for dispensing binder liquid onto the build bed during a subsequent step of the 3DP process. This binder liquid dispenser 1450 may be mounted onto the same printhead 1440 and motion control system as the suspension dispensers 1410 and 1420, although it does not have to be.

Dispensing of suspension may be performed using in general any suitable type of dispenser or printhead that is appropriate to the particular example just given.

Dispensing of suspension may be performed with a piezoelectric drop-on-demand printhead. Such a dispenser may be designed to have a relatively straight-through flow path having smoothly-varying cross-section, such as may be achieved with a cylindrical-squeeze piezoelectric element, so as to provide as little opportunity as possible for suspended particles to accumulate in isolated places such as corners which might be out of the main path of fluid flow.

Dispensing of suspension may also be performed with a dispenser that uses small solenoid-operated valves such as microvalves available from The Lee Company (Essex, Conn.). Dispensing of suspensions through such valves has been demonstrated in commonly assigned patent application ("Printing or dispensing a suspension such as three-dimensional printing of dosage forms," filed Nov. 21, 2001, U.S. Ser. No. 09/991,556). Suspensions dispensed through microvalves may have to be limited to a smaller value of solids content than the solids content of suspensions dispensed with some of the other dispensing technologies.

One possible mode of microvalve dispensing is to dispense by a succession of brief discrete valve openings, which can be considered drop-on-demand operation. A succession of brief discrete valve openings provides a succession of individual drops if fluid conditions are appropriate, or in some cases provides a succession of fluid packets that may be connected by narrower fluid regions or other fluid geometry. Another possible mode of dispensing with microvalve dispensers, called line-segment printing, is a mode in which a valve opens and remains essentially fully open for as long as needed. In this case the dispensed fluid structure may resemble a steady jet.

Any of these dispensing technologies can be used either with multiple commonly aimed nozzles or with multiple separately aimed nozzles. For the technique involving variation of composition through a given nozzle, microvalves may be used.

It has been described that the powder suspended in the first suspension and the powder suspended in the second suspension are in some way of differing composition. It should be understood that each of those suspension powder compositions may individually be somewhat complicated. For example, the powder particles in an individual suspension do not have to all be identical to each other or even be a pure substance. For example, the powder particles in an individual suspension composition may be a mixture of powder particles of more than one substance. It is further possible that an individual powder particle may contain within itself more than one substance. For example, substances of interest in bone applications are the closely related substances hydroxyapatite and tricalcium phosphate, which can transform from one to the other under appropriate conditions of temperature and chemical environment. The same statements apply to the second suspension composition. In the present invention the overall composition of the powder of the first suspension is in some way different from the composition of the powder of the second or additional suspension, and the respective suspensions can each be deposited in predetermined locations during the formation of a powder layer for use in 3DP.

FIG. 15 is a top view of one pattern of deposition of two suspensions 1510, 1520 used to create a biostructure having an approximately circular central region of one powder composition surrounded by a different powder composition in the rest of the deposited layer. It should be remembered that this illustrated pattern is the pattern of powder composition, and the pattern of what material actually is present in the finished part would be determined by the pattern of the dispensing of the binder liquid onto the illustrated layer. This dispensing of binder liquid would take place onto the illustrated layer at a later step, and the shape of the pattern of dispensed binder liquid is not shown here.

This suspension-dispensing pattern illustrated in FIG. 15 could be produced by any of the already described methods. In the exemplary embodiment, the motion of the dispenser in a back-and-forth raster pattern 1530 is shown by a dotted line. Deposition of the suspension is illustrated as a series of circles such as might be impact points if individual drops of suspension were being dispensed, although in practice there would probably be more merging of individual droplet impacts upon the build bed (not shown).

FIG. 15 also illustrates a region of motion at each end of the raster pattern that is not used for deposition of slurry onto the build bed due to the possibility of non-ideal motion at the turn-around is shown. The unused end regions could be longer than shown in the illustration. It is also possible that the pattern of dispensing could be slightly larger than the build bed but still not occupy the entire turn-around region as shown. It would also be possible to have motion always in one direction during dispensing, i.e., dispense while moving in one direction, shut off while moving back, and repeating. Motion in other patterns, including vector motion, is also possible.

Further Steps

After the deposition of a layer by suspension deposition, carrier fluid may be allowed to percolate downward into the build bed, possibly with the help of a porous substrate underlying the build bed. A drying process with application of heat may be used, if desired, to accelerate evaporation of carrier fluid that does not percolate downward. When a layer of suspension-deposited powder is sufficiently dry, binder liquid comprising one or more binder substances may be dispensed onto the layer of powder in places selected so as to form the desired biostructure. The steps may then be repeated as needed. The pattern of composition of powder in any particular layer may differ from the pattern in other layers. When an entire biostructure has been manufactured and dried, the unbound powder may be removed from it as is known in the art.

In some instances, such as in the case of a biostructure made out of hydroxyapatite and tricalcium phosphate, after completion of the 3DP process there may be further processing steps. Such processing steps may comprise heating to a sufficient temperature and for a sufficient time to cause the decomposition and escape of the binder substance(s) deposited during the 3DP process (such as heating to 400 C for 1 hour), and may further comprise heating to a sufficient temperature and for a sufficient time to achieve partial sintering or sintering of the powder particles directly to each other, thereby achieving some mechanical strength.

A suitable sintering protocol can achieve all of the following: partial sintering of hydroxyapatite particles to themselves; partial sintering of tricalcium phosphate particles to themselves; and partial sintering of hydroxyapatite particles and tricalcium phosphate particles to each other. Such a suitable sintering protocol is sintering at 1350 C for 2 hours. A biostructure processed to this stage could be a porous all-ceramic biostructure and could be used as a bone substitute implant.

Alternatively, with such a biostructure there may be still further processing steps such as filling the pores either fully or partially with an interpenetrating substance. The joined powder particles may form a network, and the spaces not occupied by the joined powder particles may form another network that interlocks with the network formed by the joined powder particles. The interpenetrating material may either fully or partially fill that second network.

The interpenetrating material may be a polymer, which may be either nonresorbable or resorbable. An example of a nonresorbable polymer is polymethylmethacrylate. Examples of resorbable polymers are poly lactic acid and poly lactic co-glycolic acid. It is also possible, either instead of or subsequent to filling with an interpenetrating material such as a polymer, to fill open spaces with bioactive materials such as cells, cell fragments, cellular material, proteins, growth factors, hormones, Active Pharmaceutical Ingredients, peptides and other biological or inert materials.

In other instances for either medical or non-medical applications, with any powder material system, it may not be necessary to burn out the binder substance and perform sintering or partial sintering, but rather the binder substance may be left as part of the finished biostructure. In such a case, it still may be of interest to fully or partially infuse the biostructure with a polymer or a bioactive substance or both.

Further Discussion with Regard to Suspension Powder Composition

It has been described that the powder suspended in the first suspension and the powder suspended in the second suspension are in some way of differing composition. It should be understood that each of those suspension powder compositions might individually be somewhat complicated. For example, the powder particles in an individual suspension do not have to all be identical to each other or even be a pure substance. For example, the powder particles in an individual suspension composition may be a mixture of powder particles of more than one substance. It is further possible that an individual powder particle may contain within itself more than one substance. For example, substances of interest in bone applications are the closely related substances hydroxyapatite and tricalcium phosphate, which can transform from one to the other under appropriate conditions of temperature and chemical environment.

Further, it is believed that within a single powder particle there may be a number of grains defined by grain boundaries. It is believed that in a powder particle which began as a pure substance configured as multiple grains all of a single substance within a single particle, the matter within individual grains may individually transform from one substance to the other substance, resulting in a powder particle which itself contains some of each substance. Thus, the first suspension composition can comprise more than one kind of powder particle and even individual powder particles can comprise more than one chemical species or substance. The same statements apply to the second suspension composition. In the present invention the overall composition of the powder of the first suspension is in some way different from the composition of the powder of the second or additional suspension, and the respective suspensions can each be deposited in predetermined locations during the formation of a powder layer for use in 3DP.

The dispensed suspension as it travels from the nozzle(s) to the build bed may take the form of discrete drops, a continuous jet, an interrupted jet also known as line-segment printing, a series of fluid packets connected by narrower fluid regions, drops with satellite drops, or in general any fluid configuration.

Whatever the type of dispenser, dispensing may be performed such that essentially all places on the build bed receive approximately the same amount of dispensed suspension (per unit area) as any other place on the build bed, regardless of which dispenser or suspension source the locally dispensed suspension came from.

It should be appreciated that any action described as involving the use of or switching between two different suspensions of differing composition could also be similarly performed so as to involve more than two suspensions of respective different compositions. It has been described that a material pair of interest is hydroxyapatite and tricalcium phosphate, but it should be understood that the present invention could be used with any combination of any number of any dissimilar powder materials. The methods and systems of the present invention may be useful for manufacture of any type of biostructure, including both medical and non-medical articles, by 3DP.

The suspension deposition system of the present invention may be mounted on the same motion control system as the printhead that dispenses binder liquid, but it does not have to be. The reservoirs of suspension could be on the moving printhead where the nozzle(s) are located, or could be stationary. It is also possible for the build bed to move instead of or in addition to the nozzle(s). It should be understood that any of the described suspension deposition systems could be duplicated in the sense that more than one of them could operate over different regions of a build bed simultaneously. Each of the multiple dispensers or nozzles could have its own program or dispensing instruction. For example, multiple jets or nozzles or dispensers side-by-side or parallel to or near each other could be used.

It is known that when suspension is dispensed by a dispenser moving in a raster pattern, the final surface of the deposited layer after percolation and drying can exhibit a scalloped appearance corresponding to the raster pattern in which slurry was deposited. It is also known that this "scalloping" of the surface can be somewhat reduced by staggering the raster pattern in alternate layers, i.e., depositing lines for the next layer in the valleys of the previous layer.

The technique of staggering can be used with the present invention. Because in the present invention the selection of suspension composition must be coordinated with spatial location of the nozzle, implementing staggering would require an adjustment in the programmed pattern for deposition of individual suspension compositions, to account for the spatial offset in some layers relative to other layers. For example, the pattern of which slurry composition is dispensed where, during given passes, may change as a result of the shifting such as shifting by one-half of the line-to-line spacing of a raster. This can be taken into account in the controls and programming of the 3DP system. The present invention could also be used with other motion patterns for motion of the dispensers during deposition of the layer, such as vector motion.

The described technique of shutting off of suspension flow outside the build bed could be used even for manufacturing a part from a single-composition powder, such as an expensive powder. Aspects of the invention include timing of the turn-on and shut-off to minimize waste of powder due to dispensing of suspension when the nozzle or dispenser is outside the build bed. It is possible to shut off the dispensing most of the time when the nozzle or dispenser is outside the build bed. However, even if the dispensing is mostly shut off when the nozzle or dispenser is outside the build bed, there still may be reason to dispense small amounts of suspension outside the build bed. One reason may be to correct for evaporation of liquid suspension which may have an unintended composition as a result of evaporation of liquid from suspension which has been at the tip of the dispenser for a period of time, by dispensing and discarding that suspension and bringing fresh suspension to the tip of the dispenser. A related reason may even be to prevent clogging of the dispenser by dispensing liquid suspension that has been at the tip of the dispenser for a period of time.

The depositing of a powder layer has been described in connection with three-dimensional printing. However, this should also be considered an aspect of the present invention which is useful in its own right and which can be used in applications such as selective laser sintering and other methods of manufacturing from powder.

Location-specific Solid Powder Composition by Chemical Reaction

Spatial variation of composition of the solid can also be achieved by chemical reaction. These variations of composition may comprise multiple discrete regions (which may be of irregular shape) within the biostructure, each having different composition.

In one embodiment of the present invention, the biostructure is a bone substitute that is exceptionally well suited for the human body, by virtue of its achievable composition detail such as having both regions of a first composition such as hydroxyapatite, and regions of a second composition such as tricalcium phosphate, together with other features such as macrostructure, mesostructure and microstructure. The two substances are capable of being converted from one to the other by a chemical reaction. The powder particles in the biostructure may be partially sintered to each other. The biostructure may further include polymer and/or bioactive substances.

Hydroxyapatite and tricalcium phosphate both occur in natural bone. Hydroxyapatite is generally considered to be nonresorbable by the human body. Tricalcium phosphate is resorbable by the human body over a time period of months. Other calcium-phosphorus compounds are also resorbable. Hydroxyapatite and tricalcium phosphate are characterized and distinguished from each other by the ratio of calcium atoms to phosphorus atoms present in the material. The chemical formula for tricalcium phosphate (TCP) is $Ca_3(PO_4)_2$. TCP therefore has a Ca/P ratio of 1.5. The chemical formula for hydroxyapatite is (HA) is $Ca_5(PO_4)_3OH$. HA has a Ca/P ratio of 1.67. HA is calcium-rich, at least compared to TCP.

Hydroxyapatite can be converted to tricalcium phosphate by a chemical reaction. A typical reaction for this conversion involves supplying extra phosphorus to the hydroxyapatite and also extra oxygen. The extra phosphorus can be supplied in the chemical form of phosphoric acid, or ammonium phosphate, or an organic phosphate, or a phosphate salt such as a metal phosphate. The extra oxygen can come from the surrounding atmosphere.

The reaction takes place at elevated temperature. In the case of phosphoric acid and organic phosphates and other organic compounds, the carbon and hydrogen and other organic components can be expected to leave the biostructure at elevated temperature as gaseous decomposition products. In the case of metallic phosphates, it is likely that the metallic ions will remain permanently in the biostructure. It is also possible to convert tricalcium phosphate to hydroxyapatite by means of a reaction involving a reactant containing extra calcium. For parts that are going to be heated to a high temperature for sintering, it is possible to simply add a reactant that has a Ca/P ratio different from that of the main powder, and know that during the high temperature treatment, a chemical reaction will take place that will adjust the Ca/P ratio of the aggregate. For ceramics, this chemical conversion reaction takes place at high temperature, a temperature that may be used for sintering. For example, to end up with a final composition that has a higher Ca/P ratio than the main powder, include a reactant that has a higher Ca/P ratio than the main powder, i.e., is calcium-rich. To end up with a final composition that has a lower Ca/P ratio than the main powder, include a reactant that has a lower Ca/P ratio than the main powder, i.e., is calcium-deficient or phosphorus-rich (this can even be a powder which contains phosphorus while containing no calcium at all).

The following is a list of possible reactants along with their respective Ca/P ratios:

| Possible starting powder: | | |
| --- | --- | --- |
| Hydroxyapatite | $Ca_5(PO_4)_3OH$ | Ca/P = 1.67 |
| Possible desired end state | | |
| Tricalcium Phosphate | $Ca_3(PO_4)_2$ | Ca/P = 1.5 |

Calcium-deficient (phosphorus-rich) possible reactants (Ca/P ratio less than 1.67)

| DiCalcium Phosphate | CaHPO4 | Ca/P = 1 |
|---|---|---|
| Monocalcium phosphate | Ca(H2PO4)2 *H2O | Ca/P = 0.5 |
| Phosphoric Acid | H3PO4 | Ca/P = 0 |
| Ammonium phosphate | NH4(H2PO4) | Ca/P = 0 |

(It can be noted that the name DiCalcium Phosphate comes from Dibasic Calcium Phosphate and does not imply that the number of calcium atoms in the molecule is two. DiCalcium Phosphate (in anhydrous form) is CaHPO4.)

Calcium-rich possible reactants

| Calcium carbonate | CaCO3 | Ca/P = infinity |
|---|---|---|
| Calcium oxide | CaO | Ca/P = infinity |
| Calcium hydroxide | Ca(OH)2 | Ca/P = infinity |

In addition to the above reactions, there are others. The substance used for the reactant depends on which if any ions are considered acceptable in the final product. Upon exposure to high temperatures and reaction, organic ions such as ammonium or carbonate can be expected to form gaseous products which leave the article. Ammonium ion will exit as ammonia gas, and carbonate will exit in the form of carbon dioxide gas. Organic compounds, involving carbon, can also be expected to decompose in such a way that the carbon leaves as carbon dioxide gas. There are also possible reactants that may contain other ions such as magnesium, sodium and potassium. It is likely that such ions will not exit from the article as gaseous reaction or decomposition products, but rather will remain in the article. Such ions may be acceptable in a final biostructure that is a bone substitute, because such ions do occur in natural bone. There are other inorganic ions that are probably less acceptable (silicon, for example) or unacceptable to remain in a finished product.

The following are exemplary methods of making TCP:
1. HA+add phosphorus to produce TCP
2. HA+calcium-deficient reactant to produce TCP For example, HA+DiCalcium Phosphate to produce TCP Additionally, to make TCP starting from substances other than HA, such as DiCalcium Phosphate+add calcium to produce TCP. Further, DiCalcium Phosphate+CaCO3 produces TCP. It is also possible to start with TCP powder and use a chemical reaction to make HA (although, HA has better repeatability and manufacturing sources for consistent properties). Additionally, HA can be made from TCP by TCP+(a calcium-rich reactant having Ca/P greater than 1.5) gives HA. It is also possible to start from substances other than TCP and make HA.

It can be noted that only a small change in the Ca/P ratio will result in a larger change in the composition ratio HA/TCP. For example, a Ca/P ratio of 1.67 corresponds to 100% HA, but a Ca/P ratio of 1.64 corresponds to a composition of 85% HA, 15% TCP.

This has been described mainly in terms of starting with HA powder because the techniques for producing powder of consistent properties (e.g., CeraMed, Lakewood, Colo.) are known even though expensive.

The techniques described are not confined to just printing a reactant onto a powder or just mixing powder. Similar principles could be used for making other phosphorus compounds and even BioGlass.

There are two crystal forms of TCP, designated alpha-TCP and beta-TCP. Both forms resorb in the human body, but alpha-TCP resorbs at a faster rate than the bone growing in to replace it. For that reason, evidence suggests that beta-TCP is better to have in a resorbable product. The relative fractions of each crystal orientation produced from a process such as the present invention seem to depend on the sintering temperature. A sintering temperature of 1000 C is low enough to produce beta-TCP and avoid the transformation to alpha-TCP. A sintering temperature of 1350 C produces essentially all alpha-TCP.

It may be estimated that the boundary temperature between temperatures that give mostly beta-TCP and temperatures which give mostly alpha-TCP is 1125 C or 1150 C. Thus, relatively low sintering temperatures are useful if beta-TCP is what is desired. However, lower sintering temperatures also generally give lower mechanical strength. There are also other variables such as particle size that can be chosen so as to influence mechanical strength.

To make HA from TCP, preferably, the Ca/P of the additive should be greater than 1.67 (not just greater than 1.5). As an example, mixing TCP (1.5) with some amorphous calcium phosphate with Ca/P of 1.6 (>1.5), would not yield HA, as the resultant Ca/P is not near that of HA, namely, 1.67. In short, the additive needs to exceed the target Ca/P to make up for initial deficiency.

Method of Location-specific Solid Powder Composition by Chemical Reaction

Another aspect of this embodiment of the present invention provides a method for creating the biostructure having variation of composition that includes spreading only one composition of powder in the form of a layer, and dispensing onto that powder in selected places a reactant that upon application of heat is suitable to convert the powder to a second substance. Alternatively, the layer of powder containing more than one powder composition could contain powder that is deposited in specific locations to create the mixed layer.

In the present invention, layers of powder particles of a single material are deposited by any suitable means. This can include dry spreading by roller, or deposition by slurry deposition or hand rolling. The powder may be all of one composition. The composition could be hydroxyapatite, or alternatively tricalcium phosphate.

In one embodiment, the layer of powder may be deposited is by suspension deposition. The powder particles in the suspension may be selected so as to be suitably small so as to have a high likelihood of remaining in suspension. Suitable additives to the carrier liquid, such as steric hindrants or suspending agents or surfactants, may be included to help keep the particles in suspension, such as by preventing them from agglomerating. Typical additives may be added to the carrier liquid to promote suspension.

A typical powder particle size is 20 microns or smaller. Percolation means such as a porous substrate underlying the build bed may be used to promote the drainage of the carrier liquid, as is known in the art. Application of external heat may be used to accelerate the evaporation of the suspension carrier liquid after deposition of a layer has been completed (referred to herein as interlayer drying).

When the powder in the uppermost deposited layer is sufficiently dry, the binder and/or reactant as described later may be deposited. If the powder is deposited by slurry, the carrier liquid of the suspension, and the binder substance or substances used for the 3DP process, may be chosen so that the binder substance or substances are not excessively soluble in the slurry carrier liquid. This assures that deposition of suspension for subsequent layers may be performed without appreciably affecting the binding of already-printed layers. For example, the binder substance may be polyacrylic acid and the suspension carrier liquid may be isopropanol or water. Polyacrylic acid is somewhat soluble in isopropanol and water, but not excessively soluble.

If the powder is deposited by roller spreading, the powder would be dry and of a larger particle size. After deposition of a layer of powder, a binder liquid that may comprise one or more binder substances may be dispensed onto that layer in selected places to bind powder particles to each other and to other bound regions. The whole sequence may then be repeated as many times as needed. Possible subsequent processing steps are described later.

The invention may use piezoelectric drop-on-demand dispensers, or microvalve dispensers in either of two modes, or continuous-jet-with-deflection dispensers or other types. It may include several post-processing steps such as binder burnout, sintering, reaction, and possible infusion with polymer and possible infusion with bioactive substances.

In one embodiment, the powder spread to form the layer may be pure hydroxyapatite. The dispensing of binder liquid during three-dimensional printing may include dispensing, in selected places, a binder liquid that comprises a substance suitable for converting HA to TCP. After the completion of 3DP and subsequent harvesting and dedusting, the printed biostructure may be heated to a temperature appropriate to promote the reaction between HA and the substance that results in formation of TCP.

In other places where the final biostructure is desired to include HA, a different binder may be printed which binds powder particles together but does not include the substance which converts HA to TCP. The final result, after heat treatment, is a biostructure in which the HA has transformed at least partially into TCP in the places where substance was printed or dispensed, and remains HA in other places.

In connection with the use of such a system, at least one of the dispensers will be turned off at any given time, and sometimes both of them may be turned off. "Off" periods are times when evaporation of liquid may occur at the tip of the dispenser. This may result in a localized increase of concentration at the tip of the dispenser which is different from what is intended, and may even cause a clog. Accordingly, it may be desirable to occasionally operate the dispenser at certain times when it is not over the build bed so as to dispense small amounts of liquid from the dispensers sufficient to restore as-mixed composition to their tips, or to prevent clogging.

It is also necessary to dispense a binder substance for the purpose of adhering powder particles to each other. It is possible that the binder substance is not the same substance as the reactant. The binder substance may, for example, be polyacrylic acid. When the binder substance and the reactant are different substances, there are two possibilities for dispensing them. One possibility is that the two substances can be mixed together in a single binder liquid. The other possibility is that they are dispensed from separate dispensers. In general, the places where it is desired that binder be deposited may not be exactly the same places where it is desired that reactant is deposited. It may be necessary that in some places only binder be deposited, and in other places both binder and reactant be deposited. It is in general not necessary to deposit reactant only, because such places would be outside the finished part.

Accordingly, there may be at least two dispensers. One dispenser may dispense binder only and the other may dispense reactant only. Alternatively, one dispenser may dispense binder only and the other may dispense a combination of both binder and reactant. Of course, it could also be arranged to dispense different amounts of reactant in different places. The two dispensers which may be mounted on part of a single printhead or they do not have to be.

A sintering protocol may be used which is simultaneously appropriate for all of the following: partial sintering of hydroxyapatite particles to themselves; partial sintering of tricalcium phosphate particles to themselves; and partial sintering of hydroxyapatite particles and tricalcium phosphate particles to each other.

Dispensing of suspension may be performed using in general any suitable type of dispenser or printhead that is appropriate to the particular example just given as described in greater detail above.

Further Steps

After completion of the manufacturing process, there may be further processing steps. Such processing steps may include heating to a sufficient temperature and for a sufficient time to cause the decomposition and escape of the binder substance(s) deposited during the 3DP process (such as heating to 400 C for 1 hour), and may further include heating to a sufficient temperature and for a sufficient time to cause the reaction of the reactant with the powder, and may further include heating to a sufficient temperature and for a sufficient time to achieve partial sintering or sintering of the powder particles directly to each other, thereby achieving additional mechanical strength.

A suitable sintering protocol can achieve all of the following: partial sintering of hydroxyapatite particles to themselves; partial sintering of tricalcium phosphate particles to themselves; and partial sintering of hydroxyapatite particles and tricalcium phosphate particles to each other. Such a suitable sintering protocol is sintering at 1350 C for 2 hours. A biostructure processed to this stage could be a porous all-ceramic biostructure and could be used as a bone substitute implant.

Alternatively, with such a biostructure there may be still further processing steps such as filling the pores either fully or partially with an interpenetrating substance. The joined powder particles may form a network, and the spaces not occupied by the joined powder particles may form another network that interlocks with the network formed by the joined powder particles. The interpenetrating materials may either fully or partially fill that second network as is described in more detail below.

Further Discussion Regarding Changing Solid Composition through Chemical Reaction The invention has been described here with respect to the HA/TCP material system, but it should be understood that other material systems that are chemically convertible from one material to another could also be used.

It is believed that within a single powder particle there may be a number of grains defined by grain boundaries. It is believed that in a powder particle which began as a pure substance configured as multiple grains all of a single substance within a single particle, the matter within individual grains may individually transform from one substance to the other substance, resulting in a powder particle which itself contains some of each substance. Thus, the first suspension composition can comprise more than one kind of powder particle and even individual powder particles can comprise more than one chemical species or substance.

It is also possible that an entire biostructure could be manufactured from hydroxyapatite and the entire biostructure could be completely converted to tricalcium phosphate, or the entire biostructure could be converted to tricalcium phosphate to a desired extent, by heating to an appropriate temperature for an appropriate time. In this case there would be no place-to-place variation of composition among regions of the biostructure. No reactant would be involved.

It is also possible that, by means of chemical reaction, the entire biostructure could be converted completely or to a desired extent, without any location-specific composition variation. The entire structure could be soaked in a reactant and later reacted. This could be done after other post-processing steps such as sintering, or at other appropriate times.

The suspension deposition system of the present invention may be mounted on the same motion control system as the printhead that dispenses binder liquid, but it does not have to be. The reservoirs of reactant and binder, or reservoirs of binder and (reactant+binder) combination, could be on the moving printhead where the nozzle(s) are located, or could be stationary. It is also possible for the build bed to move instead of or in addition to the nozzle(s). Multiple printheads or multiple dispensers on a given printhead could be used.

It is also possible that in certain instances, the invention could be used without a binder substance. A mold may be used to provide external shape, powder could be stacked, and reactant could be deposited in desired places, and the entire powder could be post-treated such as with heat to cause the reaction, heat to partially sinter, etc.

The invention is described but in no way limited by the following Examples:

EXAMPLE 1

Location-Specific Powder Veposition By Chemical Reaction

Preparation of ? ? CP/HA biphasic bars.

A method to convert HA to beta-TCP was tested. Bone bars made from hydroxyapatite powder were soaked in different concentrations (0.2 M to 1 M) of $(NH_4)_2HPO_4$ at room temperature for 24 hours. After being dried at 70 C for 48 hours, the hydroxyapatite bars were sintered at 1300C for 2 hours. Various ratio of beta-TCP/HA were obtained. A 100% beta-TCP was obtained with the sample soaked in 1 M $(NH_4)_2HPO_4$.

An experiment was performed using sintered HA bars (20 micron average particle diameter, /1000 C pre-sintering temperature, sintered at 1350C for 2 hours). FTIR (Fourier Transform InfraRed spectroscopy, SEM (Scanning Electron Microscopy), XRD (X-Ray Diffraction) and mechanical testing were performed to characterize the samples.

The following table listed the results from experiment:

A. Table. XRD and mechanical tests results

| $(NH_4)_2HPO_4$ Concentration (M) | Sintering condition | Composition of the bar (percentage) | | | Flextural Strength (MPa) | |
|---|---|---|---|---|---|---|
| | | ? ? CP | ? ? CP | HA | Avg. | Standard TDeviation |
| 0.2 | 1300° C., 2 h | 2.9 | 0 | 97.1 | 4.7 | 1.5 |
| 0.3 | 1300° C., 2 h | 9.0 | 0 | 91.0 | 5.6 | 0.9 |
| 0.5 | 1300° C., 2 h | 25.5 | 0 | 74.5 | 6.8 | 1.5 |
| 0.7 | 1300° C., 2 h | 22.0 | 0 | 78.0 | 6.5 | 2.5 |
| 1 | 1300° C., 2 h | 35.2 | 0 | 64.8 | 5.5 | 2.8 |
| 2 | 1100° C., 2 h | 0 | 35 | 65 | 5.3 | 0.7 |
| 2 | 1300° C., 2 h, then 1100° C., 2 h | 32 | 15 | 53 | weak | |

The results illustrate that sintering temperature and the concentration of $(NH_4)_2HPO_4$ will affect the composition of the final bar. Higher $(NH_4)_2HPO_4$ concentration is favorable for obtaining TCP phase, while higher sintering temperature (1300° C.) is favorable for ?-TCP formation. Lower sintering temperature will result in the formation of ?-TCP. In most cases, the bars can still have good strength.

SEM pictures showed that HA crystal and crystal boundary, which are commonly seen in sintered HA particles, can still be seen on all particles in all treatments except the 2M 1100° C. sample. The 2M 1100° C. bar showed a quite different surface morphology. The surface of the particles becomes rougher, possibly suggested that more ?-tcp was presented on the surface of particles.

FTIR spectra showed there is no significant difference with lower (<1 M) $(NH_4)_2HPO_4$ concentration. Significant changes were observed in high $(NH_4)_2HPO_4$ treatment after sintering. The 2M 1100° C. sample clearly showed some b-TCP peaks.

EXAMPLE 2

Chemical treatment and resintering—"post-processing."

This approach starts with parts after printing and sintering, and includes infiltration-type chemical treatment, drying, and resintering. The strategy tested so far has been to take our existing HA parts and perform the chemical treatment with a phosphate source in solution (ammonium phosphate, phosphoric acid, etc.), and sinter the parts a second time. The idea here is that we are adjusting the calcium to phosphorus ratio of the part from that of HA (1.67) toward TCP (1.50), and providing enough energy during the second firing for the material present to rearrange itself chemically into the desired species.

Experiments with phosphoric acid have demonstrated the feasibility of transformation into both alpha- and beta-TCP. The beta-TCP was obtained by sintering at lower temperature than alpha-TCP (1000C vs. 1350C).

EXAMPLE 3

Initial Powder Selection

This approach is similar to Experiment 2 above in terms of manipulation of the calcium to phosphorus ratio and sintering the part, but the reagents are the initial powder blend used for printing, and there may only be one sintering step involved.

In the following experiment, HA was mixed with DCP (dicalcium phosphate, Ca/P of 1.00) prior to printing and sintering at 1350 C. This experiment produced a fairly large amount of alpha-TCP and was deemed successful.

Additional experiments may look at other starting powders besides HA. For example, other starting powders besides HA could include: calcium carbonate+DCP converted to TCP or HA; or calcium hydroxide+DCP converted to TCP or HA.

DCP is not highly water soluble. A non-water-soluble reactant could therefore be dispensed from a printhead as a suspension as described herein. For example, HA suspension/slurry may be deposited in some places and spots of the reactant may be deposited in other places. Alternatively, a whole layer of HA may be spread and the reactant could be suspension-print desired using techniques as described herein. In a post-processing step, the biostructure would be heated or sintered to cause the reaction to take place. This Example combines two approaches discussed herein, namely, mechanical localized deposition or slurry deposition followed by chemical reaction.

Material Composition—Partial Infusion of the Porous Biostructure Material Composition: Infusion of the Porous Biostructure In addition to the material(s) of which the particles are made, the biostructure also may comprise various other substances from a variety of categories. These other substances may occupy spaces between the powder particles, filling those spaces either partially or completely.

For a sintered biostructure, or a biostructure comprising demineralized bone, or a biostructure made of polymer as a primary material, or any other kind of biostructure, it is possible, at least with certain manufacturing methods, that the powder and the binder substance taken together do not occupy all of the space within the biostructure. Accordingly, the biostructure may further contain still other substances. One category of such substances is substances to increase the mechanical strength of the biostructure, such as fibrin or a polymer, examples of which are given herein. This substance may vary in amount or composition from one place to another in the biostructure. More than one such substance may be used.

Alternatively, another category of substance that may be included in the biostructure in addition to powder and binder substance is a bioactive substance. Bioactive substances that can be readily combined with the bone particles are described below in greater detail.

It is further possible that in a biostructure that contains powder particles and binding substance(s) and strengthening substance(s), there still may be room for other substances. Such substances could be bioactive substances, examples of which were just given. Such substances may vary in amount or composition from one place to another in the biostructure, and more than one such substance may be used.

As discussed below, it is also possible that a dissolvable material could occupy the portions of the biostructure, such as to provide a strengthening or handling-protection effect that goes away quickly upon installation of the biostructure in the body. This substance may vary in amount of composition from one place to another in the biostructure, and more than one such substance may be used.

In general, it is possible for any component of the biostructure to have different composition from one place to another within the biostructure, and for more than one composition of any category of substance to be used. The powder composition can vary. The binder substance can vary in composition or concentration from place to place within the biostructure. The composition or concentration of strengthening substance, bioactive substance, soluble substance or other substance to vary from place to place within the biostructure.

Resorbability means that materials will not persist indefinitely in the human body, but rather will be chemically changed and eliminated. It may be desirable for all or at least some of the material components of the biostructure to be resorbable. Of the various materials mentioned, hydroxyapatite and some polymers such as polymethylmethacrylate (PMMA) are non-resorbable. Most of the others are resorbable, including specifically DBM, various calcium phosphates, collagen, fibrin, and poly lactic co-glycolic acid (PLGA).

One category of such substances is substances to increase the mechanical strength of the biostructure, such as a polymer. The substance can be either resorbable or nonresorbable. Resorbability means that materials will not persist indefinitely in the human body, but rather will be chemically changed and removed from the implant by bodily fluids. It may be desirable for all or at least some of the material components of the biostructure to be resorbable. Examples of non-resorbable materials are hydroxyapatite and some polymers such as polymethylmethacrylate (PMMA). Examples of resorbable materials are Demineralized Bone Matrix, various calcium phosphates, collagen, fibrin, and poly lactic co-glycolic acid (PLGA).

Examples of resorbable polymers are starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, polyhydroxyalkanoates, poly(propylene glycol-co-fumaric acid), tyrosine-based polycarbonates, pharmaceutical tablet binders, polyvinylpyrollidone, cellulose, ethyl cellulose, micro-crystalline cellulose, and blends thereof. Examples of nonresorbable polymers are TEGDMA, UDMA, Bis GMA, polyacrylate, polymethyl methacrylate, polytetrafluoroethylene, polyurethane, and polyamide.

This strengthening substance may vary in amount or composition from one place to another in the biostructure. More than one such substance may be used. In mixtures of the materials PLA and PLGA, the relative proportions of each material can be tailored, along with their molecular weights, to provide desired resorption characteristics. Different polymers may be used in different places and filling of open space may be done to different degrees in different places.

One embodiment of the biostructure of the present invention comprises a matrix-material network such that the space not occupied by the matrix material forms a non-matrix-material network that interlocks with the matrix-material network. The matrix material, forming a first interconnected network, may have exposed internal surfaces of that network at least some of which may receive essentially a coating of the interpenetrating material. The matrix material together with its coating may form a second network, which may be designated the second interconnected network or the interpenetrant network. The interpenetrant network may be such that the spaces not occupied by it also form a network, which may be designated the third interconnected network. All of these networks may be three dimensionally interconnected, although they do not have to be. Additionally there may be other regions of the biostructure in which the interpenetrant network may be completely or almost completely filled with interpenetrating material. Gradual variation of the extent of filling by the interpenetrating material may be provided. The matrix-material or first network may be deterministically designed including features such as macrostructure, mesostructure, microstructure, channels (which may be curved), internal void spaces, and other features that may be complicated.

In the present invention, various materials are possible for each of the components. As has already been described briefly, materials can broadly be divided into the categories of resorbable materials and nonresorbable materials. The matrix material may be essentially any material and may be either resorbable or nonresorbable. The interpenetrating material(s) may be resorbable or nonresorbable. Any possible combination of resorbable or nonresorbable matrix material and resorbable or nonresorbable interpenetrant can be used. The interpenetrating material can be different in different portions of the biostructure.

As discussed herein, hydroxyapatite or Tricalcium phosphate may be used for the matrix material. Other resorbable compounds containing calcium and phosphorus could also be used. Other nonresorbable ceramics such as alumina could also be used. Other materials that could be used for the matrix material include other ceramics, demineralized bone matrix and material derived from coral and similar natural materials. Any of these materials or others, either resorbable or non-resorbable, could be used for the matrix material. The matrix could also be made of a polymer, such as is used in a scaffold for tissue engineering. The polymer may itself be either nonresorbable or resorbable. The polymer may exist in the geometric configuration of foam, gauze, mesh, and the like.

A particular category of polymer that may be used as the interpenetrating material is comb polymers. Comb polymers and copolymers (herein jointly referred to as comb polymers) are described in U.S. Pat. Nos. 6,207,749 and 6,207,749, which are incorporated herein by reference in their entirety. For example, known families of polymers, either resorbable or nonresorbable, can be formulated as comb polymers by retaining the basic structure or backbone of the polymer but substituting various ligands on the side chains of these molecules. Polymers such as polymeric lactic and glycolic acids can be formulated as comb polymers, as can polymethylmethacrylate. Although many ordinary polymers are somewhat hydrophobic, comb polymers (as well as other types of polymers) can be formulated to provide controlled hydrophobic or hydrophilic behavior.

Comb polymers can selectively either promote or discourage attachment by various biological molecules or cells. Comb polymers can even be formulated to migrate to a free surface of a material during hardening of that material. In the practice of the present invention, comb polymers may be used in any geometry or extent of interpenetration described herein, ranging from fully filling pores, to existing as a coating on a matrix-material network, or other form of partially filling pores, to partial filling one region along with fully filling another region or regions. Different comb polymers could be deposited in different regions of the ERB.

It is also possible that the interpenetrating material could be a combination of a polymer and a bioactive substance such as an Active Pharmaceutical Ingredient. These multiple materials could be co-deposited as described later.

In some applications, it is not necessary or even desirable that the biomedical biostructure be fully filled with interpenetrating material to the extent that every inter-particle void space is totally filled. Complete and total interpenetration may actually have disadvantages. There are known bioactive substances such as growth-promoting substances which can be delivered to the body by being soaked into porous regions of biomedical articles if the biomedical articles are porous, which would not be possible in a totally infused biostructure or region of a biostructure.

If the interpenetrating material is a member of the lactic acid polymer family, the degradation products of the interpenetrating material are lactic acid, and in general it is desirable to minimize the amount of lactic acid released into the body. Further, complete filling of the pores by resorbable interpenetrating material means that access by bodily fluids to interior regions is not available until some of the resorbable interpenetrating material resorbs, and cell in-growth cannot start until that happens. Thus, for a variety of reasons, it may be desirable to only partially rather than fully fill the void space with interpenetrating material.

Figure 16:
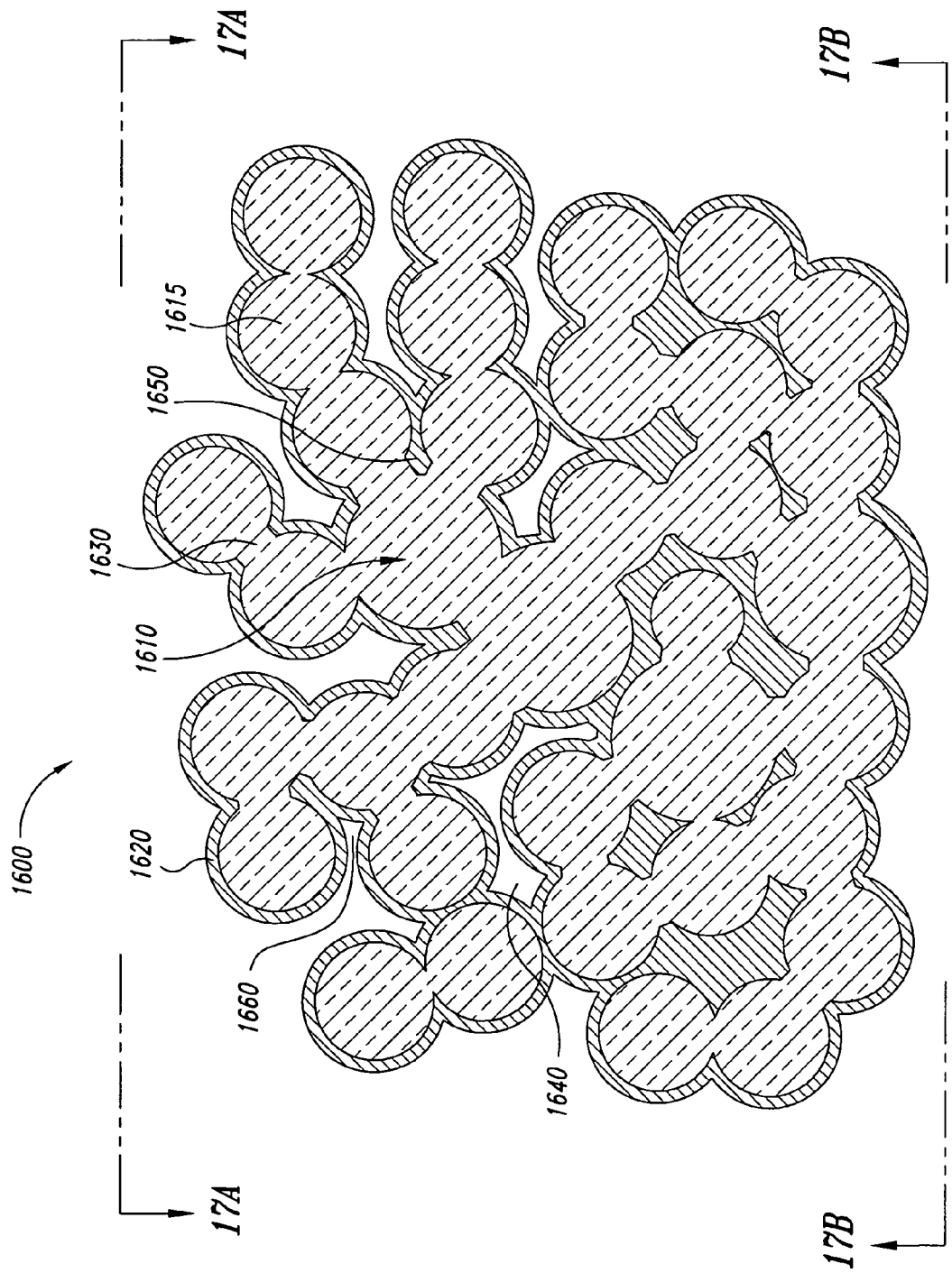
FIG. 16 is a cross sectional view of a partially infused engineered regenerative biostructure in accordance with principles of the present invention.

FIG. 16 is a cross sectional view of a partially infused ERB 1600. FIG. 16 illustrates the three interconnected networks of the present invention. In the exemplary embodiment, the matrix or first interconnecting matrix 1610 is made from powder particles 1615 that have been partially sintered together. The powder particles 1615 form a "neck" region 1630 where they are sintered together. The interpenetrating or second interconnecting matrix 1620 coats the matrix 1610 but does not fill all of the voids. The remaining pores shown as open in the exemplary embodiment form the third interpenetrating matrix 1640.

The shapes shown to represent the sintered state are portions of spheres representing those portions of spherical particles whose shape has not been significantly changed by sintering, along with small neck regions 1630 having concave curvature in at least one direction which connect the adjoining particles where those powder particles have formed joints to neighboring powder particles. This illustrates a partially sintered condition, wherein the connected particles still have some void spaces between them, as opposed to being fully coalesced eliminating all void space.

Figure 17A:
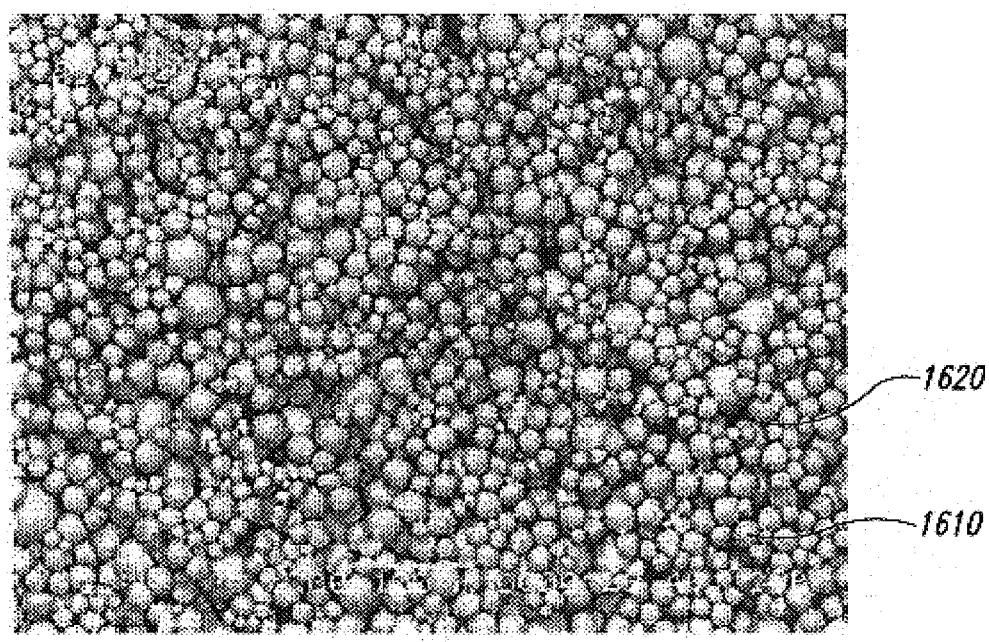
FIG. 17A is a cross sectional view of FIG. 16 along line 17A—17A.

In the upper portion of FIG. 16, the interpenetrating matrix 1620 is shown as forming essentially a coating or a thin surrounding region on the exposed surfaces of the first matrix network 1610. The coating is shown as being of approximately uniform thickness, although it does not have to be. It is possible that the interpenetrating material may fill some small pores and corners of the matrix network 1610. For example, corner 1650 is shown as being essentially filled by the interpenetrating material, and corner 1660 is shown as being partially filled by the interpenetrating material. However, at least some of the spaces, such as 1640, remain sufficiently open to form a network of space that is neither matrix material nor interpenetrating material. FIG. 17A is a cross sectional view along line 17A—17A of FIG. 16 illustrating a matrix 1610 partially filled by interpenetrating material 1620.

Figure 17B:
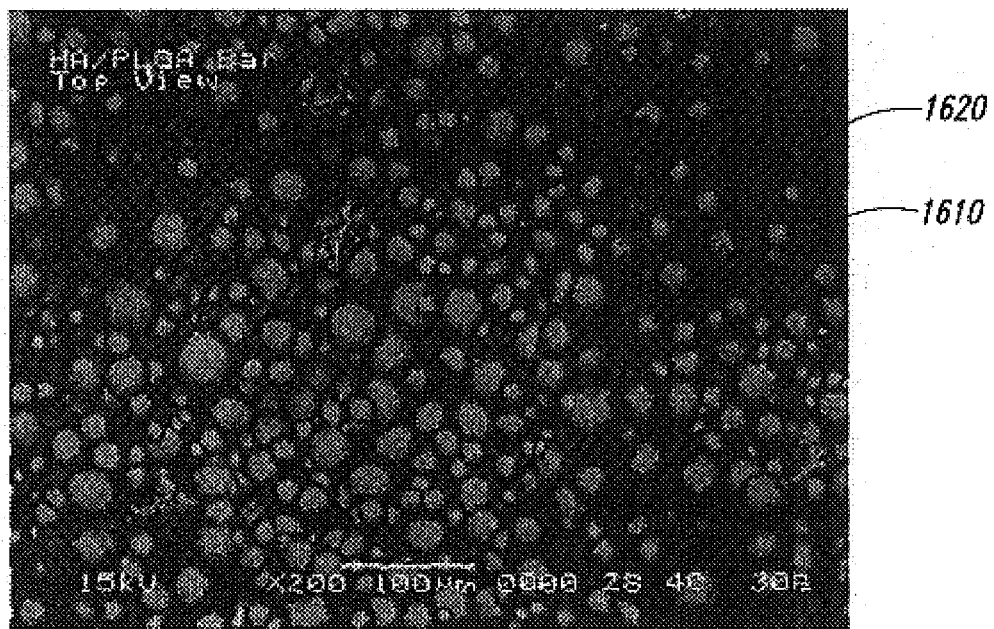
FIG. 17B is a cross sectional view of FIG. 16 along line 17B—17B.

In the lower portion of FIG. 16, the interpenetrating material 1620 is shown as filling essentially all of the space between powder particles 1615. The region in which the space between particles is essentially completely filled by interpenetrating material is shown as having a depth of approximately three powder particles, but other values are possible depending on the processing parameters and techniques as described herein. The biostructure may have an overall surface defining its exterior, and the region that is essentially completely filled with interpenetrating material may form some or all of the overall surface of the biostructure. FIG. 17B is a cross sectional view along line 17B—

17B of FIG. 16 illustrating a matrix 1610 completely filled by interpenetrating material 1620.

It is possible that the matrix-material network may be a natural material, such as material derived from coral, demineralized bone matrix, etc. It is also possible that the matrix material could be in a random form, or in the form of fibers that may interconnect with each other. In such cases, the microstructure may be slightly different from what has been described and illustrated in FIG. 16. It could be expected that the illustration corresponding to such other materials would have fewer identifiably nearly-spherical shapes making up the matrix-material network, but otherwise would have similar appearance and features and would still form a network. The features of the interpenetrating material would be similar.

In one embodiment of the invention, the third interconnected network of the biostructure may be empty space as illustrated in FIG. 16. Providing this empty space may provide a way for bodily fluids to access the interior of the biostructure and thereby the empty space of the network would facilitate resorption of the interpenetrant if the interpenetrant is resorbable, and also resorption of the matrix material if the matrix material is resorbable. Such access is not available when the pores are essentially entirely filled with interpenetrating material. Furthermore, as resorption of the interpenetrating material progresses, the empty space increases and access by bodily fluids further improves. In addition, such interconnected space, especially if it is of the appropriate dimension, may serve as a scaffold that encourages the ingrowth of natural bone or other tissue.

Alternatively, the third interconnected network may contain one or more bioactive substances (not shown). It may be desirable to include in the biostructure one or more biologically active or beneficial substances such as antibiotics, Active Pharmaceutical Ingredients, anesthetics, anti-inflammatory substances, growth promoting substances, hormones, proteins, growth factors, peptides, bone morphogenic proteins, cells or cell fragments, cellular material, other biological material, etc. These substances may occupy some portion or all of the third interconnected network. The bioactive substances may exist in the form of a liquid of appropriate viscosity, or a suspension, or a gel or a solid.

Eventually, after implantation of the biostructure, the bioactive substances may migrate out of the third interconnected network or be used up, and the third interconnected network may become available to provide access for bodily fluids to cause resorption of the interpenetrant if the interpenetrant is resorbable, and also resorption of the matrix material if the matrix material is resorbable. Newly grown bone or cartilage or other tissue may also occupy the third network.

Methods of Infusion

After the matrix-material network is created, the interpenetrating material may be introduced into it. In one embodiment, the interpenetrating material is placed into the pores of the matrix in selected regions of the biostructure, but not throughout. In another embodiment, more than one kind of interpenetrating material is placed in the biostructure. In yet another embodiment, the interpenetrating material may enter the pores as a liquid, some of the liquid may be drained or removed thereby leaving some empty space, and then whatever interpenetrating material remains may solidify.

For embodiments in which different regions are desired to have different degrees of infusion, it is possible to arrange that some of the liquid drain from some regions, and to arrange for poorer drainage of the liquid to form the region which is to be more fully occupied by interpenetrating material. It is also possible, if desired, to perform multiple repetitions of the above process of filling the pores with a liquid, followed optionally by drainage, followed by solidification, thereby achieving a greater degree of filling of the empty space in regions where this is repetitively performed. The biostructure can be dipped or infused by any of the disclosed methods such as to infuse a certain infusing material into one portion and then can be reoriented and the biostructure can be dipped or infused with a different substance or with the same substance so as to concentrate the interpenetrant at a different orientation.

One such method of depositing interpenetrating material involves dissolution followed by solidification by evaporation from a solution. The interpenetrating material may be partially placed into the empty space of the matrix-material network by dissolving the interpenetrating material in a liquid solvent to form a solution; then allowing or causing the solution to move into at least some of the empty space of the matrix-material network; then optionally allowing or causing some of that solution to drain from at least some of the empty space thereby leaving the exposed surfaces of matrix material wetted while also still leaving some empty space; at the same time, optionally allowing or causing some regions to remain essentially completely filled with liquid; and then allowing or causing the solvent to evaporate, thereby leaving behind the interpenetrating material partially occupying the non-matrix-material network.

In the case of an interpenetrating material from the PLA/PLGA family, which is soluble in chloroform, the concentration of interpenetrating material dissolved in the solvent may not be particularly large. It may, for example, be 4%. The concentration may be chosen based upon a combination of molecular weight, the viscosity of the resulting solution, and pore size. In such a case, when the solvent evaporates, only a relatively small volume of interpenetrating material would be left behind, even if the solution were to initially fill all void spaces. In this embodiment, in regions from which solution is drained, deposition of dissolved material will tend to form essentially a coating of the interpenetrating material on the exposed surfaces of the matrix-material network, such as the original surfaces of the particles and the surfaces of the necks which formed joining particles to each other.

When polymer is deposited into void spaces by being dissolved in chloroform, additional substances may be deposited simultaneously deposited. Many Active Pharmaceutical Ingredients are soluble in chloroform or in other solvents that could be used, such as ethanol (which is miscible with chloroform). Thus, when the solvent evaporates, it could leave behind not just polymer but also Active Pharmaceutical Ingredient or other bioactive substance as a co-precipitate.

Another method of placing interpenetrating material is to heat the interpenetrating material to form a melt of sufficiently low viscosity to flow the material into the pores. The material may be allowed to fill the void spaces, or may be drained thereby leaving some empty space. For example, a melt with a viscosity of 20 cP or less may be used. PLGA can melt without decomposing. Other resorbable polymers can also melt without decomposing and could be so infused. Partial drainage can be used as described herein.

Yet another method of placing interpenetrating material so that it partially occupies the interpenetrant network is to infuse the interpenetrant network with a monomer, which is generally of low viscosity, then cause or allow some of the monomer to drain out, optionally cause or allow some liquid to substantially remain in some region of the biostructure, and then polymerize the remaining monomer to form a polymer which is essentially solid. What is referred to as a monomer may be monomer containing also some fraction of polymer of some degree of polymerization or molecular weight. Such a mixture would still have the low viscosity and easy infusing characteristics of pure monomer, while exhibiting less shrinkage upon polymerization than pure monomer would exhibit. Examples are methylmethacrylate (MMA) monomer and polymethylmethacrylate (PMMA) polymer with a suitable initiator such as benzoyl peroxide.

Comb polymers are a specific family of substances which are of interest for use in biomedical articles and which may be used as the interpenetrating material. Comb polymers typically can dissolve in the same solvents or similar solvents as the ordinary polymers to which they are related, and so the comb polymers could be deposited into porous materials by solution deposition as just described. Comb polymers could also be deposited by melt infusion if they have appropriately low melt viscosity and do not decompose.

If a bioactive substance is additionally used, it can be infused into all or some of the third interconnected network after all of the already-described manufacturing steps are essentially complete. Sterilization steps may be performed at appropriate times during or after any of the processes.

Further Discussion

Discussion has named resorbable polymers that are members of the polyester family, such as poly lactic acid (PLA) and poly lactic co-glycolic acid (PLGA). Other members of the polyester family are homopolymers (lactide), copolymers (glycolide), and terpolymers (caprolactone), and L-PLA, poly (D,L-lactide-co-glycolide) (D,L-PLA) and PCL (poly(epsilon-caprolactone)), poly(glycolic acid) (PGA), poly(L-lactic acid) (PLLA) and their copolymer, poly(DL-lactic-co-glycolic acid) (PLGA). The biocompatibility and sterilizability of these polymers have been well documented. In addition, their degradation rates can be tailored to match the rate of new tissue formation. The degradation rate of the amorphous copolymer can be adjusted by altering the ratio of lactide monomer to glycolide monomer in the polymer composition.

It is known that when PLGA and similar substances erode, they erode in a bulk fashion. It is possible for significant quantities of such substances to disappear or collapse around the same time, which is not ideal for bone in-growth. For bone in-growth it is desirable for bone to in-grow at essentially the same rate at which implanted material disappears. Thus, any sudden or rapid disappearance of implanted material is undesirable, and gradual disappearance is preferred. However, polyesters are not the only possible family of materials. There are other known materials that disappear gradually by an erosion diffusion process, which means that the material can only disappear from the outside or surface working its way inward. An example of such a material is polyhydroxyalkanoate (PHA). Polyanhydrides exhibit bulk surface degradation and dissolution.

Comb polymers may be used as the interpenetrating material. Different comb polymers could be deposited in different regions of the biomedical biostructure. In general, different polymers of any type could be deposited in different regions of the biomedical biostructure. They could be deposited in any combination of comb polymers or ordinary polymers and any combination of resorbable or non-resorbable polymers.

If both the matrix material and the interpenetrating material are resorbable, the rates of resorption of the matrix and the interpenetrating material may in general be unequal, and may have any value relative to each other. The rate of resorption of the interpenetrating material may be tailored through adjustment of chemical composition as described elsewhere herein. If comb polymers are used, the attraction or repulsion for certain types of molecules or cells can be adjusted for the biostructure as a whole or can be separately controlled for local regions of the biostructure.

In the present invention, the deposited interpenetrating material mechanically strengthens the biostructure, compared to the biostructure where the only source of mechanical strength is the necks between particles formed by partial sintering. For example, such strengthening could allow the biostructure to better withstand handling by the surgeon while it is being installed in a patient and during the later stages of manufacturing. The tendency of particles at the surface of the biostructure to rub off during handling will be reduced. The remaining void space, especially if it forms an interconnected network, allows access of bodily fluids for resorbing the resorbable material and facilitates cell in-growth. Resorption of the resorbable material thus occurs faster.

The strength of the resulting composite, while less than the strength of a fully infused interpenetrating composite, can still be significantly greater than the strength of totally uninfused material, and is sufficient for some purposes. At the same time, the amount of lactic acid degradation products which must be eliminated by the body is reduced compared to that for a fully infused biostructure, access of bodily fluids for accomplishing resorption is improved, and space is provided in which bioactive materials can be placed and cell in-growth can occur.

In any instance of infusion of liquid into a network, it would be possible to use a jet of gas, gas under pressure, vacuum, etc., to help remove liquid from the network. Removal of liquid can also be aided by touching the infused biostructure to an absorbent material. Retention of liquid, such as to form a skin, can be encouraged by not touching a particular surface of the biostructure to any solid or by touching it only to a surface which is solid and non-absorbent. The methods of manufacture may further include sterilization at appropriate stages of manufacture and may also include the use of supercritical fluids, including supercritical or liquid carbon dioxide, for removal of undesired residual substances.

Possible forms of biostructure of the present invention include replacements for the entirety or portions of essentially any bone in the human body, or augmentations or reconstructions thereof, or bones in animals, including but not limited to craniofacial, alveolar ridge, mandible, parts for spinal fusion, legs, arms, hands, feet, joints, etc. The present invention could also be used in the manufacture of tissue scaffolds or for other purposes.

The invention is further described but is in no way limited by the following Examples.

EXAMPLE 1

Partially Filling Void by Solution-Depositing Resorbable Polymer

Bars of rectangular cross-section were made of hydroxyapatite powder by three-dimensional printing. The nominal dimensions of the bars were 20 mm long by 3 mm high by 4.5 mm wide. The powder was hydroxyapatite powder (CeraMed, Lakewood, Colo.) having a 40-micron particle size and having been pre-sintered to a temperature of 1000 C. The binder liquid comprised an aqueous solution of polyacrylic acid. Following three-dimensional printing, the bars were heated to a temperature of 400-C for a time period of 1 hour to cause decomposition of the polyacrylic acid and then were heated to a temperature of 1350-C for 2 hours to partially sinter the particles together. After sintering, weights of each individual sintered bar were measured utilizing a precision balance (Meftler Toledo, Columbus, Ohio). After that, the bars were infused with a solution of PLGA dissolved in chloroform. The PLGA was a 50:50 mixture of lactide and glycolide monomers with a molecular weight of 50 kDa. It was dissolved in chloroform at a concentration of 4%.

For infiltration of the chloroform/PLGA solution into the bars, approximately 25 ml of the solution was dispensed into a metal container. The bars were placed on end into the solution for one minute. The bars were then fully immersed for 2–5 minutes, and were then removed with forceps. Upon removal, any large droplets of solution were touched off on the edge of the container and the bars were placed onto a smooth flat nonabsorbent surface, i.e., aluminum foil, to air dry in a ventilated hood for at least 48 hours. The position of the bars during the entire drying process was horizontal and static, which is believed to have caused the solution to gravitate downward as evaporation occurred so that the solution preferentially occupied the porous region that was the bottom of the bar in the position in which the bar existed during drying. It is believed that the solution also somewhat occupied the sides of the bar during drying.

The bars appear to contain a deposition of PLGA concentrated on the particular external surface of the rectangular-prismatic bar that was the bottom surface of the bar during evaporation of the solvent, and also there appeared to be some deposition of PLGA on the external surfaces that were the sides of the bar during evaporation of the solvent. It is believed that at the bottom surface the PLGA may have formed essentially a "skin." Internal regions of the bar and the top surface of the bar contained much less of this interpenetrating material.

The bars were processed in two batches, with the first batch containing 8 bars and the second batch containing 7 bars. The first batch was infused first using the chloroform/PLGA solution at the nominal mixed concentration of 4%. Due to gradual evaporation of the chloroform from the solution in the container, by the time the second batch was infused, the solution was more concentrated, with the concentration of PLGA being estimated as 6%. A third group of bars was not infused at all, as a control. Weights of the test bars after infusion and drying were also recorded. The increase in weight of the bars as a result of the infusion, on a percentage basis, was only at most 2% of the original weight of the bars. This indicates that on average there was not a particularly large amount of material deposited in the pores, and, since there was a concentration of deposited material in the "skin," the actual amount deposited in the pores was even less. Nevertheless, there was a significant increase in the mechanical strength of the bars.

Mechanical testing in the form of four point bending tests was performed on all the samples. Orientation of the bars for bending tests was such that the thinnest dimension (3 mm) was the height dimension for the beam in bending. Samples were loaded to their ultimate strength. The fracture mode was brittle fracture. Cross sectional area at the fracture was measured for individual bars and was used to normalize the calculated bending strength. During bending tests the PLGA-concentrated surface was on the extreme fiber of the beam in bending, but the orientation as to whether it was on the tension side or the compression side of the beam was not controlled.

The average strength in bending of the bars that were only sintered and not infused at all was 1.26 MPa. Identically-produced bars which were also infused once with the PLGA at a 4% concentration attained an average bending strength of 3.73 MPa, which is approximately a tripling of the original strength. Bars that were infused once with the PLGA at a concentration of 6% attained an average bending strength of 4.75 MPa, which is approximately a quadrupling of the original strength. The data on strength and weight are given in Table 1.

TABLE 1

Parameters and Strengths of PLGA-Infused Hydroxyapatite Bars

| Type of Processing of Bars | Number of bars in Sample | Concentration of PLGA in infusing Solution | Mass of bar at time of bending test (averaged for all bars in sample) grams | Fraction of PLGA in Bar (averaged for all bars in sample) (normalized by weight of uninfused bar) | Bending Strength (Averaged for all bars in sample) MPa |
|---|---|---|---|---|---|
| No PLGA infused | 13 | Not infused | 0.5274 | 0.00% | 1.26 |
| PLGA Infused (4%) | 8 | 4% | 0.5291 | 1.42% | 3.73 |
| PLGA Infused (6%) | 7 | 6% | 0.5383 | 2.07% | 4.75 |

Figure 18:
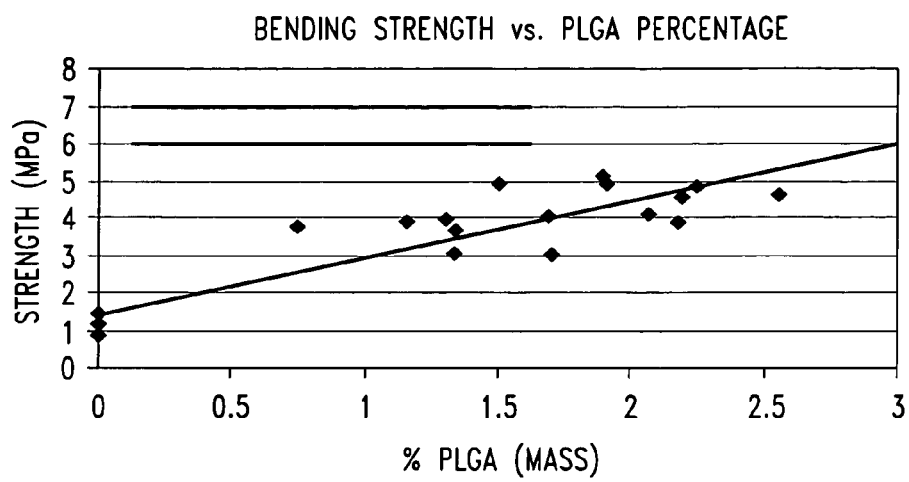
FIG. 18 is a graph of the strength of an engineered regenerative biostructure versus the percentage polymer for a partially infused biostructure in accordance with principles of the present invention.

The strength results reported in Table 1 are values averaged for the indicated number of samples that received identical treatment. To view the data in slightly more detail, the bending strength for each individual bar is plotted in FIG. 18 as a function of the amount of PLGA in each individual sample. The PLGA content is normalized by the original weight of each individual sample. One way of concentrating the solute in the gravitationally lowest region of the biostructure is to place the biostructure on a nonabsorbent or impervious surface as it dries. Another way is to have the gravitationally lowest surface of the biostructure in contact with no solid surface at all as drying takes place. A technique which would not be conducive to formation of the skin or concentrated region is for the bottom surface to be in contact with an absorbent material, because an absorbent contacting material would tend to draw off any excess solution as soon as it accumulated and hence would work against the creation of a "skin" or nonuniform distribution of interpenetrating material. It is also possible to rotate the part while it is being dried.

It is possible also to infuse the biostructure multiple times, with drying in between infusing steps, and the infused region could be different from one infusion to another. Regions that are desired to have a greater content of interpenetrating material could be infused more times.

The presence of a skin may be advantageous. In these experiments, the skin was located at the extreme fiber of the beam, and the extreme fiber of a beam is the place where strengthening of the material especially strengthens the biostructure in bending. Infusion concentrated at an external surface of the biostructure could also provide protection against damage due to handling and other activities during surgery. In both usages, the relatively small deposition of interpenetrating material in the interior of the biostructure means that the patient is not subjected to unnecessary lactic acid decomposition products from interpenetrating material in the interior of the biostructure.

Also, the voids provide possible storage areas for bioactive additives, if they are used. If desired, especially for simple shapes such as bars having a rectangular cross-section, it would be possible to skin-infuse, as has just been described, various external surfaces of the biostructure in succession, thereby coating as many surfaces of the object as desired. For objects which are in a shape which approximates a round cylinder, it would be possible to direct the solution to the overall external surface of the biostructure by rotating the biostructure while it dries, to create centrifugal force directed outward in all directions from the center of the biostructure.

In this example, the interpenetrating material was resorbable and the matrix material was hydroxyapatite, which is generally considered non-resorbable. Of course, it would also have been possible to use tricalcium phosphate or other resorbable calcium-phosphorus compound, instead of hydroxyapatite, in which case the entire biostructure would have been resorbable, including both the matrix material and the interpenetrating material. It would also have been possible to use hydroxyapatite with a soluble polymer that was non-resorbable, in which case both the matrix and the polymer would be non-resorbable. With the use of three-dimensional printing it is possible to manufacture articles in any arbitrary shape, not just bars of rectangular cross-section.

EXAMPLE 2

Achieving a Finer Degree of Variation of Infiltration

In the preceding example, any individual region of the matrix-material network either was infused and drained, leaving a coating of interpenetrating material on the matrix-material network, or else it collected solution which remained liquid until nearly the last of the solvent evaporated, resulting in it being essentially fully filled by interpenetrating material. It would further be possible to perform multiple dippings or infusions. These infusions could be done in an identical manner each time, or they could be done so that in some instances less than the entire biostructure is dipped, followed by subsequent evaporation. In such an event, regions which received dipping or infusion more frequently, followed in each instance by drainage, would have a thicker coating than regions which received only one dipping or infusion. At the same time, there could still be a "skin" or one or more fully-infused regions as a result of the region(s) being kept wet until complete evaporation. The orientation of the biostructure need not be identical for each infusion. If the orientation is changed between infusions, this could provide the ability form a "skin" at various different external surfaces of the biostructure.

EXAMPLE 3

Filling some but not all of the void by melt-depositing polymer

In addition to being soluble in solvents such as chloroform, PLA/PLGA is also capable of being melted without decomposing. Other resorbable polymers are also believed to be meltable. Partial infusion of interpenetrating material into the pores of the three-dimensional printing printed biostructure could be achieved, assuming that the melt has sufficiently low viscosity, by melting the infusing material, infusing the molten material into the pores, causing or allowing some of the melted material to drain, and then causing or allowing the remaining molten material to solidify due to decrease of temperature. Vacuum can be used for degassing and to direct the motion of the liquid. As in the earlier example, the drainage of liquid from the sample can be limited so that at the gravitationally lowest part of the sample there is a concentration of interpenetrating material.

EXAMPLE 4

Filling some but not all of the void by infusing monomer and then polymerizing

Similarly, it is possible that the infusing material can be introduced into the pores as a monomer, which is usually much less viscous than polymer. Monomer can be introduced into the pores so as to wet the surfaces of the pores and can then be caused or allowed to drain out so as to leave just a coating of monomer on internal surfaces of pores. As in the earlier example, the drainage of liquid from the sample can be limited so that at the gravitationally lowest part of the sample there is a concentration of interpenetrating material. Then, the monomer that remains can be cured to form polymer, which is stronger than monomer. Curing can be accomplished by elevated temperature, by initiators such as peroxides, by nuclear radiation, by catalysis, by the passage of time since the mixing of two components, etc. The monomer could also comprise some amount of polymer mixed in with it at the time it is introduced into the empty spaces of the biostructure. In sufficiently small concentrations, polymer content does not appreciably increase the viscosity of the liquid but does reduce the amount of shrinkage that occurs upon polymerization of the monomer. The polymer resulting from the monomer can be either a resorbable substance or a nonresorbable substance such as PMMA. Multiple infusions can be performed.

EXAMPLE 5

Comb Polymer

Comb polymer which is derived from PMMA or from PLLA/PLGA is soluble in chloroform just as PLL/PLGA are. Other comb polymers are soluble in the same solvents or similar solvents as the ordinary polymers to which they are related. These comb polymers can be solution-deposited just as PLLA/PLGA were solution-deposited in Example 1. Comb polymers could also be melt-deposited. They could be deposited so as to partially fill the non-matrix-material network or they could be deposited so as to completely fill that network. It would be possible to create multiple regions of differing properties as far as composition of the interpenetrating material or extent of filling. It would also be possible, as described earlier, that other substances such as Active Pharmaceutical Ingredients or other bioactive substances could be dissolved in the solvent along with the comb polymer, and could be co-precipitated or co-deposited.

Biostructure with a Dissolvable Interpenetrating Phase Composite

It is also possible that portions of the biostructure not occupied by powder particles could be occupied by a water-soluble material, such as to provide a strengthening or handling-protection effect which goes away quickly upon installation of the biostructure in the body and resulting dissolution of the material by bodily fluids. This water-soluble substance may vary in amount of composition from one place to another in the biostructure, and more than one such substance may be used. This water-soluble substance may be used to partially or completely interpenetrate the voids of the biostructure similar to the interpenetrant matrix described above.

The interpenetrating material may be chosen to be soluble in water so that, when implanted in the body, it will be soluble in bodily fluids and thus easily leave the biostructure. A soluble material is capable of dissolving in a solvent without undergoing chemical change. This is in contrast to a resorbable material, which must undergo some chemical change under the action of cells or bodily fluids in order to become soluble.

The term soluble may be considered to mean a saturation concentration or solubility in a specified solvent of at least one part in 10,000 at body temperature. In general, the more soluble in water a material is, the faster it can be expected to disappear from the pores of a biostructure implanted in a patient's body. The interpenetrating material may be solid or at least semi-solid at room temperature. The interpenetrating material may be present in the biomedical biostructure at the time it is implanted into the recipient's body. The interpenetrating material may be capable of existing in a liquid or fluid state so that it can be introduced into pores in desired locations as liquid. This can be accomplished either by melting or by dissolving the interpenetrating material. In regard to melt infusion, in order to be able to be melt-infused, the dissolvable material may have a melting point that is less than its decomposition temperature, so that it may be able to melt without decomposing. As described herein, the water-soluble interpenetrating material may fill up all of the non-matrix-material network in the entire biostructure or it may fill up less than all of the non-matrix-material network.

One family of materials suitable for use as the interpenetrating material is sugar alcohols such as mannitol. Mannitol ($C_6O_6H_{14}$) is a six-carbon sugar alcohol and melts at 165 C without decomposing, which means that it can be infused into a porous structure in the form of a melt. Other possible materials of the same family include sorbitol and xylitol. These compounds are expected to be benign substances in terms of their effect upon the body when the biostructure is implanted in the body of a recipient and the substance dissolves out. These three substances are sometimes included in food products such as sugar-free chewing gum. Mannitol is sometimes administered to patients as part of medical treatment, for its osmotic effect, in the treatment of acute renal failure, acute traumatic brain injury (swelling) and a type of fish poisoning. Mannitol is also known to be non-reactive with various polymers that might be used as a non-soluble interpenetrating material in an interpenetrating composite.

The solubilities of these substances in water at approximately room temperature are as follows. The more soluble such a material is in water, the faster it can be expected to leach out from the biostructure after implantation.

| | | |
|---|---|---|
| Mannitol: | 1 part in 5.5 | at 20 C. |
| Sorbitol: | 1 part in 0.5 | at 25 C. |
| Xylitol: | 1 part in 1.6 | at 20 C. |

(Ref.: Handbook of Pharmaceutical Excipients, Kibbe, 1986, pages 325, 516 and 603 respectively)

Another possible category of materials is sugars. Examples of sugars that could possibly be used include sucrose, fructose, lactose, maltose, and dextrose. If such a material is not melt-infusable, it could at least be solution-infused.

Another family of substances that may be useful as a dissolvable interpenetrating material is water-soluble polymers. In regard to polymers, the length of the polymer chain is a parameter that can be adjusted to tailor physical properties to what is desired in a particular application. Longer chain length and higher molecular weight generally result in a higher melting point. Poly ethylene glycols (PEG) are one suitable family. By adjustment of chain length, PEG polymers can be adjusted to have properties ranging from being liquid at room temperature, to being waxy at room temperature, to being solid at room temperature. It is possible that the substance may be chosen so as to be somewhat solid at room temperature but less than completely solid at body temperature. Or, it may be chosen to be fairly solid at both temperatures.

Poly ethylene oxides and poly propylene oxides are also possible suitable substances. Another example of a family of water-soluble polymeric substances is poly vinyl alcohols (PVA). It is possible that, because of their large molecular weight, water-soluble polymers such as those just described may have less of an osmotic effect on the body than relatively simple, low molecular weight substances such as mannitol. The term polymer, as used here, is intended to also include copolymers, which may contain more than one different kind of constituent monomer.

It is further possible that the water-soluble interpenetrating material may include one or more biologically active or beneficial substances, either in addition to or instead of the substances already described. Examples of such biologically active or beneficial substances are antibiotics, Active Pharmaceutical Ingredients, anesthetics, anti-inflammatory substances, growth promoting substances, hormones, peptides, bone morphogenic proteins, cells or cell fragments, etc. Incorporation of such substances into the biostructure could be performed either with melt-infusion (if the interpenetrating material melts at a melting temperature sufficiently low to avoid damaging the bioactive substances) or with solution-infusion as described subsequently.

It is also possible that the liquid that brings the interpenetrating substance into the non-matrix-material network could contain micelles or suspended particles of these or other substances. For example, some Active Pharmaceutical Ingredients are not very water-soluble but could be brought into the pores of the biostructure in the form of suspended particles or micelles in the liquid that fills the pores so as to later form a solid in the pores.

The biostructure may have more than one distinct region as defined by what interpenetrating material occupies it. It may be desired that only some portions of the biostructure contain water-soluble interpenetrating material. It is possible that other portions of the biostructure may be impregnated with some other interpenetrating material(s). The other interpenetrating material(s) in other portions of the biostructure may be either resorbable or nonresorbable or even may be water-soluble but with different properties. It is possible that a biomedical biostructure may be made so as to have one region that is infused with a substance from one of these categories and another region or regions of the same biostructure may be infused with a different substance which may be from another of these categories, in any combination.

For example, it would be possible for the biostructure as implanted in a patient to be infused with a dissolvable material in one region and a resorbable material in another region, or a dissolvable material in one region and a non-resorbable material in another region. It is also possible that a region may first be melt-infused with a higher-melting-point substance and then another region may be melt-infused with a lower-melting-point substance. It is possible that some space could be filled by an interpenetrating material which is dissolvable (which would be likely to disappear the most quickly), other space could be filled by a resorbable interpenetrating material (which might disappear at a slower rate), and some might be filled by a nonresorbable interpenetrating material (which would essentially never disappear).

Figure 19:
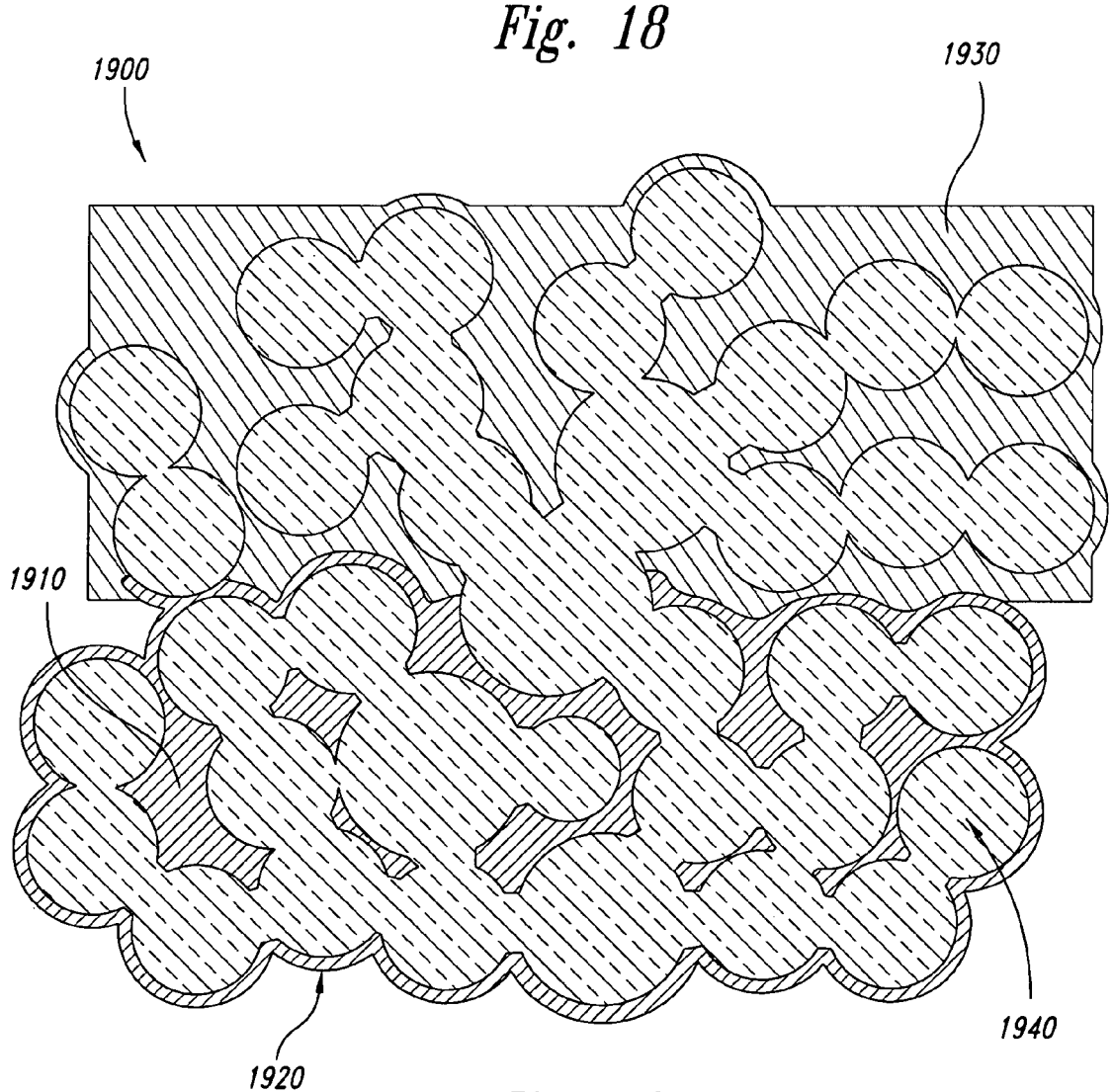
FIG. 19 is a cross sectional view of a fully infused portion of an engineered regenerative biostructure with two different infusion materials in accordance with principles of the present invention.

FIG. 19 is a cross sectional view of a fully infused portion of an engineered regenerative biostructure 1900 with two different infusion materials in accordance with principles of the present invention. In the exemplary embodiment, a first interpenetration material 1910 is a water-soluble interpenetrating material that conforms to the shape of the biostructure along an edge 1920 and fills the pores of the matrix 1940. The surface of the biostructure may itself correspond to a shape of a natural bone already in the patient's body or to some other feature of the patient's body. When the water-soluble interpenetrating material dissolves out of the matrix-material-network near its surface, this will reveal a porous structure that may be intended as an apposition layer for encouraging in-growth of bone or other tissue from neighboring natural bone. The pore size, void fraction and other parameters of the matrix-material network may be appropriately designed to optimally encourage in-growth of bone into this exposed network, as is known in the art. The dissolvable material may leach out at a rate that provides a faster rate of emptying the pores than could be achieved using a resorbable material. A second interpenetrating material 1930 may include a resorbable, a non-resorbable material, or a dissolvable material that dissolves at a rate different from the first interpenetrating material.

Again, the dissolvable material may serve a purpose such as protecting the porous structure from damage due to handling such as during later stages of manufacture and during surgery.

Methods of Manufacture

After the matrix-material network has been created as previously described herein, the interpenetrating material may be introduced into it. The interpenetrating material may be applied to or introduced into the biostructure as a melt and may then solidify due to decrease of temperature. For example, mannitol melts at 165 C without decomposing. The viscosity of melted mannitol is in the tens of centipoises, which is sufficiently low viscosity to allow it to infuse into pores whose size is in the tens of microns or larger. Vacuum degassing may be desirable to remove most air from the infusion process and greatly reduce the likelihood of encountering gas bubbles in the melt. Heat for liquefying the interpenetrating material can be applied locally, or the entire infusing operation may be performed in a sufficiently hot environment. When the biostructure is sufficiently infused it may be returned to ambient temperature.

Melt-infusing is not the only possible way of introducing the dissolvable interpenetrating material. Material could be infused by solution-infusing, that is, being dissolved in a solvent, such as water, and depositing as a solid coming out of solution. Coming out of solution may result from evaporation of solvent, from change of temperature of the solution, etc. In this case, the biostructure might be kept under the liquid level of the solution during the process of coming out of solution, until its pores are substantially filled with solute that is coming out of solution. Solution infusing may be useful in the case of materials that might be adversely affected by elevated temperature if the material to be infused were to be melted for melt-infusion.

If it is desired that the biostructure contains more than one region each with a different interpenetrating material, selective deposition of interpenetrating materials into the biostructure may be achieved by temporarily coating or masking or filling appropriate regions of the biostructure with a removable filler material, or it may be achieved by partly submerging the biostructure in a bath of the infusing liquid, and performing more than one infusing operation in sequence.

If in any part of the biostructure, the pores are not completely filled up with an already-described substance, the incompletely filled pores may be further filled with bioactive substances such as already discussed.

More than one interpenetrating material could be used in a single biostructure. For example, it might be desirable to perform some infusing with a resorbable polymer and other infusing with a dissolvable substance e.g., PLLA/PLGA together with mannitol. The melt may enter some portions of the biostructure and not others. The other portions may be infused with another material. When liquid enters the pores of a biostructure for the purpose of depositing dissolvable material in the pores, that liquid could also be a suspension or emulsion bringing with it suspended particles or emulsified substances.

Advantages of the present embodiment include the ability of the biostructure to tolerate handling during the later stages of manufacturing and during surgery without much risk of breakage. When the interpenetrating substance dissolves and leaves the biostructure, the pores become available to be occupied by in-growing bone or other tissues. The water-soluble interpenetrating material may leach out at a rate that provides a faster rate of emptying the pores than could be achieved using a resorbable material.

Bioactive Substances in Biostructure

It is further possible that in a biostructure that contains powder particles and strengthening substance(s), there still may be room for other substances. Such substances could be bioactive substances, examples of which are given here. A similar infusion process could be performed to deposit one or more bioactive substances in the biostructure. This could be done by solvent deposition or by other methods. Deposition of bioactive substances could be performed either after or instead of deposition of strengthening substances.

Bioactive substances which can be readily combined with the bone particles include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digesters; antitumor agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

Such substances may vary in amount or composition from one place to another in the biostructure, and more than one such substance may be used.

The biostructure could include either internal geometric architecture as already described, or compositional variation, or could include both geometric architecture and compositional within the same biostructure including at the same places within the biostructure.

Further Discussion

The expected mechanical load on the implanted biostructure may influence the design of the biostructure such as the extent of the presence of mesostructures and the use or amount of post-processing such as infusion with a strengthening substance.

The final biostructure could have essentially all of its empty spaces filled with any of the various described substances, or it could still have some empty spaces. The various possible filler materials could be deposited so that the concentration or composition of any of the deposited materials varies from place to place within the biostructure, by infusing substances into pores in such a way that pores in some region(s) of the biostructure are filled to a different extent or with a different substance compared to pores in other region(s) of the biostructure.

The invention is further described but is in no way limited by the following examples. These examples involve experimentally measured in-growth of bone. A general description is provided that contains overall information common to all of the subsequently presented examples.

Description of Experimental and Manufacturing Technique Which is Common to All of the In-vivo Work Reported Herein Experiments were conducted using an animal model that was a rabbit calvarial defect trephine model. This defect model has been shown to be a good delayed-healing model. Male New Zealand White (NZW) rabbits weighing between 3 and 4 kg were used to examine the membranous bone healing response of the implants. Trephine defects were created which were 8 mm in diameter, and the thickness of the skull bone was approximately 3 mm. The overall external shape chosen for the implant was a disk 8 mm in diameter by 3 mm in height. There was a tight fit between the implant and the defect.

The position of the sites of all experimental groups was determined using a randomized block design. After appropriate anesthesia and preparation, a midline incision was made through the skin along the sagittal suture of the skull. Bilateral, 8-mm diameter, circular defects were created in the parietal bone of the skull on either side of the sagittal suture line using an 8-mm outer diameter trephine. Care was taken not to violate the sagittal suture or to interrupt the dura. Defects were filled with one of the various implant groups. If the implant had macrostructures, it was placed with the axial channels facing the dura so that the solid "top" of the implant would inhibit in-growth of connective tissue. All other implants had a rougher surface and a smoother surface and were placed with the rougher surface facing the dura.

As a positive control, some defects were filled with morselized autograft from bone harvested from the skull during the creation of the defect. As a negative control, some defects were left unfilled. The wounds were closed in two layers and, after recovery, the animals were housed in an AAALAC accredited animal facility.

At 4, 8, or 16 weeks post-surgery, the animals were sacrificed and the samples were explanted together with 3 to 5 mm of marginal skull bone and were grossly examined. The samples were fixed in 10% Neutral Buffered Formalin, placed in increasing concentrations of ethanol from 40% to 100%, infiltrated with Citri-Solv, then embedded with increasing grades of polymethylmethacrylate (PMMA) until a hard block was formed. The blocks were then cut with a low-speed diamond wafering blade saw in two planes: the coronal plane going vertically through the diameter of the implant, and a horizontal plane. In coronal sections, the section to be used for analysis was the first slice in the coronal plane, thus providing a section through the center of the implant along the actual diameter.

Samples in the horizontal plane were cut in the horizontal plane going through the thickness of the implant. Some coronal slides were left unstained to measure the mineral apposition rate (MAR) for each implant via fluorescence microscopy. All other slides were stained with Stevenel's Blue, then counterstained with van Gieson's Picro Fuschin (SVG stain). With this combination of stains, soft tissue appears green-blue, muscle appears blue-green, cartilage appears violet blue, and mineralized tissue appears red to orange. Hydroxyapatite particles appear light brown in color.

All experimental groups were analyzed for Mineral Apposition Rate (MAR), linear in-growth percentage, and new bone area percentage. Coronal sections were used to calculate MAR, linear in-growth percentage, and new bone area percentage, while both coronal and horizontal sections were used for qualitative histology. The unstained coronal slides were viewed under ultraviolet (UV) light using a calibrated micrometer eyepiece at 200× power to calculate MAR, which measures new bone apposition and growth based on materials and architectures.

In order to measure bone formation at multiple time periods, each animal was injected intravenously with oxytetracycline at certain time points and with 2-4-bis-[N,N'-Di-(Carboxymethyl)-Aminomethyl] Fluorescein (DCAF) two weeks later. Each substance provides a label or marker in the bone growth at that particular time. Under UV light, the oxytetracycline label appears yellow and the DCAF label appears green. This distinction in color allowed for easy measurement of the interlabel distance, which was measured at five locations around and within the defects.

Under UV light both the oxytetracycline and the DCAF labels were visible to allow for a linear measurement between labels. Several measurements were made at varying regions in and around the defect. The edges of the fluorescent labels were usually quite evident and easily measured using the fluorescent light microscope. The average interlabel distance was divided by the time between injections of labeling substances to obtain a measurement in microns/day.

Additional morphometric data was obtained by using a computer based image analysis system consisting of a CCD camera on the microscope, video pre-processor, video frame grabber, and image analysis program. This system allowed direct area measurement of the total defect area, new bone area, or synthetic graft/particulate area in coronal sections. Areas of scaffold material or new bone were normalized by dividing by the total defect area, thus obtaining the percent of the total defect area filled with new bone or synthetic material. Finally, specimens stained with Van Gieson picrofuchsin were examined microscopically and photographed at various magnifications.

The stained coronal slides were measured for linear in-growth percentage with a calibrated micrometer eyepiece at 20× power. New bone within the implant originating from the left and right margins, as well as any isolated bone spicules along the central axis, were measured and added together. This total linear in-growth distance was normalized by dividing by the width of the defect to give a linear in-growth percentage.

The stained coronal slides were measured for new bone area percentage using an image analysis system calibrated at 10× power. A digital image of the slide was captured and saved for image analysis. Within the defect site, any new bone stained red and any soft tissue stained blue were selected separately and the total area of each was calculated. The image could be enlarged for a more specific determination of new bone and soft tissue within the defect sites.

The new bone area and soft tissue area were subtracted from the total defect area to obtain a measurement of the area of any ceramic material left within the defect. This area was confirmed by manual calculation of the ceramic material area. At each time point, it was evident at low and high magnification that all pores were filled with either new bone or soft tissue. Since the ceramic particles left within the defect were not filled with new tissue, it decreased the available area for tissue to grow into and was not included within the calculation of available area. Consequently, the new bone area and soft tissue area was considered to be the available area. A ratio of new bone area to new bone and soft tissue area gave a percentage of the new bone area normalized to the available area.

For autograft-filled defects, however, the percentage of total bone area included new bone as well as autograft bone, since it was difficult to distinguish between new bone and autograft with the SVG stain. It is important to note that the bone area measurements in these samples included both new bone and autograft particles. If the autograft particles were removed from the final measurement of bone area, we estimate that the bone area percentage might drop approximately 35% of total bone area percentage. This is a significant amount when comparing the performance of the autograft implant with the ERBs of the present invention.

According to the following study: *Healing response to various forms of demineralized bone matrix in athymic rat cranial defects.*, by Chesmel K. D., Branger J, Wertheim H, Scarborough, N; *J Oral Maxillofac Surg* 56:857–863, 1998, while 46% of an autograft-filled defect site was made up of bone, only about 30% of that was newly formed bone.

The conclusion from this reference estimated that while 46% of an autograft-filled defect site was made up of bone, only about 30% of that was newly formed bone. The defect site in this reference was 8 mm in diameter and performed in athymic rats. Therefore, 16% of the total defect area was old, autograft bone and 30% was newly formed bone. According to these results, it was estimated that approximately 65% (that is, (30%/46%)*100) of the total bone area was newly formed bone.

With respect to the results of the Experiments reported herein, the average value of total bone area percentage in the autograft-filled sites was 50.20%. If the estimate above is used to determine the approximate amount of newly formed bone within total bone, the following equation would be used:

$$0.65 \times 50.20\% = 32.63\% \text{ newly formed bone}$$

This estimated number reflects the percent of newly formed bone within the total defect area and would serve as a better comparison to the values of newly formed bone within the synthetic graft sites.

A one-way analysis of variance (ANOVA) was conducted to determine overall statistical significance among all experimental groups for 1) MAR, 2) linear in-growth percentage, and 3) new bone area percentage. Fisher's PLSD post-hoc tests were also conducted to determine statistical significance between all experimental groups. Statistical significance was assumed when $p<0.05$, which means that there is a 95% confidence level that the same conclusion would be reached with an infinitely large sample.

Manufacturing processes common to all reported in-vivo experimental data are also described here. Implant articles were made by three-dimensional printing as described herein. The powder was hydroxyapatite powder, prepared by plasma feed, having an average particle diameter of approximately 40 microns with no particles being larger than 100 microns. A typical packing fraction in the manufactured parts was 50% on a volume basis. (obtained from CeraMed, Lakewood Colo.) The binder liquid dispensed onto the powder was an aqueous solution of polyacrylic acid. The polyacrylic acid binder consisted of 25 vol % Acumer 1510 (Rohm & Haas), 0.5 vol % Glycerin (EM Science), and 74.5 vol % purified water. The binder liquid was dispensed by miniature solenoid-operated valves (microvalves) obtained from The Lee Company, Essex, Conn., part number INKX0505250A.

After completion of the three-dimensional printing process, all parts were subjected to binder burnout and sintering schedules to remove the polyacrylic acid binder and to partially fuse the particles to each other. Binder burnout was performed in a Vulcan 350 furnace. The furnace was ramped at 10° C./min to 400° C. where it was held for 4 hours before cooling to room temperature. In some cases for which the sintering temperature was 1400 C, sintering was performed in a Thermolyne high temperature tube furnace which ramped at 10° C./min to 1400° C. where it was held for 2 hours before cooling to room temperature.

At various steps during the manufacturing process, the samples were characterized by measuring mass and dimensions of the parts. Following manufacture, some samples were tested by various methods, either destructive or non-destructive.

Samples were examined by mercury porosimetry using a porosimeter made by Micromeritics (Norcross, Ga.). Both low-pressure and high-pressure porosimetry runs were performed covering a pressure range from 0.5 psi to 50000 psi. This was suitable for measuring pore sizes in the range of 0.004 microns to 350 microns. Porosimetry results for individual cases are given in the individual Examples.

Some of the samples were also examined by X-Ray Diffraction (XRD) to test for the possible presence of any substance other than hydroxyapatite. The samples for XRD were run on a Siemens D5000 $\Theta/\Theta$ diffractometer using Cu radiation at 40 kV and 30 mA at a step size of 0.02°. The XRD analysis indicated that the samples were 100% hydroxyapatite with no amorphous content or other impurity. No decomposition of the hydroxyapatite was detected. The implants containing macrostructures were found to have a moderate <112> texture (peak at 32.3°). For the solid implants containing no channels of any kind, this diffraction line was closer to the expected value.

While the quantitative results were sometimes not statistically significant because of small sample sizes, there were significant observations regarding trends of patterns and locations of bone formation. The results suggest that control of micro- and mesostructures can be superimposed on biomaterial composition to significantly enhance the performance of ERBs. The results also suggest that combinations of microporosity, to enhance or deter tissue adhesion, and directions meso- and macrostructure, to direct bulk tissue in-growth, can be used in tandem to control tissue in-growth and formation.

All implants were sterilized by gamma irradiation before implantation.

FIGS. 23A–23E are discussed further below and are sectional histology color photographs that illustrate the histological progression at 8 weeks for the various experimental biostructures. In these FIGS, the left photograph is low magnification (5×) and the right photograph is higher magnification (100–200×). The photographs in FIGS. 23A–23E are arranged in a progression from the least bone in-growth to the most bone in-growth measured as a percent of new bone area.

Experimental Details and Results for Specific Cases

Examples are presented in the following progression: These are in a progression of increasing size and complexity of structure.

Example 1 contains small pore size. It is designated as Staggered.

Example 12 contains small pore size and also a feature which produces additional slightly larger voids which are somewhat scattered rather than being ordered or connected to form a long-range structure, but no other feature. It is designated: as Pressed.

Example 3 contains the small pore size and also mesostructures. It is designated as: HA-No, and another nominally identical set is designated as 1400 Stacked.

Example 4 contains the small pore size, and mesostructures, and also macrostructures. It is designated: as HA-Ch Example 5: autograft control.

EXAMPLE 1

Staggered Configuration (1400 Staggered)

Figure 23A:
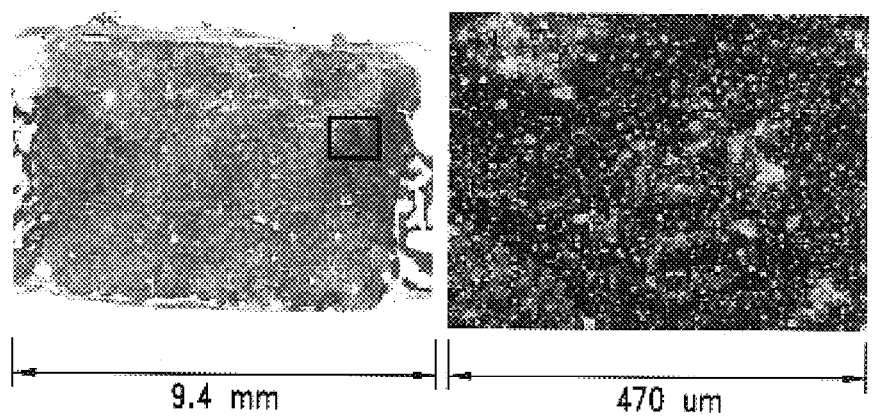
FIGS. 23A–E are histological photographs from differing biostructure configurations to illustrate differing natural bone in-growth rate in accordance with principles of the present invention.

This example has essentially only microporosity. FIG. 23A shows a histological progression of the 1400 Staggered implants at 8 weeks. At all time points, new bone and osteoid was identified, both originating from the margins and as unconnected islands. New bone and marrow cavities were identified at 8 weeks.

Fibrous tissue stained lightly at 4 weeks, with darker staining at 8 and 16 weeks. Vasculature was also apparent at all time points, with progression of blood vessels with thin walls at 4 weeks, thicker walls at 8 weeks, and red blood cell circulation at 16 weeks. At 4 weeks, only one of the implants integrated with the bone from the margins, while the other implant did not integrate at all and was separated by fibrous tissue from the margins. At all time points, as with the 1400 Stacked implants, the rougher bottom surface with "channels" facing the dura contained new bone, with unconnected islands integrating into the implants. Some particulate loosening also occurred at all time points, but it was not severe.

Histological progression of 1400 Staggered implants. FIG. 23A on the left shows Coronal section at 8 weeks (10×), and on the right shows new bone and osteoid within implant at 8 weeks (100×).

EXAMPLE 2

Figure 25B:
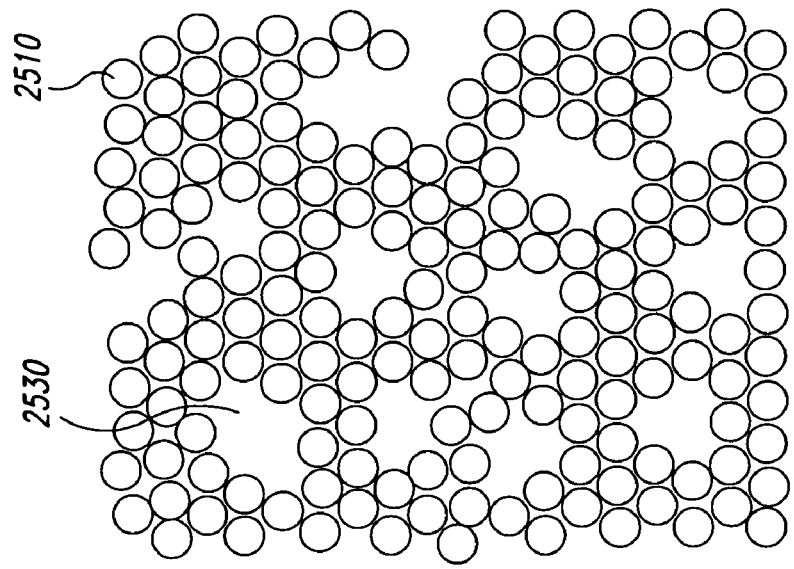
FIGS. 25A and 25B are schematic views of an alternative embodiment for process steps for designing porosity into the biostructure in accordance with principles of the present invention.
Figure 25A:
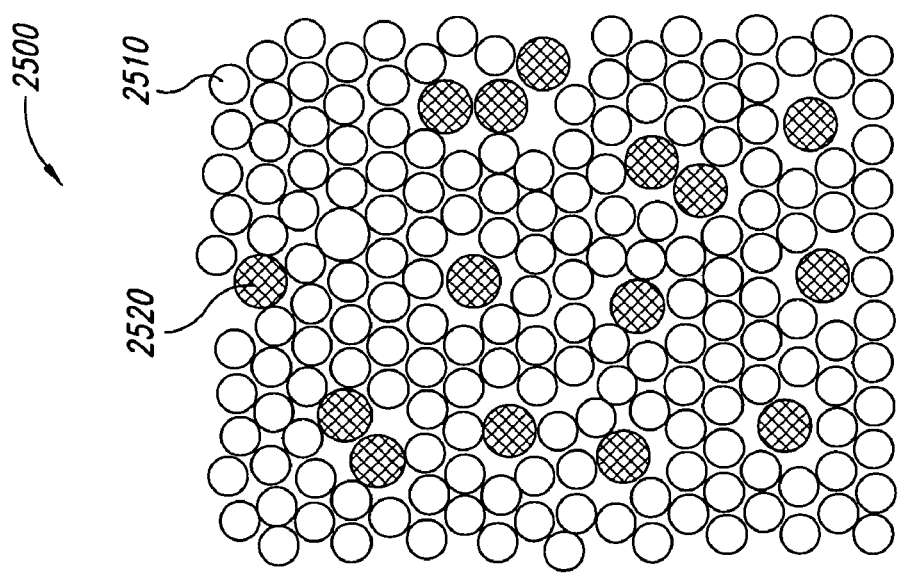

Solid porous biostructure with small pore size and also slightly larger pore structure, but without any macrostructures or organized mesostructures The biostructure of this example contains microporosity as is always present and also adds a slightly larger porosity in a way which does not create any long-range ordered structures. These are referred to as the 1400 Pressed implants. FIGS. 25A and 25B are schematic views of an alternative embodiment for process steps for designing porosity into the biostructure. FIG. 25A illustrates a layer of mixed powder 2500 of powder particles 2510, 2520 of varying sizes. Particles 2510 are made of a sinterable ceramic material. Particles 2520 are place-holders and may be made of a material such as poly ethylene glycol which can decompose into gaseous decomposition products at a temperature lower than the sintering temperature. The particles 2520 may have a slightly larger average particle size than the particles 2510, although this is a function of exactly what final structure is desired. The percentage of particles 2520, on a volume basis, may be in the range of 10% to 15%, although again this is a function of the desired final structure. After completion of three dimensional printing, the biostructure may be press formed and then partially sintered. The sintering burns out selected particles 2520 to form a porous 2530 implantable biostructure. It is also possible that the place-holder particles 2520 could be soluble (such as sugar or salt) and could be dissolved out at the appropriate time.

FIG. 8 shows a histological progression of the 1400 Pressed implants at 4weeks, 8 weeks, and 16 weeks. These implants illustrate an alternative method of manufacturing the designed porosity. At all time points, mostly linear in-growth of new bone and osteoid occurred within these implants; lower amounts of new bone were found as unconnected islands, compared to Examples 2–4. Fibrous tissue stained lightly at 4 weeks, and stained darker at 8 and 16 weeks. Blood vessels with thin walls were found at 4 weeks, with thicker walls at 8 weeks, and circulating red blood cells at 16 weeks. Also, no particulate loosening was apparent. There was no particulate loosening at 4 weeks, with some occurring at 8 and 16 weeks. There was also some dural bone growth, even though there were no "channels."

Figure 23B:
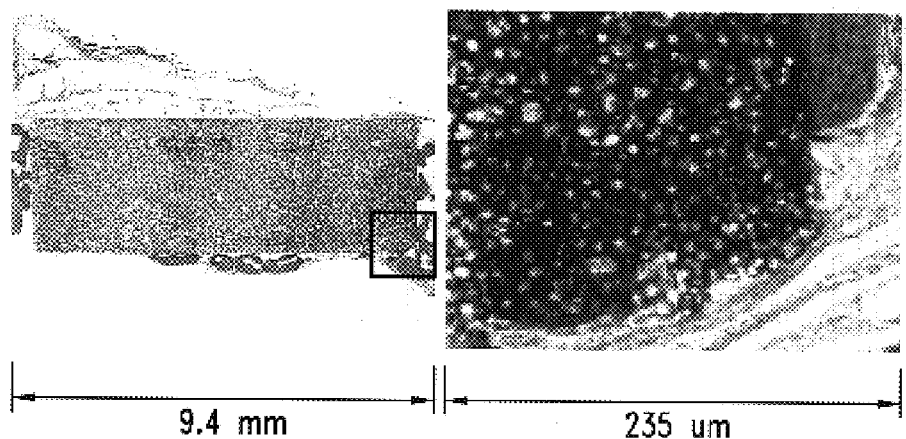
Figure 23C:
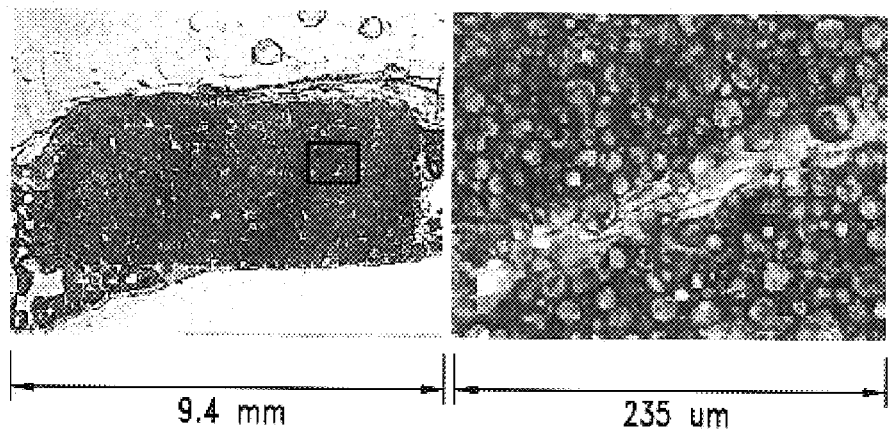

FIG. 23B illustrates the histological progression of 1400 Pressed implants. Left—Coronal section at 8 weeks (10×). Right—Bone/implant interface within implant at 8 weeks (200×).

In this Example, all printing was done with voxel dimensions 400 microns by 400 microns by 200 microns layer thickness. This gives a saturation parameter that is considerably higher than for mesostructure-containing Examples.

EXAMPLE 3

Mesostructures (along with small pore size) HA-No

This example, while continuing to use the small particle and pore size as in the previous example, also has the presence of mesostructures. Mesostructures were achieved by virtue of the relatively small saturation parameter as describe herein. This Examples contains samples with two different designations, both manufactured nominally identically. One designation is HA-no, and the other designation is 1400 Stacked. The printing parameters for this case were a flowrate of 1.4 g/min, drop-to-drop spacing of 450 microns, line-to-line spacing of 450 microns, and layer thickness of 450 microns. The articles were printed in the form of cylinders having a diameter of 8 mm and an axial dimension of 3 mm. The lines of binder were deposited in a stacked configuration with each line directly above the line from the layer below. The orientation of the fast axis motion and hence the mesostructures was horizontal. A typical packing fraction in the manufactured parts was 44% HA (i.e., 56% void).

A. HA-No (100% HA without channels, n=6)

Most of the new bone in the HA-No implants (just as in the HA-Ch implants) appeared to be lamellar in nature, with marrow cavities encapsulated within the new bone. The HA-No implants contained copious amounts of new bone and fibrous tissue in apposition to the new bone within the pores of the implant. A large amount of vasculature was also identified within the HA-No implants (as was also the case with the HA-Ch implants).

Figure 20:
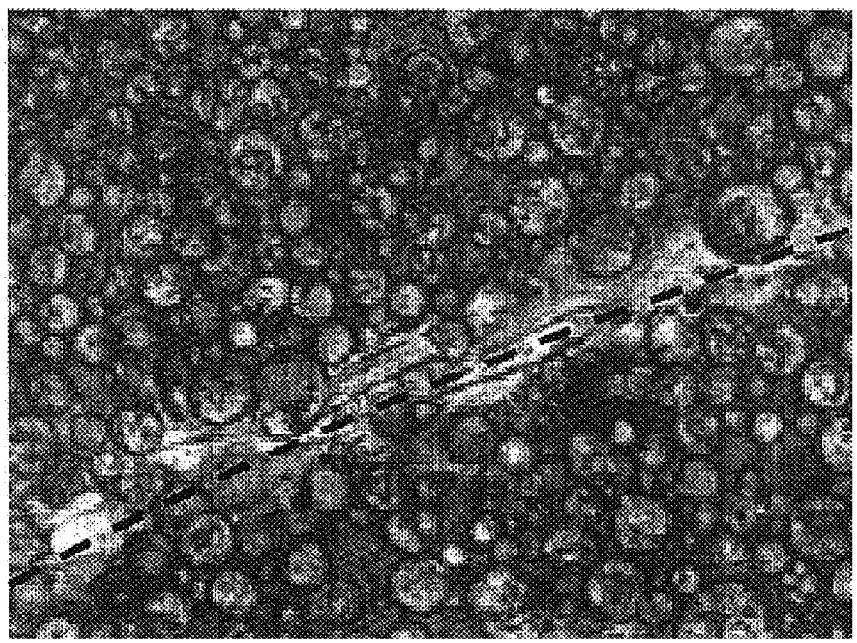
FIG. 20 is a histology photograph of a blood vessel in an implanted engineered regenerative biostructure in accordance with principles of the present invention.

Hydroxyapatite solid disks show in-growth of bone 2–3 mm from margins of defect. Bone has grown into the microporosity and mesoporosity of the scaffold. In FIG. 20 (also FIG. 23C), note blood vessel 2010 growing through scaffold in mesostructure region.

Osteoid staining and darkly-stained fibrous tissue in apposition to new bone could be identified within almost all implants at all time points, indicating that new bone growth was occurring at the time of sacrifice.

B. 1400 Stacked: Histological progressions of the 1400 Stacked implants were measured at 4 weeks, 8 weeks, and 16 weeks. At all time points, new bone was found within the pores, both as linear pieces originating from the margins and as unconnected islands. It was apparent that at each time point, more new bone grew into the implants. At each time point, conversion from woven bone to lamellar bone with marrow cavities also occurred. Some implants were trending towards linear growth at 16 weeks. Also, at 16 weeks, some of the implants had new bone filling in and taking the shape of the larger pores within the implants. Plasma feed powder was used and was sintered at 1400° C., stacked configuration (1400 Stacked, manufacturing steps identical to the manufacturing steps for HA-No).

Osteoid staining and darkly-stained fibrous tissue in apposition to new bone could be identified within almost all implants at all time points, indicating that new bone growth was occurring at the time of sacrifice. Growth was slightly faster than for the 1400 Staggered implants. New bone and marrow cavities were identified at 4 weeks, in comparison to the 1400 Staggered implants, which contained new bone with marrow at 8 weeks.

Vasculature was also evident at all time points. Blood vessels with thin walls were seen beginning to form without circulating red blood cells at 4weeks. At 8 weeks, more blood vessels with thicker walls were apparent. At 16weeks, mature blood vessels with red blood cells were evident, but the red blood cells did not stain too darkly. There was some particulate loosening at all time points, but it was not severe at any time point. At all time points, the rougher bottom surface with "channels" facing the dura contained new bone, with unconnected islands integrating into the implants.

Figure 23D:
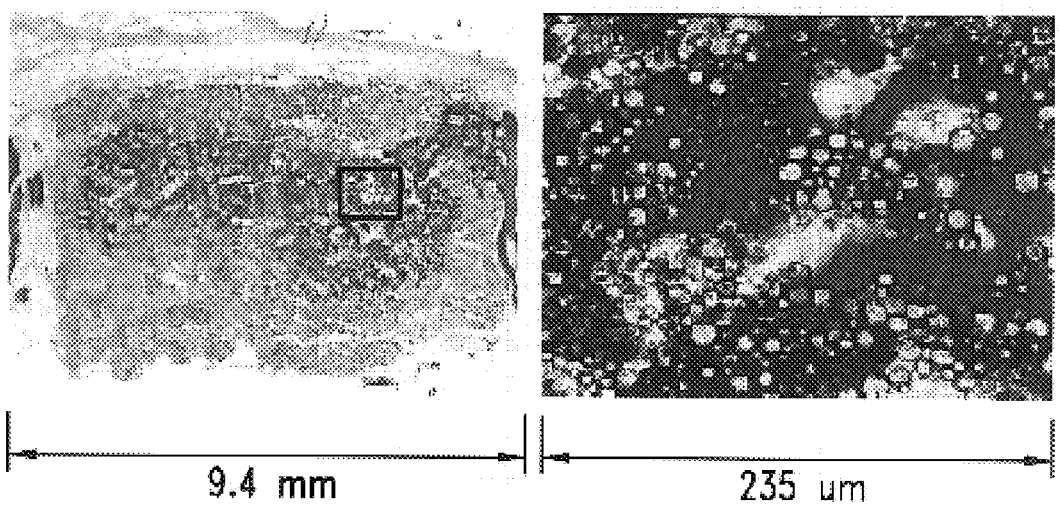
Figure 23E:
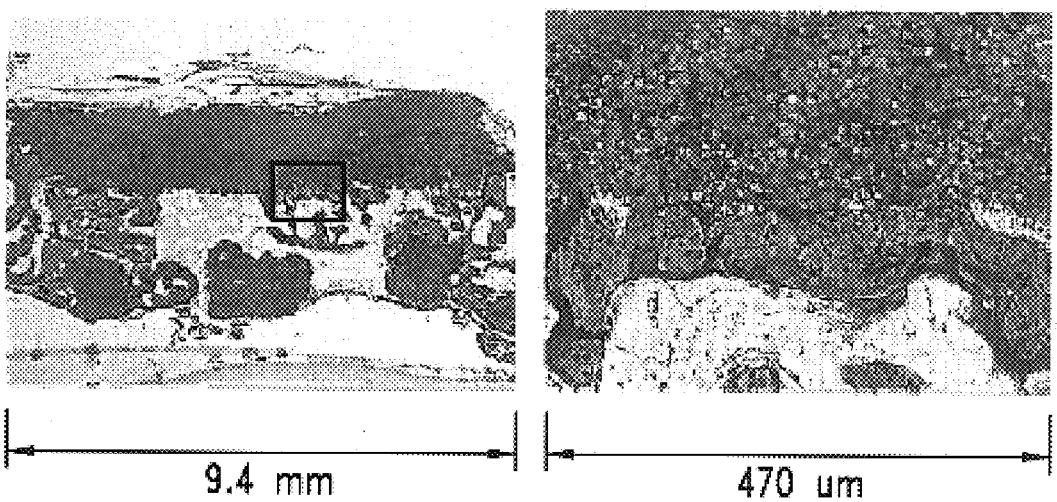

FIG. 23D—illustrates a histological progression of 1400 Stacked implants. Left—Coronal section at 8 weeks (10×). Right—New bone with more osteoblasts lining surface, formation of marrow cavities, and osteoid at 8 weeks (towards middle of picture in green, 200×).

EXAMPLE 4

A case having small pore size along with mesostructures and also macrostructures HA-Ch.

The printing parameters were a flowrate of 1.4 to 1.5 g/minute at a drop production rate of 800 Hz, drop-to-drop spacing of 450 microns, line-to-line spacing of 450 microns, and layer thickness of 450 microns. The articles were printed in the form of cylinders having a diameter of 8 mm and an axial dimension of 3 mm.

This design incorporated a set of four macrostructures (1.6 mm×1mm) in the horizontal (circular) plane of the implant, with two macrostructures being parallel to each other in one direction in the horizontal plane, and the other two macrostructures oriented perpendicular to the first two macrostructures intersecting them. Another set of macrostructures (1.6 mm×1.6 mm) was oriented in the vertical direction and intersected the horizontal macrostructures at their intersection point and exited the implant on one surface (which may be referred to as the bottom surface) but not the other surface. The other surface (which may be referred to as its top surface) was solid except for its inherent porosity. This implant also contained mesostructures, and the mesostructures' long direction was parallel to one set of the horizontal macrostructures.

HA-Ch (100% HA with Radial & Axial Channels, n=6)

Most of the new bone in the HA-Ch implants (as in the HA-no implants) appeared to be lamellar in nature, with marrow cavities encapsulated within the new bone.

The HA-Ch implants contained new bone within the pores (FIG. 1). New bone was also identified within the radial channels originating from the defect margins, while unconnected islands of new bone were identified within the axial channels. A large amount of vasculature was also identified within the HA-Ch implants (as was also the case with the HA-no implants).

Figure 21A:
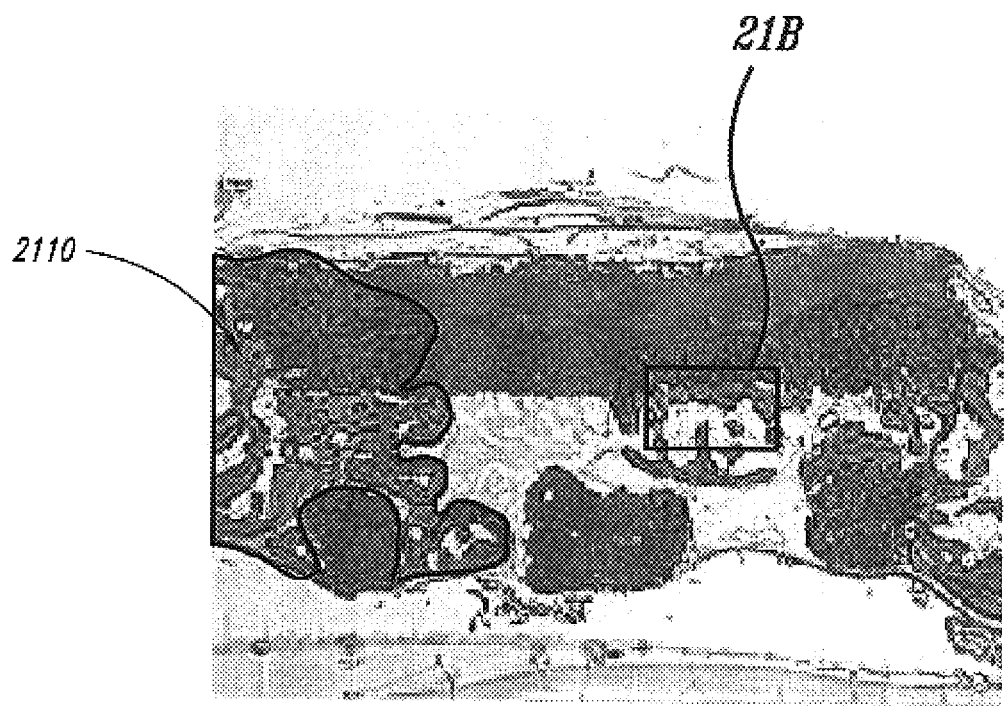
FIGS. 21A and 21B are histology photographs illustrating bone ingrowth into an engineered regenerative biostructure with macrochannels in accordance with principles of the present invention.
Figure 21B:
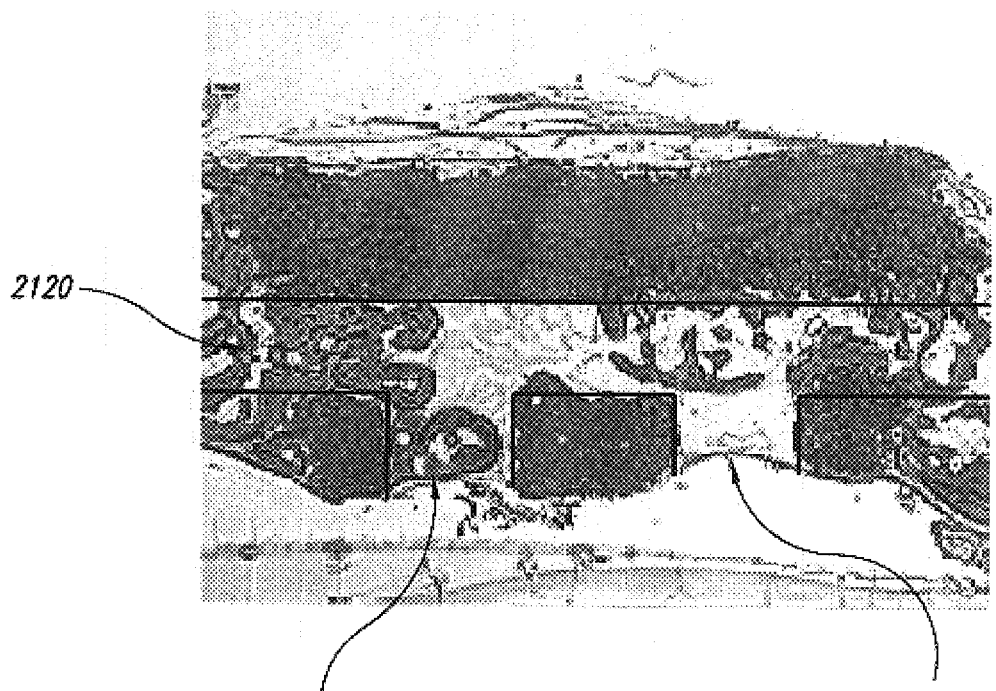

FIGS. 21A and 21B are sectional color histology photographs illustrating bone in growth into the biostructure with macrochannels. These figures are repeated at FIG. 23E to show the progression of best performing biostructure as measured by bone in growth. In FIG. 21A, an irregular pinkish area that corresponds to new bone in growth. FIG. 21B is a magnification of a portion of the sectional photograph in FIG. 21A. The macrochannels 2120, 2130 are outlined in FIG. 21B and illustrate the new bone and fibrous tissue in growth into the macrostructure.

FIG. 21A—Coronal section of HA-Ch implant (10×). FIG. 21B—High magnification view of HA-Ch showing integration of new bone and fibrous tissue from channel to pores (50×).

EXAMPLE 5

Control Cases

A. Unfilled.

At 8 weeks, the unfilled defects were populated with minimal amounts of triangular-shaped bone originating from the defect margins, as well as many isolated bone spicules and fibrous tissue in the center oriented towards the dural side. The bone spicules gave the appearance of complete bridging and healing of the defect, even though no continuous bone apposition was observed. In some samples, the fibrous tissue within the defect sites in most of the samples was concavely shaped. The 8 mm diameter defect is not critical size, meaning that the defect is capable of bridging and healing on its own without any exogenous factors. This is why these defects gave the appearance of complete bridging and complete healing. These results were consistent with previous studies.

B. Autograft.

These defects had the most complete in-growth out of all groups at 8weeks. Although SVG stain does not distinguish new bone from autograft, it is possible to qualitatively distinguish between the two types. Dark-colored resorption lines indicated osteoclastic activity within the autograft particles, while osteoblasts were laying down new bone directly above these resorption lines. Thin curving lines of new bone were seen growing off the edges of the autograft particles as well. Some soft tissue and marrow were found within almost all of the defect sites. Since the autograft particles were not completely resorbed, they served as a template for new bone growth. The histological results were consistent with previous studies.

In previous experiments, histology was performed after certain time periods to assess the degree of bone formation in synthetic graft sites and to compare that to autograft. The histologic stain utilized to detect differences between mineralized and soft tissue made it difficult to distinguish between autograft (bone replaced at the time of surgery) and newly formed bone. Therefore, total bone (autograft plus new bone) was measured in the defects filled with autograft as a positive control. One study cited herein estimated that while 46% of an autograft-filled defect site was made up of bone, only about 30% of that was newly formed bone. Therefore, 16% of the total defect area was old, autograft bone and 30% was newly formed bone. According to these results, it is estimated that approximately 65% ((30%/46%)*100) of the total bone area is newly formed bone.

The average value of total bone area percentage in the autograft-filled sites in our study was 50.20% (see Table 2 below). If the estimate above is used to determine the approximate amount of newly formed bone within total bone, the following equation would be used:

$$0.65 \times 50.20\% = 32.6\% \text{ newly formed bone}$$

This number reflects the percent of newly formed bone within the total defect area and would serve as a better comparison to the values of newly formed bone within the synthetic graft sites.

TABLE 2

Mineral apposition rate (MAR), linear in-growth percentage, and new bone area percentage of implants at 8 weeks.

| | HA-Ch (n = 6) | HA-No (n = 6) | Unfilled Defects (n = 6) | Autograft-Filled Defects (n = 6) |
|---|---|---|---|---|
| MAR (um/day) | 3.43 ± .57 | 2.93 ± .38 | 3.75 ± .73 | 2.96 ± .47 |
| Linear In-growth (%) | 76.55 ± 13.35 | 78.91 ± 20.92 | 66.94 ± 23.08 | 88.18 ± 8.30 |
| New Bone Area / Available Area (%) | 50.51 ± 16.04 | 26.81 ± 10.13 | 18.79 ± 9.71 | 50.20 ± 23.25 32.6 (estimated) |
| TOTAL BONE | | | | 50.20 ± 23.25 |

\*\*It must be noted that the bone area measurements in these samples included both new bone and autograft particles. If the autograph particles could be removed from the final measurement of the bone area, the bone area percentage of the autograft-filled defects would drop to the indicated value, which would place them in the same range as many of the ERBs.

Mineral Apposition Rate (MAR)

The values for all MARs can be found in five Tables 2, 3, 4 and 5. The MARs of all implant types were all statistically similar to each other. Statistical significance was found between unfilled and autograft-filled defects (p<0.03) and unfilled and HA-No (p<0.02). Even though the HA-No MAR was smaller in value than that of autograft-filled defects (2.93±0.38 um/day vs. 2.96±0.47 um/day, respectively), they were statistically similar to each other (p>0.9). This indicated that the implants did not retard new bone formation rates and were within the range of normal new bone growth, between those for unfilled and filled defects (3.75±0.73 um/day and 2.96±0.47 um/day, respectively).

At 4 weeks, no differences in MAR were found amongst the implants types compared (p>0.14). At 8 weeks, there was a trend towards statistical significance between the MAR for the 1400 Stacked and the 1400 Staggered implants (2.305±0.513 um/day and 2.829±0.338 um/day, respectively, p=0.0566with a power of 0.359), while the other comparisons did not reach statistical significance. At 16 weeks, there is a significant difference in MAR between the 1400 Pressed and 1400 Staggered implants (1.730±0.455 um/day and 2.447±0.592 um/day, respectively, p=0.0293). There was no significant differences between the other groups. When looking temporally at the change in MAR within each implant type, there are significant differences within all groups. Similarity was found in the 1400 Stacked implants between 8 weeks and 16 weeks, with a power of 0.124. Similar trends were found for the 1400 Staggered implants. For the 1400Pressed implants, statistical significance was found between 8 weeks and 16 weeks (p=0.0404). If the results at 4 weeks are included for each implant type, statistical significance is found for all implant types between 4 weeks and 8 weeks, as well as 4 weeks and 16 weeks, with a power of at least 81.5%. However, since an n value of 2 is insufficient for proper statistical analysis, they should not be used. If a more accurate analysis were desired, the n value at 4 weeks would need to be increased.

Linear In-growth Percentage

The values for all linear in-growth percentages can be found in five Tables 2, 3, 4 and 5. The HA-No and HA-Ch implants had high amounts of linear bridging, as did the unfilled and autograft-filled defects (all at least 66%). The linear in-growth percentages for these groups were statistically similar to each other. Statistical significance was found between unfilled and autograft4illed defects (p<0.05).

At 4 weeks, statistical significance was not found for linear in-growth amongst the 1400 Stacked, 1400 Staggered, and 1400 Pressed implant types (p>0.2324). Similar results were found at 8 and 16 weeks. Temporally, no statistically significant differences were found between 8 weeks and 16 weeks for all implant types. When the results at 4 weeks are included, statistical significance is found only between 4 weeks and 16 weeks for the 1400 Staggered implants (p=0.0379).

New Bone Area Percentage

The values for all new bone area percentages can be found in five Tables 2, 3, 4 and 5. There is a significant difference in new bone area percentage between HA-Ch and HA-No (p<0.003) and HA-Ch and unfilled defects (p<0.003), with similarity between HA-Ch and autograft-filled defects (p>0.9). When the "p" or significance is equal to 1, then the samples are identical. The further from 1, the less the significance. Therefore, the HA-Ch and the autograft-filled defects are very similar. Also, as mentioned above, new bone and autograft were included in the final measurement of total bone area percentage for autograft-filled defects. If autograft bone was excluded from the total bone area percentages, the new bone area percentages would decrease to 20–30% (from information based on other size defects at a similar time point).

Figure 24A:
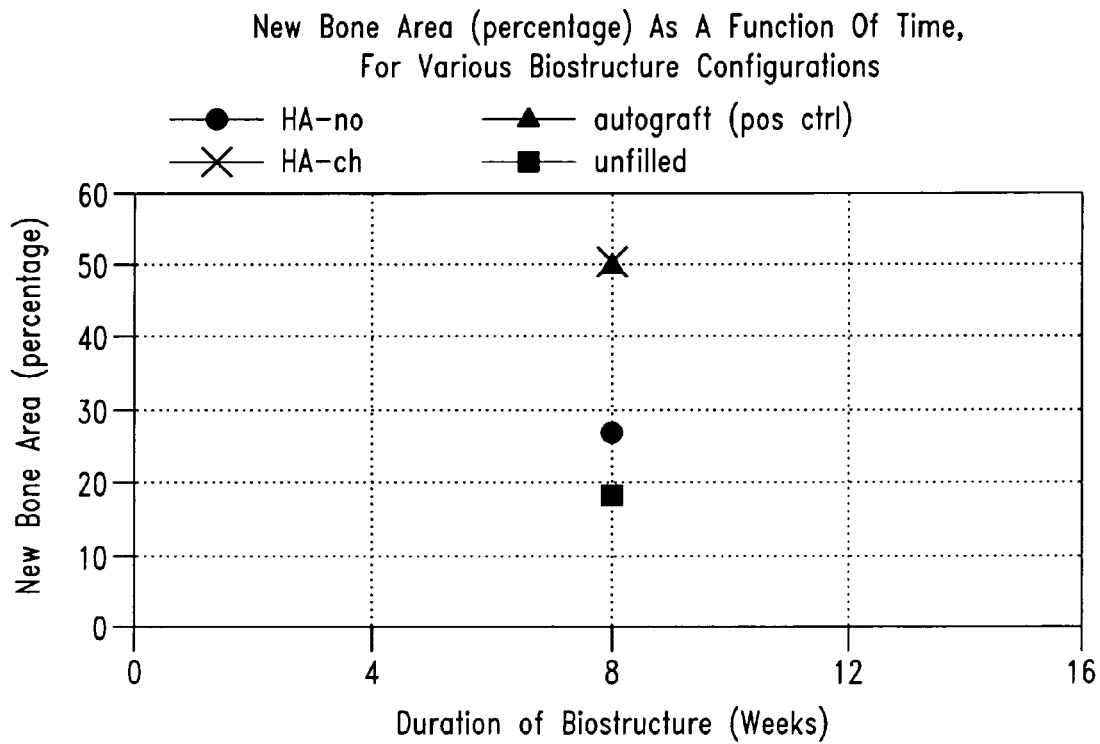
FIGS. 24A and 24B are graphs illustrating the new bone area as a function of time for various biostructure configurations in accordance with principles of the present invention.
Figure 24B:
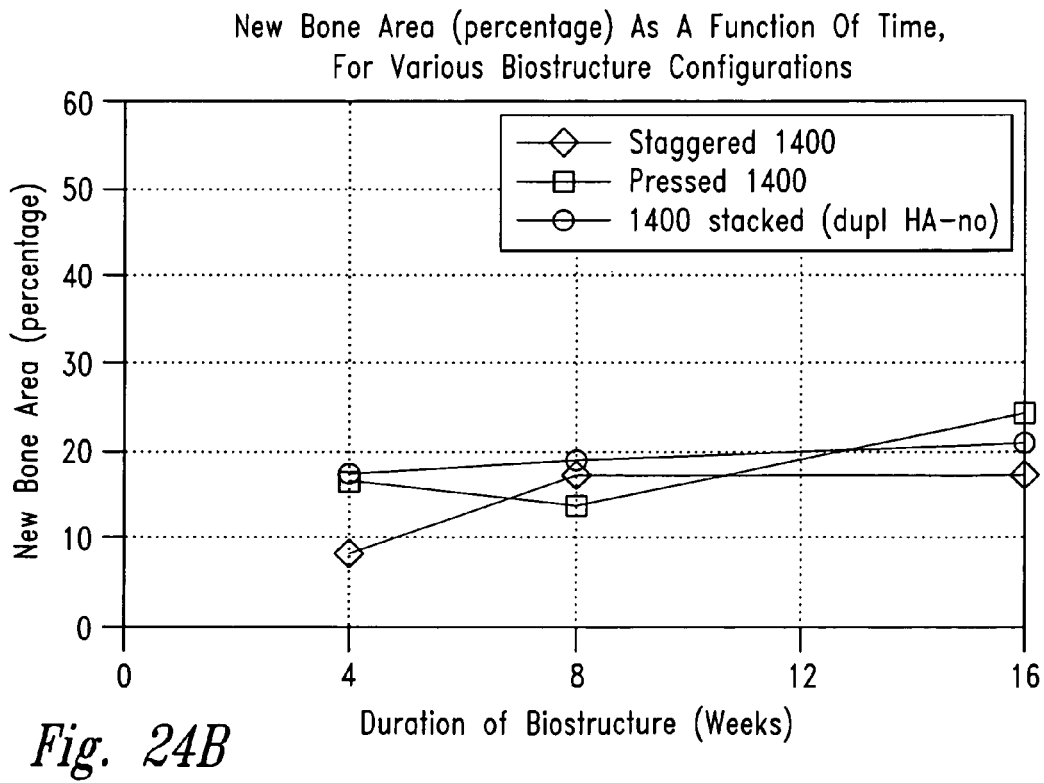

Temporally, no differences were found at any time point for all implant types, whether the results at 4 weeks are included or not. Since no major differences were found comparing available area, the total new bone area percentage out of the defect area was compared for all groups at all time points. FIGS. 24A and 24B illustrate the new bone area (percentage) as a function of time (weeks). The only significant increases found was for the 1400 Staggered implants between 4 weeks and 8 weeks (p=0.0425) and 4 weeks and 16 weeks (p=0.0076). If the unnormalized new bone area—the real bone area within the implants—is compared amongst all implant types and all time points, the only significant difference was for the 1400 Staggered implants between 4 weeks and 8 weeks (p=0.0405) and between 4 weeks and 16 weeks (p=0.0078).

TABLE 3

Mineral apposition rate (MAR), linear in-growth percentage, and new bone area percentage of implants at 4 weeks (n = 2).

|  | 1400 Stacked | 1400 Staggered | 1400 Pressed |
| --- | --- | --- | --- |
| MAR (um/day) | 3.56 ± .63 | 5.22 ± 1.10 | 4.39 ± .76 |
| Linear In-growth (%) | 43.57 ± 17.57 | 23.2 ± 15.67 | 44.81 ± 9.41 |
| New Bone Area / Available Area (%) | 17.35 ± 2.33 | 8.3 ± 8.15 | 16.7 ± 8.17 |

TABLE 4

Mineral apposition rate (MAR), linear in-growth percentage, and new bone area percentage of implants at 8 weeks (n = 2).

|  | 1400 Stacked (n = 6) | 1400 Staggered (n = 6) | 1400 Pressed (n = 6) |
| --- | --- | --- | --- |
| MAR (um/day) | 2.30 ± .51 | 2.83 ± .34 | 2.56 ± .45 |
| Linear In-growth (%) | 48.82 ± 25.23 | 46.5 ± 10.09 | 44.65 ± 18.77 |
| New Bone Area / Available Area (%) | 18.94 ± 12.89 | 16.63 ± 7.01 | 13.58 ± 7.77 |

TABLE 5

Mineral apposition rate (MAR), linear in-growth percentage, and new bone area percentage of implants at 16 weeks (n = 6).

|  | 1400 Stacked | 1400 Staggered | 1400 Pressed |
| --- | --- | --- | --- |
| MAR (um/day) | 2.05 ± .49 | 2.45 ± .59 | 1.73 ± .46 |
| Linear In-growth (%) | 53.77 ± 23.42 | 50.29 ± 16.87 | 44.19 ± 33.25 |
| New Bone Area / Available Area (%) | 20.61 ± 9.8 | 17.05 ± 4.1 | 23.75 ± 14.84 |

Conclusions

The unfilled negative controls had a healing response similar to previous studies at 8 weeks, with minimal amounts of new bone from the margins and high amounts of small new bone spicules and fibrous tissue in between the margins.

The autograft-filled positive controls had a healing response similar to previous studies at 8 weeks, with new bone filling the defects from the margins as well as around the unresorbed autograft particles.

The HA-Ch and HA-No implants had a favorable healing response with good osteoconduction and biocompatibility. The HA-Ch implants had an increased amount of new bone area percentage compared to the HA-No implants. New bone filled the HA-Ch implants through the radial and axial channels and the porosity. Compared to controls, the new bone area percentage of the HA-Ch implants was significantly higher than unfilled controls and similar to autograft-filled controls. It is however significant to note that the autograft filled defect includes both autograft particles and new bone.

As discussed above, approximately 35% of the total bone area is attributed to the originally placed autograft bone. If the autograft is removed from the total bone area percentage from the autograft-filled defects, the new bone area percentage reduced by that amount. Thus, the new bone area percentage in HA-Ch implants appears to exceed that of autograft-filled defects. This finding is of great significance because autograft is currently considered the standard of care for a bone defect. By using a synthetic material that matches, or even exceeds, the performance of autograft in a defect site, the risks involved in harvesting the autograft without compromising the biological response would be reduced.

Many studies have found the optimal scaffold pore size for new bone is between 200–400 um. In this study, pores less than 100 microns and macro-channels greater than 1000 microns generated high amounts of new bone. The results here showed that controlled scaffold macrogeometry, macrostructure and microarchitecture can influence levels of osteoconduction.

In the invention, of the particles which remain in or with the biostructure after removal of accessible unbound particles from macrostructures and other features by brushing, sonication, etc., it is believed that a high percentage of the particles partially sinter to other particles during the partial sintering operation. However, it is possible that there might be particles which do not touch any other particles sufficiently to become sintered to other particles, and yet are trapped inside the biostructure and remain with it. The presence of such particles is included in the present invention.

Figure 22:
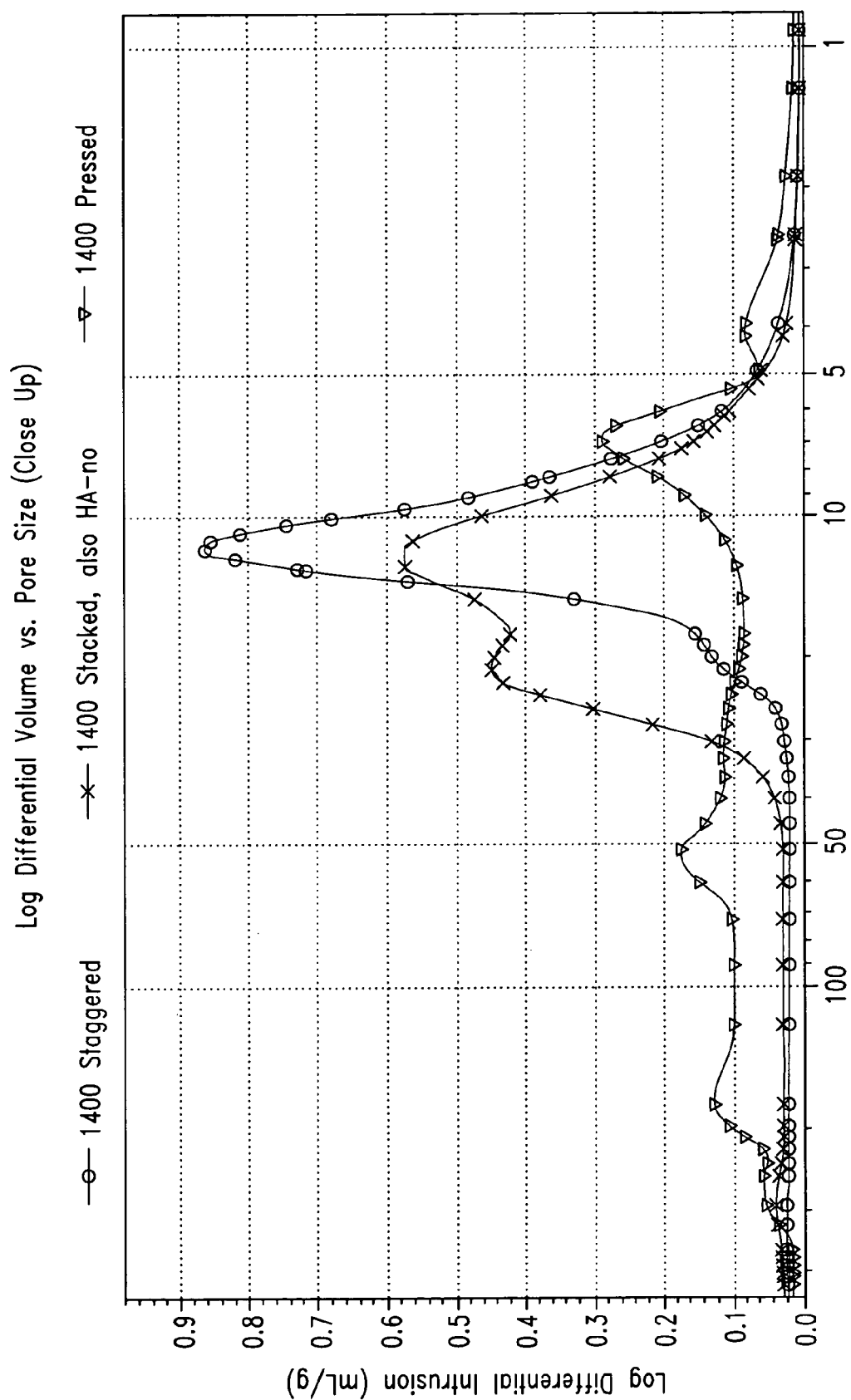
FIG. 22 is a graph illustrating the log differential intrusion volume versus the pore size diameter of given biostructures in accordance with principles of the present invention.

FIG. 22 illustrates that in the present invention, the pore size distribution may have a peak that is in the range of 8 microns to 20 microns. This is a departure from generally held teachings about optimum pore size for bone in-growth into bone augmentation implants, because the literature generally suggests that the pore size should be larger than 100 microns.

Until the present invention, the smallest dimension of a channel that could be achieved in a biostructure made by three-dimensional printing has been approximately the dimension of a primitive (described earlier herein). The dimension of a primitive has in turn been limited to an amount that is related to the dimension of a dispensed drop or other fluid feature, and the drop diameter has been limited by available printhead technology. With the present invention, it is possible to create empty spaces such that one of the dimensions of the empty space is substantially smaller than the cross-sectional dimension of a primitive. It is true that these empty regions may be irregular, and they tend to have only one dimension that is long. Nevertheless, these attributes are well suited for structures that are intended to promote the in-growth of bone, blood vessels, and the like.

Blood vessels are necessary to support any sustained in-growth of bone, because nutrients can travel only a short distance within a tissue by diffusion. If at any point blood vessels stop growing or existing, bone cells or cells of various other tissues can exist only a short distance further. In the present invention, blood vessels are observed to grow into the implants along with new bone cells. The diameter of the smallest blood vessels in humans is in the range of 20 to 30 microns. The diameter of the particles of powder used to make these implants is 40 microns. If implants were partially sintered in the ordinary manner for making isotropic implants, the pores between particles would be somewhat smaller than the dimension of the powder particle itself. At least some of the pores would be comparable to the blood vessel dimension.

It is also possible that implants may be made from slightly smaller powder particles such as an average particle diameter of 20 microns. The porosity of pressed implants made from powder particles having an average diameter of 20 microns has been measured by mercury porosimetry as having a peak at 8–12 microns, which is smaller than typical small blood vessels which suggests difficulty in growing blood vessels into such pores.

However, such measurements are for pressed implants not having meso-structure, and in the present invention it is still possible that the rearrangement of powder particles may cause mesostructural separations and empty spaces at boundaries between primitives, where the empty-space dimensions are several particle diameters, or even more. As a result, the dimensions of the mesostructures, where powder particles have moved away from each other, might be several times the average dimension of a powder particle and might be an appropriate size for blood vessels to grow into. So, it may be thought that the structure of the present invention provides mesostructures which are an appropriate size for blood vessels to grow into, and also provides smaller pores in between powder particles which are partially sintered to each other, which are smaller than the mesostructures and are an appropriate size for bone cells to grow into. It is not desired that the invention be limited to this explanation, however One important feature of the present experimental results is that, for the implants of the present invention that include both macrostructures and mesostructures, the observed new bone in-growth may exceed that observed with morselized autograft bone. Traditionally, morselized autograft bone has been viewed as the best possible filler material and the standard against which any bone substitute or augmentation material or biostructure should be compared.

New natural bone in-grows into the implants of the present invention, not only into the macrostructures, but also into the regions that contain mesostructures.

The Hydroxyapatite implants demonstrated remarkable bone in-growth. In-growth into the microstructure was not expected, as it has typically been believed in the literature that bone does not grow in pores smaller than 100–200 µm. The majority of pores in the Hydroxyapatite scaffolds were confirmed to be less than 50 µm by mercury porosimetry.

It can further be realized that although the implants of the present invention were made of hydroxyapatite, they could also have been made of tricalcium phosphate or other ceramic resembling substances found in natural bone. Many of those other substances are resorbable by the human body. Combinations of such substances could also be used as described herein. Therefore, using one or more of these other substances, an implant could be manufactured which, in addition to promoting excellent in-growth of natural bone, eventually is resorbed and is completely replaced by natural bone. This has not heretofore been achievable.

Figure 26A:
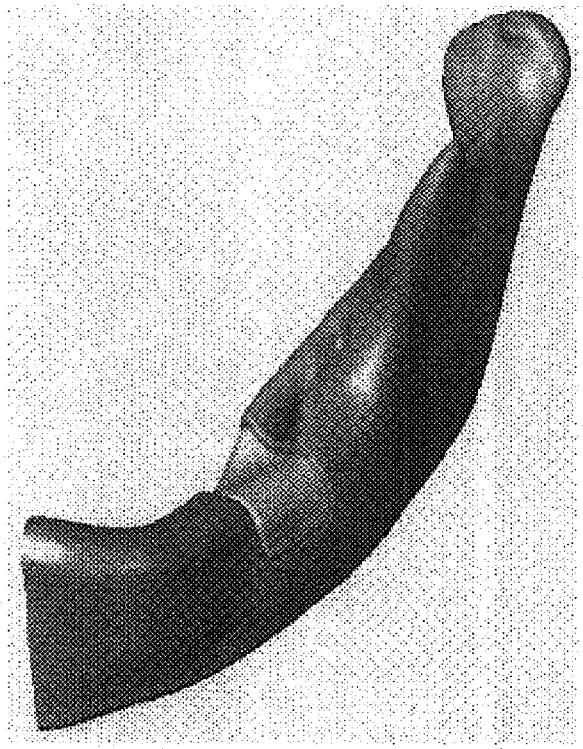
FIGS. 26A–C are views of engineered regenerative biostructures in accordance with principles of the present invention.
Figure 26B:
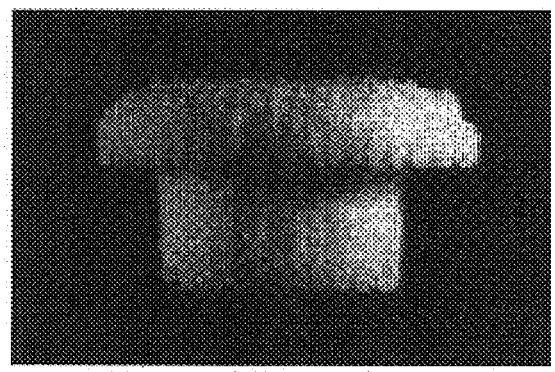
Figure 26C:

The invention can be used to make an augmentation or replacement of a segment of or even the entirety of almost any bone or bones in a patient's body. FIGS. 26A–26C illustrate some of the various biostructures that may be created in accordance with principles of the present invention. Articles made by the present invention may be load-bearing bones or bone segments, or they may be bones or bone segments which bear little or no load in the body. FIG. 26A illustrates a bone filler application shown in the mandibular region that may receive bearing load and little axial load. FIG. 26B illustrates a cranial plug that receives no load. FIG. 26C illustrates a full section mandibular biostructure, for joining pieces of the mandible which are completely separate from each other, that will be load bearing.

The design of the biostructure may also be influenced by factors that influence the rate of regeneration of natural bone, such as the location within a patient's body and the age of the patient. This consideration could influence the choice and composition of various substances in the biostructure, such as to determine the rate of resorption of those substances. The invention can be used to make a replacement for a piece removed from or missing from an otherwise intact bone, or it can be used to make a replacement for a segmental defect, i.e., a defect so extensive that the original bone is physically divided into separate pieces. Bones which may be repaired include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus tarsal and metatarsal and condyle bones.

The invention can be used to make articles that restore a bone to its original contours, or it can be used to make pieces that extend bones beyond the original boundaries of the bones. The biostructure may be dimensioned and shaped uniquely for a particular patient's body, or it could have standardized shape and dimensions. The invention can be used to make spinal fusion devices, which act to fuse together vertebrae that originally were separate and distinct from each other. The invention could be used to make basic shapes that can be carved or modified by a surgeon intraoperatively. The word augmentation is used here to refer to any biostructure installed in a bone, whether or not the biostructure when installed extends beyond the original boundaries of the bone.

The method described herein for making a three-dimensional printing biostructure with mesostructures could also be used for making articles for non-medical purposes.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

The various embodiments described above can be combined to provide further embodiments. Aspects of the invention can be modified, if necessary, to employ the process, apparatuses and concepts of the various patents, applications and publications described above to provide yet further embodiments of the invention. All patents, patent applications and publications cited herein are incorporated by reference in their entirety.

These and other changes can be made to the invention in light of the above detailed description. In general, in the following claims, the terms used should not be construed to limit the invention to the specific embodiments disclosed in the specification and the claims, but should be construed to include all devices that operate under the claims to provide a biostructure formed from powder and the associated method of manufacture. Accordingly, the invention is not limited by the disclosure, but instead the scope of the invention is to be determined entirely by the following claims.

We claim:

1. An osteoinductive or osteoconductive biostructure comprising a matrix of interconnected ceramic particles joined directly to each other and having at least one of a porous portion, wherein said porous portion comprises controlled particle packing providing controlled inter-particle pores, and further wherein said matrix of interconnected particles comprises multiple discrete regions having different compositions wherein the multiple discrete regions comprise a first region having a composition comprising hydroxyapatite and a second region having a composition comprising tricalcium phosphate, and wherein both the first region and the second region are porous, and further wherein said first and second porous regions have pore sizes that are approximately equal.

2. The biostructure of claim 1, wherein the biostructure further comprises macrochannels therethrough.

3. The biostructure of claim 1 produced by a process comprising heating a precursor biostructure, wherein the precursor biostructure comprises multiple discrete regions having different compositions, and wherein at least one of the multiple discrete regions comprises a different composition which converts to another substance by a chemical reaction initiated by said heating.

4. The biostructure produced by the process of claim 3, wherein said precursor biostructure further comprises a calcium-rich reactant that facilitates the chemical reaction.

5. The biostructure produced by the process of claim 4, wherein the calcium-rich reactant is selected from calcium carbonate, calcium oxide, calcium hydroxide, and combinations thereof.

6. The biostructure produced by the process of claim 3, wherein said precursor biostructure further comprises a phosphorus-rich reactant that facilitates the chemical reaction.

7. The biostructure produced by the process of claim 6, wherein the phosphorus-rich reactant is selected from dicalcium phosphate, monocalcium phosphate, phosphoric acid, ammonium phosphate, and combinations thereof.

8. An osteoinductive or osteoconductive biostructure comprising a matrix of interconnected ceramic particles joined directly to each other and having at least one of a porous portion, wherein said porous portion comprises controlled particle packing providing controlled inter-particle pores, and at least two intersecting macrochannels, and having an exterior surface wherein the exterior surface contains at least one groove.

9. The biostructure of claim 8, wherein said inter-particle pores have a pore size distribution having a peak in the range of 60 microns to 100 microns.

10. The biostructure of claim 8, wherein said biostructure comprises particles selected from calcium phosphates, hydroxyapatite, tricalcium phosphate, calcium salts, dental tooth enamel, aragonite, calcite, nacre, bioceramic and mixtures thereof.

11. The biostructure of claim 8, further comprising distinct regions of a first composition of hydroxyapatite and a second composition of tricalcium phosphate.

12. An osteoinductive or osteoconductive biostructure comprising a matrix of interconnected ceramic particles joined directly to each other and having at least one of a porous portion, wherein said porous portion comprises controlled particle packing providing controlled inter-particle pores, and macrochannels, wherein the biostructure further comprises, in space not otherwise occupied, a co-located polymer and bioactive substance.

13. The biostructure of claim 12, wherein said inter-particle pores have a pore size distribution having a peak in the range of 60 microns to 100 microns.

14. The biostructure of claim 12, wherein said biostructure comprises particles selected from calcium phosphates, hydroxyapatite, tricalcium phosphate, calcium salts, dental tooth enamel, aragonite, calcite, nacre, bioceramic and mixtures thereof.

15. The biostructure of claim 12, further comprising distinct regions of a first composition of hydroxyapatite and a second composition of tricalcium phosphate.

16. An osteoinductive or osteoconductive biostructure comprising a matrix of interconnected particles having at least one of a porous portion, wherein said porous portion comprises controlled particle packing providing controlled inter-particle pores, and having macrochannels such that at least three non-coplanar macrochannels intersect at a common location.

17. The biostructure of claim 16, wherein said controlled inter-particle pores have a pore size distribution having a peak in the range of 60 microns to 100 microns.

18. The biostructure of claim 16, wherein said matrix of interconnected particles comprises ceramic particles directly joined to each other.

19. The biostructure of claim 16, wherein said macrochannels have a cross-sectional dimension from 300 to 700 microns.

20. The biostructure of claim 16, wherein said macrochannels have a cross-sectional dimension from 1000 to 1600 microns.

21. The biostructure of claim 1, 8 or 16, wherein said biostructure further comprises a resorbable polymer.

22. The biostructure of claim 21, wherein said resorbable polymer is polylactic acid or polylactic co-glycolic acid.

23. The biostructure of claim 1, 8 or 16, wherein said biostructure further comprises a nonresorbable polymer.

24. The biostructure of claim 23, wherein said nonresorbable polymer is polymethylmethacrylate.

25. The biostructure of claim 1, 8 or 16, wherein said biostructure further comprises bioactive substances.

26. The biostructure of claim 25, wherein said bioactive substances comprise cells, cell fragments, cellular material, proteins, growth factors, hormones, active pharmaceutical ingredients, peptides, or mixtures thereof.

27. The biostructure of claims 1, 8, or 16, wherein the pores of said biostructure are at least partially occupied by a strengthening agent.

28. The biostructure of claim 27, wherein the pores are completely filled with said strengthening agent.

29. The biostructure of claim 27, wherein porous portions not occupied by said strengthening agent contain a bioactive substance.

30. The biostructure of claim 27, wherein said strengthening agent is selected from fibrin, fibrinogen, polymers, polylactic co-glycolic acid and combinations thereof.

31. The biostructure of claims 1, 8, 16, wherein the pores of said biostructure are filled with an interpenetrating material.

32. The biostructure of claim 31, wherein the interpenetrating material is a polymer.

33. The biostructure of claim 32, wherein said polymer is resorbable.

34. The biostructure of claim 32, wherein said polymer is non-resorbable.

35. The biostructure of claim 32, wherein said polymer is a comb polymer.

36. The biostructure of claim 31, wherein said interpenetrating material further comprises a bioactive substance.

37. The biostructure of claim 36, wherein the bioactive substance is selected from antibiotics, active pharmaceutical ingredients, anesthetics, anti-inflammatozy substances, growth promoting substances, hormones, peptides, bone morphogenic proteins, cells, cell fragments, cellular material, proteins, and growth factors.

38. An osteoinductive or osteoconductive biostructure comprising a matrix of interconnected ceramic particles joined directly to each other and having at least one of a porous portion, wherein said porous portion comprises controlled particle packing providing controlled inter-particle pores, wherein the pores of said porous portion are partially occupied with a strengthening agent, and wherein open spaces not occupied by said strengthening agent contain a bioactive substance.

39. The biostructure of claim 38, wherein said biostructure further comprises macrochannels.

40. The biostructure of claim 39, wherein said macrochannels have a cross-sectional dimension from 300 to 700 microns.

41. The biostructure of claim 39, wherein said macrochannels have a cross-sectional dimension from 1000 to 1600 microns.

42. The biostructure of claim 2, 8, 12, 16, or 39, wherein said macrochannels have uniform cross-sections, one or more non-uniform cross-sections, non-straight paths, branching, or dead-ends.

43. The biostructure of claim 38, wherein said biostructure comprises particles selected from calcium phosphates, hydroxyapatite, tricalcium phosphate, calcium salts, dental tooth enamel, aragonite, calcite, nacre, bioceramic and mixtures thereof.

44. The biostructure of claim 38, wherein the strengthening agent is a polymer.

45. The biostructure of claim 38, further comprising distinct regions of a first composition of hydroxyapatite and a second composition of tricalcium phosphate.

46. The biostructure of claim 1, 8, 12, 16, or 38, wherein said biostructure comprises a porosity between 30% and 70%.

47. The biostructure of claim 1, 8, 12, 16, or 38, wherein said particles are substantially spherical.

48. The biostructure of claim 1, 8, 12, 16, or 38, wherein said particles are substantially non-spherical.

49. The biostructure of claim 1, 8, 12, 16, or 38, wherein said particles are bound through the application of a binder liquid that is deposited on the particles in a staggered configuration.

50. The biostructure of claim 1, 8, 12, 16, or 38, wherein said particles are bound through the application of a binder liquid that is deposited on the particles in a stacked configuration.

51. The biostructure of claim 1, 8, 12, 16, or 38, wherein said biostructure is a bone substitute.

52. The biostructure of claim 51, wherein the biostructure is a bone substitute for at least a portion of a bone selected from the group consisting of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, nina, carpal bones, metacarpal bones, phalanges, ilium, ischium, pubis, femur, tibia, fibula, patella, calcaneus tarsal and metatarsal bones, and condyle.

53. A precursor biostnzcture comprising a matrix of ceramic particales joined to each other by a substance which decomposes into gaseous decomposition products at a first suitable temperature and having at least one of a porous portion, wherein said porous portion comprises controlled particle packing providing controlled inter-particle pores, and further wherein said matrix of interconnected particles comprises multiple discrete regions having different compositions, and wherein at least one of said multiple discrete regions having different compositions converts to another substance by a chemical reaction at a second suitable temperature.

54. The biostructure of claim 1, 12, 16, 38 or 53, wherein said biostructure comprises undercuts, recesses or interior voids.

55. The biostructure of claim 54, wherein said undercuts or recesses comprise dead-end channels, grooves, dimples or tread-like features.

56. The biostructure of claim 1, 8, 12, 16, 38, or 53, wherein said biostructure is uniquely shaped or dimensioned for implantation into an individual patient.

57. The precursor biostructure of claim 53, wherein said precursor biostructure comprises a calcium-rich reactant that facilitates the chemical reaction.

58. The precursor biostructure of claim 57, wherein the calcium-rich reactant is selected from calcium carbonate, calcium oxide, calcium hydroxide, and combinations thereof.

59. The precursor biostructure of claim 53, wherein said precursor biostructure comprises a phosphorus-rich reactant that facilitates the chemical reaction.

60. The precursor biostructure of claim 59, wherein the phosphorus-rich reactant is selected from dicalcium phosphate, monocalcium phosphate, phosphoric acid, ammonium phosphate, and combinations thereof.

* * * * *